US012753403B2

(12) United States Patent
Mazé et al.

(10) Patent No.: US 12,753,403 B2
(45) Date of Patent: Oct. 6, 2026

(54) METHOD FOR TRANSDUCING PROTEIN-PROTEIN INTERACTIONS

(71) Applicant: ETH ZÜRICH, Zürich (CH)

(72) Inventors: Alain Mazé, Saint Louis (FR); Yaakov Benenson, Binningen (CH)

(73) Assignee: ETH ZÜRICH, Zurich (CH)

( * ) Notice: Subject to any disclaimer, the term of this patent is extended or adjusted under 35 U.S.C. 154(b) by 1239 days.

(21) Appl. No.: 17/285,471

(22) PCT Filed: Oct. 15, 2019

(86) PCT No.: PCT/EP2019/077962

§ 371 (c)(1),
(2) Date: Apr. 15, 2021

(87) PCT Pub. No.: WO2020/078996

PCT Pub. Date: Apr. 23, 2020

(65) Prior Publication Data

US 2021/0340526 A1 Nov. 4, 2021

(30) Foreign Application Priority Data

Oct. 15, 2018 (EP) .................................... 18200357

(51) Int. Cl.
*C12N 15/10* (2006.01)
*C12N 9/12* (2006.01)
*G01N 33/68* (2006.01)

(52) U.S. Cl.
CPC ....... *C12N 15/1055* (2013.01); *C12N 9/1223* (2013.01); *G01N 33/6845* (2013.01); *C12Y 207/13001* (2013.01); *G01N 2500/02* (2013.01); *G01N 2500/10* (2013.01)

(58) Field of Classification Search
CPC .............. C12N 15/1055; C12N 9/1223; G01N 33/6845; G01N 2500/02; G01N 2500/10; C12Y 207/13001; C12Y 207/13003; C07K 2319/00; C07K 2319/71
See application file for complete search history.

(56) References Cited

U.S. PATENT DOCUMENTS

| | | | |
|---|---|---|---|
| 6,824,994 B2 | 11/2004 | Weisblum et al. | |
| 7,527,942 B2 | 5/2009 | Carey et al. | |
| 8,105,825 B2 | 1/2012 | Dhadialla et al. | |
| 9,284,562 B2 | 3/2016 | Collins et al. | |
| 9,458,509 B2 | 10/2016 | Benenson et al. | |
| 10,160,978 B2 * | 12/2018 | Benenson ...... | C12Y 207/13003 |
| 10,793,921 B2 | 10/2020 | Benenson et al. | |
| 2002/0055172 A1 | 5/2002 | Harrington | |
| 2009/0192101 A1 | 7/2009 | Hung et al. | |
| 2010/0175141 A1 | 7/2010 | Collins et al. | |
| 2013/0034907 A1 | 2/2013 | Collins et al. | |
| 2013/0202532 A1 | 8/2013 | Benenson et al. | |
| 2017/0159135 A1 | 6/2017 | Benenson et al. | |
| 2017/0226530 A1 * | 8/2017 | Benenson ............ | C12N 15/635 |
| 2021/0381001 A1 | 12/2021 | Benenson et al. | |
| 2023/0133209 A1 | 5/2023 | Benenson et al. | |
| 2024/0209357 A1 | 6/2024 | Benenson et al. | |

FOREIGN PATENT DOCUMENTS

| | | |
|---|---|---|
| CN | 101557818 | 10/2009 |
| CN | 106103705 A | 11/2016 |
| EP | 2684865 A1 | 1/2014 |
| JP | 2008545406 A | 12/2008 |
| JP | 2015063522 | 4/2015 |
| WO | WO-2007000668 A2 | 1/2007 |
| WO | WO-2007131774 A1 | 11/2007 |
| WO | WO-2008134593 A1 | 11/2008 |
| WO | 2008157572 | 12/2008 |
| WO | WO-2012012739 A2 | 1/2012 |
| WO | WO-2014093852 A1 | 6/2014 |
| WO | WO-2015185691 A1 | 12/2015 |
| WO | WO-2015185692 A1 | 12/2015 |
| WO | WO-2015188191 A1 | 12/2015 |
| WO | 2016201106 | 12/2016 |
| WO | WO-2017064566 A2 | 4/2017 |
| WO | WO-2017132552 A1 | 8/2017 |

(Continued)

OTHER PUBLICATIONS

Lloyd et al. Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*
Xie et al. Designing cell function: assembly of synthetic gene circuits for cell biology applications. NATuRe RevIewS | MoLECuLAr Cell BioLogy Reviews vol. 19 | Aug. 2018 | 507 (Year: 2018).*
Hansen et al. With supplemental. Transplantation of prokaryotic two-component signaling pathways into mammalian cells. PNAS | Nov. 4, 2014 | vol. 111 | No. 44 | 15705-15710 (Year: 2014).*
Cheung et al. Structural Analysis of Ligand Stimulation of the Histidine Kinase NarX. Structure 17, 190-201, Feb. 13, 2009 (Year: 2009).*

(Continued)

*Primary Examiner* — Daniel E Kolker
*Assistant Examiner* — Brian Hartnett
(74) *Attorney, Agent, or Firm* — Cooley LLP

(57) ABSTRACT

The present invention relates to a cell comprising a first nucleic acid sequence encoding a first polypeptide fused to the N-terminus of a first variant of a histidine kinase comprising a DHp domain and a CA domain, wherein said first variant does not comprise a transmembrane domain, a second nucleic acid sequence encoding a second polypeptide fused to the N-terminus of a second variant of said histidine kinase comprising a DHp domain and a CA domain, wherein said second variant does not comprise a transmembrane domain, and a third nucleic acid sequence encoding a response regulatory protein specifically phosphorylatable by said DHp domain of said first or said second variant. The present invention further relates to uses of the cell of the invention.

18 Claims, 20 Drawing Sheets

Specification includes a Sequence Listing.

(56) References Cited

FOREIGN PATENT DOCUMENTS

| | | | |
|---|---|---|---|
| WO | 2018146484 | 8/2018 | |
| WO | WO-2018146484 A1 * | 8/2018 | ........... C07K 14/245 |
| WO | WO-2020074956 A2 | 4/2020 | |
| WO | WO-2020078996 A1 | 4/2020 | |
| WO | WO-2021209813 A2 | 10/2021 | |
| WO | WO-2022117686 A1 | 6/2022 | |

OTHER PUBLICATIONS

Cavicchioli et al. The NarX and NarQ Sensor-Transmitter Proteins of Escherichia coli Each Require Two Conserved Histidines for Nitrate-Dependent Signal Transduction to NarLJournal of Bacteriology, May 1995, p. 2416-2424 (Year: 1995).*

Maze Alain et al: "Artificial signaling in mammalian cells enabled by prokaryotic two component system", Nature Chemical Biology, Nature Publishing Group US, New York, vol. 16, No. 2, Dec. 16, 2019 (Dec. 16, 2019), pp. 179-187, XP036996012, ISSN: 1552-4450, DOI: 10.1 038/S41589-019-0429-9.

Kanno et al "Intein-Mediated Reporter Gene Assay for Detecting Protein-Protein Interactions in Living Mammalian Cells" Anal. Chem. 2006, 78, 2, 556-560 Publication Date:Dec. 7, 2005 https://doi.org/10.1021/ac051451a.

Ganesh et al "Engineered fumarate sensing Escherichia coli based on novel chimeric two-component system" J Biotechnol. Dec. 2013;168(4):560-6. doi: 10.1016/j.jbiotec.2013.09.003. Epub Sep. 19, 2013.

Chen et al: Cloning, Screening and Sequence Analysis of Bovine Follicle-Stimulating Hormone cDNA, Northwest Agricultural Journal, vol. 1, 1992 (English abstract).

Hansen, Jonathan et al. "Transplantation of prokaryotic two-component signaling pathways into mammalian cells." Proceedings of the National Academy of Sciences of the United States of America vol. 111,44 (2014): 15705-10. doi:10.1073/pnas.1406482111.

Ganesh, Irisappan et al. "Construction of Methanol-Sensing Escherichia coli by the Introduction of a Paracoccus denitrificans MxaY-Based Chimeric Two-Component System." Journal of Microbiology and Biotechnology vol. 27,6 (2017): 1106-1111. doi:10.4014/jmb.1611.11070.

Al-Zaidy et al., "Health outcomes in spinal muscular atrophy type 1 following AVXS-101 gene replacement therapy". Pediatr Pulmonol. Feb. 2019;54(2):179-185.

Amendola et al., "A double-switch vector system positively regulates transgene expression by endogenous microRNA expression (miR-ON vector)". Molecular Therapy. May 1, 2013;21(5):934-46.

Angelici "Design and Implementation of Transcription Factor Based Gene Classifier Circuits". Doctoral Thesis. 2017. doi: 10.3929/ethz-b-000253961. 173 pages.

Angelici et al., "Synthetic biology platform for sensing and integrating endogenous transcriptional inputs in mammalian cells". Cell reports. Aug. 30, 2016;16(9):2525-37.

Antunes et al., "Programmable ligand detection system in plants through a synthetic signal transduction pathway". PLoS One. Jan. 25, 2011;6(1): 11 pages.

Atasoy et al., "A FLEX switch targets Channelrhodopsin-2 to multiple cell types for imaging and long-range circuit mapping". Journal of Neuroscience. Jul. 9, 2008;28(28):7025-30.

Auslander et al., "A synthetic multifunctional mammalian pH sensor and CO2 transgenecontrol device". Mol Cell. Aug. 7, 2014;55(3):397-408 with Supplemental Info, 48 pages.

Auslander et al., "From gene switches to mammalian designer cells: present and future prospects". Trends Biotechnol. Mar. 2013;31(3):155-68.

Auslander et al., "Programmable single-cell mammalian biocomputers". Nature. Jul. 5, 2012;487(7405):123-7.

Ayoubi et al., "Regulation of gene expression by alternative promoters". The FASEB Journal. Mar. 1996;10(4):453-60.

Backman et al., "Use of synchronous site-specific recombination in vivo to regulate gene expression". Bio/Technology. Dec. 1, 1984;2(12):1045-9.

Bashor et al., "Complex signal processing in synthetic gene circuits using cooperative regulatory assemblies". Science. May 10, 2019;364(6440):593-7.

Benenson et al.., "An autonomous molecular computer for logical control of gene expression". Nature. May 27, 2004;429(6990):423-9.

Benenson et al., "Biomolecular computing systems: principles, progress and potential". Nature Reviews Genetics. Jul. 2012;13(7):455-68.

Besant et al., "Mammalian histidine kinases. Biochimica et Biophysica Acta (BBA)-Proteins and Proteomics". Dec. 30, 2005;1754(1-2):281-90.

Böger et al., "Functional determinants for the tetracycline-dependent transactivator tTA in transgenic mouse embryos". Mechanisms of development. May 1, 1999;83(1-2):141-53.

Bindels et al., "mScarlet: a bright monomeric red fluorescent protein for cellular imaging". Nature methods. Jan. 2017;14(1):53-6.

Bonnet et al., "Amplifying genetic logic gates". Science. May 3, 2013;340(6132):599-603.

Brown et al., "Endogenous microRNA regulation suppresses transgene expression in hematopoietic lineages and enables stable gene transfer". Nature medicine. May 1, 2006;12(5):585-91.

Bruce et al., "Identification of a motif in the C terminus of herpes simplex virus regulatory protein ICP4 that contributes to activation of transcription". Journal of virology. Jan. 1, 2002;76(1):195-207.

Buchler et al., "On schemes of combinatorial transcription logic". Proceedings of the National Academy of Sciences. Apr. 29, 2003;100(9):5136-41.

Callura et al., "Tracking, tuning, and terminating microbial physiology using synthetic riboregulators". Proceedings of the National Academy of Sciences. Sep. 7, 2010;107(36):15898-903.

Ceroni et al., "Burden-driven feedback control of gene expression". Nature methods. May 1, 2018;15(5):387-93.

Chen et al., "Synthetic biology: advancing biological frontiers by building synthetic systems". Genome biology. Feb. 2012;13: 10 pages.

Cho et al., "Universal chimeric antigen receptors for multiplexed and logical control of T cell responses". Cell. May 31, 2018;173(6):1426-38.

Choudhury et al., "In Vivo Selection Yields AAV-B1 Capsid for Central Nervous System and Muscle Gene Therapy". Mol Ther. Aug. 2016;24(7): 1247-57.

Close et al., "Autonomous Bioluminescent Expression of the Bacterial Luciferase Gene Cassette (Lux) in a Mammalian Cell Line", PLoS One, Aug. 27, 2010, 5(8), 12 pages.

Conway et al. "High-titer recombinant adeno-associated virus production utilizing a recombinant herpes simplex virus type 1 vector expressing AAV-2 Rep and Cap" Cap. Gene Therapy. Jun. 1999;6(6):986-93.

Coulouarn et al., "Loss of miR-122 expression in liver cancer correlates with suppression of the hepatic phenotype and gain of metastatic properties". Oncogene. Oct. 8, 2009;28(40):3526-36.

Cox et al., "Programming gene expression with combinatorial promoters". Molecular systems biology. Nov. 13, 2007;3(1): 11 pages.

Culler et al., "Reprogramming cellular behavior with RNA controllers responsive to endogenous proteins". Science. Nov. 26, 2010;330(6008):1251-5.

Dagogo-Jack et al.. Tumour heterogeneity and resistance to cancer therapies. Nat Rev Clin Oncol. Feb. 2018;15(2):81-94.

Dale et al., "Gene transfer with subsequent removal of the selection gene from the host genome". Proceedings of the National Academy of Sciences. Dec. 1, 1991;88(23):10558-62.

Dastor et al., "A workflow for in vivo evaluation of candidate inputs and outputs for cell classifier gene circuits". ACS synthetic biology. Feb. 16, 2018;7(2):474-89.

Deans et al., "A tunable genetic switch based on RNAi and repressor proteins for regulating gene expression in mammalian cells". Cell. Jul. 27, 2007;130(2):363-72.

(56) References Cited

OTHER PUBLICATIONS

Della Peruta et al., "Preferential targeting of disseminated liver tumors using a recombinant adeno-associated viral vector". Hum Gene Ther. Feb. 2015;26(2):94-103.
Dhungel et al., "MicroRNA199a-based post-transcriptional detargeting of gene vectors for hepatocellular carcinoma". Molecular Therapy-Nucleic Acids. Dec. 7, 2018;13:78-88.
Dhungel et al., "MicroRNA-Regulated Gene Delivery Systems for Research and Therapeutic Purposes". Molecules. Jun. 21, 2018;23(7): 14 pages.
Donahue et al., "The COMET toolkit for composing customizable genetic programs in mammalian cells". Nature communications. Feb. 7, 2020;11(1): 19 pages.
Dorer et al., "Targeting cancer by transcriptional control in cancer gene therapy and viral oncolysis". Advanced drug delivery reviews. Jul. 2, 2009;61(7-8):554-71.
Doshi et al., "Multiple alternative promoters and alternative splicing enable universal transcription-based logic computation in mammalian cells". Cell Reports. Dec. 1, 2020;33(9), 35 pages.
Duan et al., "Consequences of DNA-dependent protein kinase catalytic subunit deficiency on recombinant adeno-associated virus genome circularization and heterodimerization in muscle tissue". J Virol. Apr. 2003;77(8):4751-9.
Dull et al., "A third-generation lentivirus vector with a conditional packaging system" J Virol (1998) 71(11):8463-8471.
Dunlop et al., "Regulatory activity revealed by dynamic correlations in gene expression noise." Nature genetics. Dec. 2008;40(12):1493-8.
Elowitz et al., "A synthetic oscillatory network of transcriptional regulators". Nature. Jan. 20, 2000;403(6767):335-8.
"Encode" definition; Oxford dictionary; http://www.oxforddictionaries.com/us/definition/american-english/encode; accessed Apr. 27, 2015; 4 pages.
Eperon et al., "Pathways for selection of 5' splice sites by U1 snRNPs and SF2/ASF". The EMBO journal. Sep. 1, 1993;12(9):3607-17.
Eroshenko et al., "Mutants of Cre recombinase with improved accuracy". Nature communications. Sep. 23, 2013;4(1): 10 pages.
Eszterhas et al., "Transcriptional interference by independently regulated genes occurs in any relative arrangement of the genes and is influenced by chromosomal integration position" Molecular and Cellular Biology. 2002. 12 pages.
Filonov et al., "Deep-tissue photoacoustic tomography of a genetically encoded near-infrared fluorescent probe". Angewandte Chemie International Edition. Feb. 6, 2012;51(6):1448-51.
Freeman "The bystander effect: tumor regression when a fraction of the tumor mass is genetically modified". Cancer Res . . . 1994;53:1503-6.
Friedland et al., "Synthetic gene networks that count". science. May 29, 2009;324(5931):1199-202.
Fussenegger et al., Streptogramin-based gene regulation systems for mammalian cells. Nat Biotechnol. Nov. 2000;18(I I):1203-8.
Gaildrat et al., "Use of splicing reporter minigene assay to evaluate the effect on splicing of unclassified genetic variants". Cancer susceptibility: Methods and protocols. 2010:249-57.
Gam et al., "A mixed antagonistic/synergistic miRNA repression model enables accurate predictions of multi-input miRNA sensor activity". Nature communications. Jun. 22, 2018;9(1):12 pages.
Gao et al., "Programmable protein circuits in living cells". Science. Sep. 21, 2018;361(6408):1252-8.
Gardner et al. "Construction of a genetic toggle switch in *Escherichia coli*". Nature. Jan. 20, 2000;403(6767):339-42.
Genoway "Tet-On-Off Technology" product literature, 6 pages, 2004. retrieved from https://www.genoway.com/technologies/tet-system).
Gibson et al., "Enzymatic assembly of DNA molecules up to several hundred kilobases". Nature methods. May 2009;6(5):343-5.
Gil et al., "Position-dependent sequence elements downstream of AAUAAA are required for efficient rabbit B-globin mRNA 3' end formation". Cell. May 8, 1987;49(3):399-406.
Glatzel et al., "Adenoviral and adeno-associated viral transfer of genes to the peripheral nervous system". Proceedings of the National Academy of Sciences. Jan. 4, 2000;97(1):442-7.
Greber et al., "Mammalian synthetic biology: engineering of sophisticated gene networks". Journal of biotechnology. Jul. 15, 2007;130(4):329-45.
Green et al., "Complex cellular logic computation using ribocomputing devices". Nature. Aug. 3, 2017;548(7665):117-21.
Grimm et al. "In vitro and in vivo gene therapy vector evolution via multispecies interbreeding and retargeting of adeno-associated viruses" Journal of Virology (2008); 82(12):5887-5911.
Grindley, et al., "Mechanisms of Site-Specific Recombination". Annu Rev Biochem. (2006); 75: 567-605.
Guo et al.. "Expression features of SOX9 associate with tumor progression and poor prognosis of hepatocellular carcinoma". Diagn Pathol. Apr. 19, 2012;7: 7 pages.
Haefliger et al., "Precision multidimensional assay for high-throughput microRNA drug discovery". Nat Commun. Feb. 16, 2016;7: 12 pages.
Ham et al., "Design and construction of a double inversion recombination switch for heritable sequential genetic memory". PLoS One. Jul. 30, 2008;3(7): 9 pages.
Harries et al., "Species-specific differences in the expression of the HNF1A, HNF1B and HNF4A genes". PLoS One. Nov. 16, 2009:4(1 I): 7 pages.
Haynes A sensitive switch for visualizing natural gene silencing in single cells. ACS synthetic biology. Mar. 16, 2012;1(3):99-106.
Heinz et al., "Graded or threshold response of the tet-controlled gene expression: all depends on the concentration of the transactivator". BMC Biotechnol. Jan. 22, 2013;13:5. 12 pages.
Hermsen et al., "Transcriptional regulation by competing transcription factor modules". PLoS Comput Biol. Dec. 1, 2006;2(12): 9 pages.
Huang et al., "Oncolytic adenovirus programmed by synthetic gene circuit for cancer immunotherapy". Nature communications. Oct. 22, 2019;10(1): 15 pages.
Indra et al., "Temporally-controlled site-specific mutagenesis in the basal layer of the epidermis: comparison of the recombinase activity of the tamoxifen-inducible Cre-ERT and Cre-ERT2 recombinases". Nucleic acids research. Nov. 1, 1999;27(22):4324-7.
International Search Report and Written Opinion for PCT Application No. PCT/EP2015/062507 mailed Aug. 10, 2015, 15 pages.
International Search Report and Written Opinion for PCT Application No. PCT/EP2015/062508 mailed Jul. 23, 2015, 11 pages.
International Search Report and Written Opinion for PCT Application No. PCT/EP2019/077962 mailed Jan. 20, 2020, 12 pages.
International Search Report and Written Opinion for PCT Application No. PCT/EP2021/083846 mailed Feb. 24, 2022, 14 pages.
International Search Report and Written Opinion for PCT Application No. PCT/IB2019/001100 mailed Apr. 1, 2020, 18 pages.
International Search Report and Written Opinion for PCT Application No. PCT/IB2021/000246 mailed Dec. 3, 2021, 32 pages.
International Search Report and Written Opinion for PCT Application No. PCT/US2011/045038 mailed Mar. 28, 2012, 17 pages.
Invitation to Pay Additional Fees for International Application No. PCT/IB2019/001100, mailed Feb. 11, 2020, 16 pages.
Invitation to Pay Additional Fees for International Application No. PCT/IB2021/000246, mailed Oct. 12, 2021, 24 pages.
Iyer et al., "Two-step transcriptional amplification as a method for imaging reporter gene expression using weak promoters". Proceedings of the National Academy of Sciences. Dec. 4, 2001;98(25):14595-600.
June et al., "CAR T cell immunotherapy for human cancer". Science. Mar. 23, 2018;359(6382):1361-5.
Juttner et al., "Targeting neuronal and glial cell types with synthetic promoter AAVs in mice, non-human primates and humans". Nat Neurosci. Aug. 2019;22(8): 1345-1356.
Kanegae et al., "High-level expression by tissue/cancer-specific promoter with strict specificity using a single-adenoviral vector". Nucleic acids research. Jan. 1, 2011;39(2): 13 pages.

(56) References Cited

OTHER PUBLICATIONS

Keeler et al., "Recombinant adeno-associated virus gene therapy in light of Luxturna (and Zolgensma and Glybera): where are we, and how did we get here?". Annual review of virology. Sep. 29, 2019;6(1):601-21.
Kloss et al., "Combinatorial antigen recognition with balanced signaling promotes selective tumor eradication by engineered T cells". Nature biotechnology. Jan. 2013;31(1):71-5.
Kota et al., "Therapeutic microRNA delivery suppresses tumorigenesis in a murine liver cancer model". Cell. Jun. 12, 2009;137(6): 1005-17.
Kozak "Point mutations define a sequence flanking the AUG initiator codon that modulates translation by eukaryotic ribosomes," Cell. Jan. 31, 1986; 44(2):283-92.
Kramer et al., "BioLogic gates enable logical transcription control in mammalian cells". Biotechnology and bioengineering. Aug. 20, 2004;87(4):478-84.
Kubokawa et al., "Molecular characterization of the 5'-UTR of retinal dystrophin reveals a cryptic intron that regulates translational activity". Molecular vision. Dec. 7, 2010;16: 8 pages.
Landegger et al., "A synthetic AAV vector enables safe and efficient gene transfer to the mammalian inner ear". Nat Biotechnol. Mar. 2017;35(3):280-284.
Lapique et al., "Digital switching in a biosensor circuit via programmable timing of gene availability". Nature chemical biology. Dec. 2014;10(12):1020-7.
Lapique et al., "Genetic programs can be compressed and autonomously decompressed in live cells". Nature nanotechnology. Apr. 2018;13(4):309-15.
Leisner et al., "Rationally designed logic integration of regulatory signals in mammalian cells". Nature nanotechnology. Sep. 2010;5(9):666-70.
Li et al., "Deletions of the Aequorea victoria green fluorescent protein define the minimal domain required for fluorescence". Journal of Biological Chemistry. Nov. 7, 1997;272(45):28545-9.
Liao et al., "Identification of SOX4 target genes using phylogenetic footprinting-based prediction from expression microarrays suggests that overexpression of SOX4 potentiates metastasis in hepatocellular carcinoma". Oncogene. Sep. 18, 2008;27(42):5578-89.
Lillacci et al., "Synthetic control systems for high performance gene expression in mammalian cells". Nucleic Acids Res. Oct. 12, 2018;46(18):9855-9863.
Lin et al., "How different eukaryotic transcriptional activators can cooperate promiscuously". Nature. May 24, 1990;345(6273):359-61.
Liu et al., "Synthesizing and gate genetic circuits based on CRISPR-Cas9 for identification of bladder cancer cells". Nat Commun. Nov. 6, 2014;5: 7 pages.
Liu, Z. et al., "Systematic comparison of 2A peptides for cloning multi-genes in a polycistronic vector," Scientific reports. May 19, 2017;7(1); 9 pages.
Llovet et al., "mRECIST for HCC: performance and novel refinements". Journal of hepatology. Feb. 1, 2020;72(2):288-306.
Lohmueller et al., "A tunable zinc finger-based framework for Boolean logic computation in mammalian cells". Nucleic acids research. Jun. 1, 2012;40(11):5180-7.
Lois et al., Germline transmission and tissue-specific expression of transgenes delivered by lentiviral vectors. science. Feb. 1, 2002;295(5556):868-72.
Lytle et al., "Target mRNAs are repressed as efficiently by microRNA-binding sites in the 5' UTR as in the 3' UTR". Proceedings of the National Academy of Sciences. Jun. 5, 2007;104(23):9667-72.
Mansfield et al., "MicroRNA-responsive 'sensor' transgenes uncover Hox-like and other developmentally regulated patterns of vertebrate microRNA expression," Nature genetics. Oct. 1, 2004;36(10):1079-83.
Mathur et al., "Programmable mutually exclusive alternative splicing for generating RNA and protein diversity". Nature communications. Jun. 17, 2019;10(1): 13 pages.
Misirly et al. "A computational workflow for the automated generation of models of genetic designs". ACS synthetic biology. May 21, 2018;8(7):1548-59.
Miyaso et al., "An intronic splicing enhancer element in survival motor neuron (SMN) pre-mRNA". Journal of Biological Chemistry. May 2, 2003;278(18):15825-31.
Mohammadi et al., "Automated design of synthetic cell classifier circuits using a two-step optimization strategy". Cell systems. Feb. 22, 2017;4(2):207-18.
Morel et al., "Cellular heterogeneity mediates inherent sensitivity-specificity tradeoff in cancer targeting by synthetic circuits". Proc Natl Acad Sci USA. Jul. 19, 2016:113(29):8133-8.
Muhlethaler-Mottet et al., "Expression of MHC class II molecules in different cellular and functional compartments is controlled by differential usage of multiple promoters of the transactivator CIITA." The EMBO journal. May 15, 1997. 10 pages.
Mukherji et al., "Synthetic biology: understanding biological design from synthetic circuits". Nature Reviews Genetics. Dec. 2009;10(12):859-71.
Navarro et al.. "Cancer suicide gene therapy: a patent review". Expert Opin Ther Pat. Sep. 2016;26(9): 1095-104.
Nelson et al., "In vivo genome editing improves muscle function in a mouse model of Duchenne muscular dystrophy". Science. Jan. 22, 2016;351(6271):403-7.
Nickerson et al., "Dendritic cell-specific MHC class II transactivator contains a caspase recruitment domain that confers potent transactivation activity". Journal of Biological Chemistry. Jun. 1, 2001;276(22):19089-93.
Nielsen et al., "Advances in genetic circuit design: novel biochemistries, deep part mining, and precision gene expression". Current opinion in chemical biology. Dec. 1, 2013;17(6):878-92.
Nielsen et al., "Genetic circuit design automation". Science. Apr. 1, 2016;352(6281):10 pages.
Nissim et al., "A tunable dual-promoter integrator for targeting of cancer cells". Mol Syst Biol. Dec. 21, 2010;6: 9 pages.
Nissim et al., "Synthetic RNA-Based Immunomodulatory Gene Circuits for Cancer Immunotherapy". Cell. Nov. 16, 2017;171(5):1138-1150.
Papadakis et al. "Promoters and Control Elements: Designing Expression Cassettes for Gene Therapy." Current Gene Therapy (2004); 4(1): 89-113.
Paterna et al., "Transduction profiles of recombinant adeno-associated virus vectors derived from serotypes 2 and 5 in the nigrostriatal system of rats". Journal of virology. Jul. 1, 2004;78(13):6808-17.
Piovesan et al., "Identification of minimal eukaryotic introns through GeneBase, a user-friendly tool for parsing the NCBI Gene databank". DNA Research. Dec. 1, 2015;22(6):495-503.
Poling et al., "A lentiviral vector bearing a reverse intron demonstrates superior expression of both proteins and microRNAs". RNA biology. Nov. 2, 2017;14(11):1570-9.
Prochazka et al., "Highly modular bow-tie gene circuits with programmable dynamic behaviour". Nature communications. Oct. 14, 2014;5(1): 12 pages.
Richtig et al., "SOX9 is a proliferation and stem cell factor in hepatocellular carcinoma and possess widespread prognostic significance in different cancer types". PLoS One. Nov. 9, 2017;12(II): 15 pages.
Rickman et al., "A two-component signal transduction system with a PAS domain-containing sensor is required for virulence of *Mycobacterium tuberculosis* in mice". Biochemical and biophysical research communications. Jan. 30, 2004;314(1):259-67.
Rinaudo et al., "A universal RNAi-based logic evaluator that operates in mammalian cells". Nature biotechnology. Jul. 2007;25(7):795-801.
Rizzo et al., "High-contrast imaging of fluorescent protein FRET by fluorescence polarization microscopy". Biophysical journal. Feb. 1, 2005;88(2); 3 pages.
Robson et al., "Transcriptional targeting in cancer gene therapy". BioMed Research International. 2003;2003(2):110-37.
Rosenberg et al., "Learning the sequence determinants of alternative splicing from millions of random sequences". Cell. Oct. 22, 2015;163(3):698-711.

(56) References Cited

OTHER PUBLICATIONS

Roybal et al., "Engineering T cells with customized therapeutic response programs using synthetic notch receptors". Cell. Oct. 6, 2016;167(2):419-32.
Ruiz et al., "MicroRNA-Detargeted Mengovirus for Oncolytic Virotherapy", Journal of Virology, Apr. 2016, vol. 90, pp. 4078-4092.
Sakaguchi et al., "Robust cancer-specific gene expression by a novel cassette with hTERT and CMV promoter elements". Oncology reports. Feb. 2017;38(2):1108-14.
Sasaki-Haraguchi et al., "Mechanistic insights into human pre-mRNA splicing of human ultra-short introns: potential unusual mechanism identifies G-rich introns". Biochemical and biophysical research communications. Jun. 29, 2012;423(2):289-94.
Schnutgen et al., "A directional strategy for monitoring Cre-mediated recombination at the cellular level in the mouse," Nature Biotechnology, 2003, vol. 21, pp. 562-565.
Scholl et al., "Emerging therapies for inherited retinal degeneration". Science translational medicine. Dec. 7, 2016;8(368):10 pages.
Schramm et al., "InSiDDe: A server for designing artificial disordered proteins". International journal of molecular sciences. Dec. 29, 2017;19(1): 15 pages.
Schreiber et al., "Model-guided combinatorial optimization of complex synthetic gene networks". Molecular Systems Biology. Dec. 2016;12(12): 14 pages.
Sektas et al., "Expression plasmid with a very tight two-step control: Int/att-mediated gene inversion with respect to the stationary promoter". Gene. Apr. 18, 2001;267(2):213-20.
Sektas et al., "Tightly controlled two-stage expression vectors employing the Flp/FRT-mediated inversion of cloned genes". Molecular biotechnology. Feb. 1998;9:17-24.
Shahbazi et al., "Immunostimulants: types and functions". Journal of Medical Microbiology and Infectious Diseases. Jul. 10, 2016;4(3):45-51.
Shcherbakova et al., "Bright monomeric near-infrared fluorescent proteins as tags and biosensors for multiscale imaging". Nature communications. Aug. 19, 2016;7(1):12 pages.
Siegert et al., "Transcriptional code and disease map for adult retinal cell types". Nature neuroscience. Mar. 2012; 15(3):487-95.
Siuti et al., "Synthetic circuits integrating logic and memory in living cells". Nature biotechnology. May 2013;31(5):448-52.
Sohn et al., A Single Vector Platform for High-Level Gene Transduction of Central Neurons: Adeno-Associated Virus Vector Equipped with the Tet-Off System PLoS One. Jan. 6, 2017;12(1): 22 pages.
Stanton et al., "Systematic transfer of prokaryotic sensors and circuits to mammalian cells". ACS synthetic biology. Dec. 19, 2014;3(12):880-91.
Szymanski et al., "Development and validation of a robust and versatile one-plasmid regulated gene expression system". Mol Ther. Jul. 2007; 15(7):1340-7.
Tamsir et al., "Robust multicellular computing using genetically encoded NOR gates and chemical 'wires'". Nature. Jan. 13, 2011;469(7329):212-5.
Tastanova et al., "Synthetic biology-based cellular biomedical tattoo for detection of hypercalcemia associated with cancer. Science translational medicine". Apr. 18, 2018;10(437), 11 pages.
Uhlen et al., "A pathology atlas of the human cancer transcriptome". Science. Aug. 18, 2017;357(6352): 13 pages.
Uphoff et al., "Detecting mycoplasma contamination in cell cultures by polymerase chain reaction". Cancer cell culture: methods and protocols. 2011:93-103.
Vilaboa et al., "Gene Switches for Deliberate Regulation of Transgene Expression: Recent Advances in System Development and Uses", J Genet Syndr Gene Ther. 2011;2(107): 23 pages.
Wang et al., "Intronic splicing enhancers, cognate splicing factors and context-dependent regulation rules". Nature structural & molecular biology. Oct. 2012;19(10):1044-52.
Weber et al., "A synthetic mammalian gene circuit reveals antituberculosis compounds". Proceedings of the National Academy of Sciences. Jul. 22, 2008;105(29):9994-8.
Weber et al., "Emerging biomedical applications of synthetic biology". Nat Rev Genet. Nov. 29, 2011;13(I):21-35.
Weber et al., "Engineering of synthetic mammalian gene networks." Chemistry & biology. Mar. 27, 2009;16(3):287-97.
Weber et al., "Macrolide-based transgene control in mammalian cells and mice". Nat Biotechnol. Sep. 2002;20(9):901-7.
Weinberg et al., "Large-scale design of robust genetic circuits with multiple inputs and outputs for mammalian cells". Nature biotechnology. May 2017;35(5):453-62.
Xie et al., "Multi-input RNAi-based logic circuit for identification of specific cancer cells". Science. Sep. 2, 2011;333(6047):1307-11.
Yang et al., "Enzyme-mediated hydrolytic activation of prodrugs". Acta Pharmaceutica Sinica B. Oct. 1, 2011;1(3):143-59.
Ye et al., "Self-adjusting synthetic gene circuit for correcting insulin resistance". Nat Biomed Eng. Jan. 2017;I(I): 21 pages.
Yeo et al., "Maximum entropy modeling of short sequence motifs with applications to RNA splicing signals". InProceedings of the seventh annual international conference on Research in computational molecular biology Apr. 10, 2003 pp. 322-331.
You et al., "Programmed population control by cell-cell communication and regulated killing". Nature. Apr. 22, 2004;428(6985):868-71.
Zah et al., "T cells expressing CD19/CD20 bispecific chimeric antigen receptors prevent antigen escape by malignant B cells". Cancer immunology research. Jun. 1, 2016;4(6):498-508.
Zhang et al., "Design of a dynamic sensor-regulator system for production of chemicals and fuels derived from fatty acids". Nature biotechnology. Apr. 2012;30(4):354-9.
Zhang F. et al. "Efficient construction of sequence-specific TAL effectors for modulating mammalian transcription" Nature Biotechnology (2011); 29(2):149-153.
Zhou et al., "SOX10 is a novel oncogene in hepatocellular carcinoma through Wnt/β-catenin/TCF4 cascade". Tumour Biol. Oct. 2014;35(10):9935-40.

* cited by examiner

B

A

B

B

A

C
Cerulean, a.u.
1.5
1
0.5
0
x9.4
CMV::Tango
D
Cerulean, a.u.
0.1
0.05
0
x151
x137
NarX
NarX379to598
NarX379to598H399Q (Hmut)
NarX379to598N509A (Nmut)
β-arrestin::Hmut
β-arrestin::Nmut
ADRB2-AVPR2::Hmut
ADRB2-AVPR2::Nmut

| | 1 | 2 | 3 | 4 | 5 | 6 | 7 | 8 | 9 | 10 |
|---|---|---|---|---|---|---|---|---|---|---|
| NarX | – | + | – | – | – | – | – | – | – | – |
| NarX$^{379to598}$ | – | – | + | – | – | – | – | – | – | – |
| SynZip1::NarX$^{379to598}$ | – | – | – | + | – | + | – | – | – | – |
| SynZip2::NarX$^{379to598}$ | – | – | – | – | + | + | – | – | – | – |
| NarX$^{379to598}$H399Q (H$^{mut}$) | – | – | – | – | – | – | + | – | – | – |
| NarX$^{379to598}$N509A (N$^{mut}$) | – | – | – | – | – | – | + | – | – | – |
| SynZip1::H$^{mut}$ | – | – | – | – | – | – | – | + | – | + |
| SynZip2::N$^{mut}$ | – | – | – | – | – | – | – | – | + | + |

a

| | 1 | 2 | 3 | 4 | 5 | 6 | 7 | 8 | 9 |
|---|---|---|---|---|---|---|---|---|---|
| NarX | − | + | − | − | − | − | − | − | − |
| NarX$^{379to598}$ | − | − | + | − | − | − | − | − | − |
| NarX$^{379to598}$H399Q (H$^{mut}$) | − | − | − | + | − | − | − | − | − |
| NarX$^{379to598}$N509A (N$^{mut}$) | − | − | − | − | + | − | − | − | − |
| FK::H$^{mut}$ | − | − | − | − | − | + | − | − | − |
| FK::N$^{mut}$ | − | − | − | − | − | − | + | − | − |
| FR::H$^{mut}$ | − | − | − | − | − | − | − | + | − |
| FR::N$^{mut}$ | − | − | − | − | − | − | − | − | + |

b

| | 1 | 2 |
|---|---|---|
| CMV:β-arrestin-TEV | + | + |
| EF1α-V1:β-arrestin-TEV | – | + |
| CMV:ADRB2-tTA | + | – |
| EF1α-V1::ADRB2-tTA | – | + |

C

METHOD FOR TRANSDUCING PROTEIN-PROTEIN INTERACTIONS

CROSS-REFERENCE TO RELATED APPLICATIONS

The present application is the US National Stage of International Patent Application No. PCT/EP2019/077962 submitted Oct. 15, 2019, which claims benefit of the priority of European patent application EP18200357.4 submitted Oct. 15, 2018, which is incorporated herein by reference.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Apr. 15, 2021, is named "95083_315_29_seqlist.txt" and is 42,293 bytes in size.

FIELD

The present invention relates to methods and means for assessing or responding to a protein-protein interaction and transducing this interaction to the expression of a gene of interest.

BACKGROUND OF THE INVENTION

Molecular interactions, such as protein/protein interactions, are involved in almost every cellular process in living cells. The characterization of a protein/protein interaction is an important step to better understand and control biological systems. The transduction of a protein/protein interaction to a detectable signal or to expression of a gene of interest is important for the discovery of new drugs and the development of cells with new functions used as cell-based biosensors or cell therapies.

Different cellular pathways are modulated by the presence/absence of compounds that promote or inhibit a protein/protein interaction. The identification of molecules modulating protein/protein interaction is one of the main tools used in drug discovery and development. Further, transduction of a protein/protein interaction into a novel response is a major tool for cell engineering for therapeutic purposes.

An example of a protein interaction modulated by a compound is the interaction between G-protein coupled receptors (GPCRs) and downstream pathway proteins, such as beta-arrestin. GPCRs are membrane receptor in mammalian cells that can detect various ligands (endogenous hormones, growth factors, and natural or synthetic small molecules). Following the interaction of the GPCR with its ligand, different cascades in the cells are induced, modulating cellular activity. Due to the central function of the GPCR in the cells, many drugs act on GPCRs as their targets. Different assays have been developed to identify and characterize GPCR agonists and antagonists. Some of these assays transduce the interaction of the GPCR with one of its protein partners into the expression of a reporter gene.

In addition, protein/protein interactions have been used to design chimeric sensors which can sense different signals and transduce these signals to a specific response. This ability to redirect information from defined input to specific output can be used for numerous applications such as the generation of cell-based biosensors to produce new in vitro diagnostic tools or to generate new cell therapies with better safety and efficacy. Despite numerous developments in the area of biosensors, many of them merely generate a detectable signal that requires manual readout and interpretation by a human. Significantly less progress has been made on biosensors that transduce a signal into a downstream biological activity, such as gene expression. Artificial signal transduction systems described so far mainly utilize an act of cleavage of a fusion protein to release a transcriptional activator, which then modulates the expression of a gene of interest.

The two-component system (TCS) signalling cascade is initiated upon ligand-triggered autophosphorylation of the histidine kinase (HK) receptor protein at the histidine residue, followed by phosphoryl transfer to the aspartate residue of a Response Regulator (RR) protein. With a few exceptions, a HK sensor forms a homodimer in the cell membrane, and the structural basis of HK autophosphorylation is the existence of two distinct HK dimer conformations. In the unstimulated state, the conformation is such that the catalytic ATP-binding (CA) domain is distant from the histidine residue in the dimerization and histidine-containing phosphotransfer (DHp) domain (FIG. 1*a*), therefore autophosphorylation does not take place. Upon ligand binding, the CA domain and the bound ATP get into close proximity of the histidine of the DHp, enabling phosphoryl transfer. Next, a cognate response regulator (RR) binds to the phosphorylated DHp domain, the phosphate is transferred from the histidine to one aspartate in the receiver domain of the RR, and the phosphorylated RR binds to its target promoters and regulates gene expression. In addition, when a phosphorylated RR binds to the unphosphorylated DHp domain, the latter catalyses dephosphorylation of the aspartate residue and thus, actively shuts down the signalling. Accordingly, an HK is a bifunctional enzyme with kinase and phosphatase activities, and the balance between the two determines signalling intensity and dynamics.

Due to the importance of the GPCR signaling in human disease, different assays have been developed to detect and identify molecules that interact with GPCRs. Among the different methods developed, some take advantage of the fact that beta-arrestin interacts with ligand-activated GPCR. The bioluminescence resonance energy transfer (BRET) assay, the TANGO assay (Invitrogen) (FIG. 5) and the ChaCha system are examples of these assays. The first system transduces protein/protein interaction into detectable fluorescent signal. The two latter assays transduce protein/protein interactions to the expression of a gene of interest, such as a reporter gene.

The TANGO assay is implemented by fusing to the intracellular domains of GPCR a proteo-lytically cleavable artificial transcription factor (GAL4-VP16) and by fusing a TEV protease to beta-arrestin. The activation of the GPCR by a ligand induces the recruitment of the beta-arrestin to the GPCR, bringing the TEV protease in close proximity of the cleavable linker on the GPCR, and allowing the release of GAL4-VP16. The artificial transcription factor will induce the expression of the reporter gene (beta-lactamase) driven by a chimeric promoter targeted by GAL4-VP16.

The ChaCha system has been recently developed as a derivative of the TANGO assay. In this system dCas9 (unable to cut DNA but still able to bind it) linked to a tripartite transcriptional activator composed of VP64, p65 activation domain, and Rta (dCas9-VPR) is fused to beta-arrestin while the intracellular domains of GPCR is fused to the TEV protease. This system also requires the expression of a guide RNA (gRNA), which allows dCas9 to be recruited to the promoter driving the expression of the gene of interest. The interaction between the GPCR and the beta-arrestin-dCas9-VRP fusion releases the dCas9-VRP. The dCas9-VRP modulates the expression of gene of interest targeted by the gRNA co-expressed in the cell. The promoter can be an endogenous or a chimeric one.

With respect to probing generic protein-protein interactions e.g., in the cytoplasm, different methods have been developed as well. One of the most popular is the yeast two hybrid approach. In this method, two potential interacting proteins, usually called bait and prey, are fused to split subunits of a protein with a particular detectable biological activity. Each of the split subunits alone do not show the biological activity in question. The interaction between the bait and the prey allows proper reconstitution of the domains fused to the bait and the prey, respectively. Different reporter systems have been developed depending of the localization of the bait and the prey:

- for probing nuclear localization, the split protein reconstitutes transcriptional activation of a reporter gene;
- for protein-protein interactions that take place in the cytoplasm or at the membrane, the reporter system is based on growth of the yeast by activating Ras signaling, uracil auxotrophy, or antibiotic resistance.

One drawback of the yeast-two-hybrid approach is the fact that the interaction is quantified in the yeast cells and they may not faithfully recapitulate the interaction in the native mammalian cell milieu.

Accordingly, it is the objective of the invention to provide means and methods for responding to and/or assessing protein-protein interactions.

DESCRIPTION OF THE INVENTION

This objective is solved by a cell and the methods specified in the independent claims. Advantageous embodiments are stated in the dependent claims and the following description.

A first aspect of the invention relates to a recombinant cell. The cell facilitates analysis of the interaction of a pair two polypeptides or proteins with one another. These interaction partners are termed in the following “first polypeptide” and “second polypeptide”. Each of these polypeptides is encoded by a nucleic acid sequence and each of these polypeptides is part of a fusion protein comprising the polypeptide part subject to analysis of its interaction with the other polypeptide, and a fragment of a histidine kinase variant that retains DHp and CA activity.

The cell according to the invention comprises

- a first nucleic acid sequence encoding a first polypeptide fused to the N-terminus of a first variant of a histidine kinase (E.C. 2.7.13.3). The histidine kinase comprises a DHp (dimerization and histidine-containing phosphotransfer) domain and a CA (catalytic ATP-binding) domain. The cell further comprises
- a second nucleic acid sequence encoding a second polypeptide fused to the N-terminus of a second variant of a histidine kinase comprising a DHp domain and a CA domain, and
- a third nucleic acid sequence encoding a response regulatory protein specifically phophorylatable by the DHp domain of the first or said second variant of the histidine kinase.

In other words, this aspect of the invention relates to a cell that comprises

- a first nucleic acid sequence, wherein the first nucleic acid sequence encodes
  - in orientation from N to C, a first polypeptide, interaction of which with a second polypeptide is subject of analysis, fused to the N-terminus of a first variant of a histidine kinase, wherein the histidine kinase comprises a DHp domain and a CA domain and both DHp domain and CA domain are retained in the first variant,
- a second nucleic acid sequence encoding a second polypeptide fused to the N-terminus of a second variant of said histidine kinase comprising a DHp domain and a CA domain, wherein both DHp domain and CA domain are retained in the second variant also, and
- a third nucleic acid sequence encoding a response regulatory protein specifically phosphorylatable by said DHp domain of said first or said second variant.

In particular embodiments, the first and the second polypeptide do not comprise any part of the above mentioned histidine kinase, particularly not the transmembrane domain, the sensor domain or the transmitter domain.

In certain embodiments of the cell of the invention, the first variant and/or the second variant does not comprise a transmembrane domain of the histidine kinase.

In certain embodiments of the cell of the invention,

- said first variant does not comprise a functional transmitter domain and/or a functional sensor domain of the histidine kinase, and/or;
- said second variant does not comprise a function transmitter domain and/or a functional sensor domain of the histidine kinase.

In particular embodiments, the naturally occurring sensor and transmitter domain of the histidine kinase are replaced by two proteins of interest, the interaction of which shall be assessed. If there is a specific interaction between these proteins, binding between them facilitates the dimerization of the truncated variants of the histidine kinase, by which a spatial proximity of the CA domain having an ATP and the DHp domain is achieved. This yields a phosphorylation of the DHp domain, which then is able to phosphorylate a cognate ligand, the response regulatory domain, particularly a receiver domain of the response regulatory protein.

Alternatively, the two proteins of interest may form an artificial signal transduction pathway, wherein binding of the two proteins of interest is triggered by a stimulus, such as a ligand being specifically recognizable by the one of or both of the two proteins of interest. Recognition of the ligand may be connected to a desired response mediated by the activity of the regulator response protein. Such response may be the expression of a microRNA affecting cellular processes of the cell, or a protein, such as a cytokine or an antibody. In particular embodiments, such cells may be used for medical applications, wherein beneficial or therapeutic responses may be specifically triggered by, for example, disease-related compounds such as disease related antigens.

Alternatively, the effect of compounds on known interacting proteins may be assessed by the cell of the invention, wherein the effect of the compounds may be determined by the activity of the regulatory response protein.

Particularly, the response regulatory protein comprises an effector function, which can be determined for assessing the interaction between the first polypeptide and the second polypeptide, or used to elicit a desired response in response to the above mentioned stimulus. Non-limiting examples of such effector function include binding to DNA, RNA or enzymes, for example enzymes catalyzing e.g. the formation of cAMP.

In particular embodiments, the effector function comprises the specific binding to a promoter sequence and induction of the expression of a gene of interest.

In certain embodiments of the cell of the invention, the response regulatory protein comprises a receiver domain fused to an effector domain, wherein the receiver domain is capable of being phosphorylated by the DHp domain of the first or the second histidine kinase variant, and the effector domain is capable of being modulated, particularly activated or inhibited, by the phosphorylated receiver domain. Particularly, the activity of the effector domain changes with respect to the phosphorylation state of the receiver domain, thus the activity of the effector domain can increase or can be switched on or decrease or be inhibited by phosphorylation of the receiver domain.

In certain embodiments of the cell of the invention,

- the effector domain is a transcriptional activating domain, and
- the cell comprises a fourth nucleic acid sequence comprising a gene of interest under control of an inducible promoter recognizable by the transcriptional activating domain, wherein upon activation of the transcriptional activating domain the expression of the gene of interest is induced.

In certain embodiments of the cell of the invention, the gene of interest encodes a protein of interest, particularly a fluorescent or a luminescent protein, or an RNA of interest.

Such protein of interest may be a fluorescent or a luminescent protein, whereby successful interaction between the first and second polypeptide may be determined or observed via the fluorescence or luminescence of the protein of interest.

Alternatively, the protein of interest or the RNA of interest may be or trigger the desired response in response to the above-mentioned stimulus, such as a desired therapeutic response (cytokine, antibody, production of reactive oxygene species, etc.).

In certain embodiments of the cell of the invention,

- the first and the second variant are variants of the EnvZ kinase (UniProt No POAEJ4), the response regulatory protein comprises or a is the OmpR response regulatory (RR) protein (Uniprot No P0AA16), or
- the first and the second variant are variants of the NarX kinase (UniProt No POAFA2), the receiver domain comprises or a is the NarL response regulatory (RR) protein (Uniprot No. P0AF28), and the effector domain is or comprises a VP1.6 transcriptional activating domain (Vp48, SEQ ID 7).

As indicated previously, the effector domain can be part of NarL fused with the VP16.

In certain embodiments of the cell of the invention, the transcriptional activating domain is, consists of or comprises an amino acid characterized by SEQ ID NO 7.

In certain embodiments of the cell of the invention, the first or the second variant is or comprises a variant selected from $EnvZ^{180 to 450}$(SEQ ID 8), $EnvZ^{223 to 450}$ (SEQ ID 9), $NarX^{176 to 598}$ (SEQ ID 10) and $NarX^{379 to 598}$ (SEQ ID 11) or a functional equivalent polypeptide having a sequence identity of at least 70%, 80%, 85%, 90%, 95%, 98% or 99% to any one of SEQ ID 8 to 11.

In certain embodiments of the cell of the invention, the inducible promoter is selected from the OmpR promoter (SEQ ID 1) and the NarL-RE promoter (SEQ ID 2).

In certain embodiments of the cell of the invention, the first nucleic acid sequence and/or the second nucleic acid sequence and/or the third nucleic acid sequence is optimized towards the codon usage of the cell.

In certain embodiments of the cell of the invention, the first nucleic acid sequence and/or the second nucleic acid sequence and/or the third nucleic acid sequence is under transcriptional control of a constitutive promoter.

In certain embodiments of the cell of the invention, the constitutive promoter is selected from CMV (SEQ ID 3), EF1α (SEQ ID 4), and EF1α-V1 (SEQ ID 5).

In certain embodiments of the cell of the invention, the first variant and the second variant are identical.

In certain embodiments of the cell of the invention, the histidine kinase belongs to the transphosphorylation family.

In certain embodiments of the cell of the invention,

- the first variant comprises a DHp domain that does not comprise a histidine residue accessible by the CA domain of first or the second variant of the histidine kinase, and/or
- the second variant comprises a CA domain that is not able to bind ATP.

In certain embodiments of the cell of the invention,

- the first variant is or comprises variant $NarX^{379-598}$ (H399Q) (SEQ ID 12) or a functional equivalent polypeptide having a sequence identity of at least 70%, 80%, 85%, 90%, 95%, 98% or 99% to (SEQ ID 12), and/or
- the second variant is or comprises variant $NarX^{379-598}$ (N509A) (SEQ ID 13) or a functional equivalent polypeptide having a sequence identity of at least 70%, 80%, 85%, 90%, 95%, 98% or 99% to (SEQ ID 13).

In certain embodiments of the cell of the invention, specific binding of the first polypeptide and the second polypeptide is triggerable by a ligand specifically recognizable by the first and/or the second polypeptide.

In certain embodiments of the cell of the invention, the first polypeptide is or comprises a receptor and the second polypeptide is or comprises a binding partner of the receptor, wherein binding of the receptor and the binding partner is triggerable by the ligand recognizable by the receptor.

In certain embodiments of the cell of the invention, the receptor is a transmembrane receptor, and the binding partner is a cytosolic protein. In this case, the ligand recognizable by the receptor and the cytosolic protein as binding partner are particularly separated by a membrane.

In certain embodiments of the cell of the invention,

- the first polypeptide consists of or comprises a G-protein coupled receptor and the second polypeptide consists of or comprises a cytosolic ligand of the G-protein coupled receptor, particularly beta-arrestin, or
- said first polypeptide consists of or comprises a T cell receptor or one of its components and the second polypeptide is or comprises a cytosolic ligand of the T cell receptor or its component, particularly ZAP-70 (UniProt No P43403).

In certain embodiments of the cell of the invention, the cell is a mammalian cell, particularly a human cell.

Another aspect of the invention relates to a method for assessing a protein-protein interaction. The method comprises:

- providing a cell according to the invention, the cell comprising:
  - a first nucleic acid sequence encoding a first polypeptide fused to the N-terminus of a first variant of a histidine kinase (E.C. 2.7.13.3) comprising a DHp domain and a CA domain,
  - a second nucleic acid sequence encoding a second polypeptide fused to the N-terminus of a second variant of the histidine kinase comprising a DHp domain and a CA domain, and a third nucleic acid sequence encoding a response regulator protein specifically phosphorylatable by the DHp domain of the first or the second variant; and determining the activity of the response regulatory (RR) protein, wherein upon specific binding of the first polypeptide and the second polypeptide the first and second variant dimerize such that the CA domain of the first or second variant phosphorylates the DHp domain of the first or second variant, and the activity of the response regulatory protein is modulated, particularly activated or inhibited, by its phosphorylation by the DHp domain of the first or second variant.

A further aspect of the invention relates to a method for assessing the effect of a compound on a protein-protein interaction. The method comprises the steps of:

providing a cell according to the invention, the cell comprising, a first nucleic acid sequence encoding a first polypeptide fused to the N-terminus of a first variant of a histidine kinase comprising a DHp domain and a CA domain, a second nucleic acid sequence encoding a second polypeptide fused to the N-terminus of a second variant of said histidine kinase comprising a DHp domain and a CA domain, and a third nucleic acid sequence encoding a response regulatory protein specifically phosphorylatable by said DHp domain of said first or said second variant, and contacting the cell with a compound, and determining the activity of said response regulatory protein, wherein upon specific binding of the first polypeptide and the second polypeptide the first and second variant dimerize such that the CA domain of the first or second variant phosphorylates the DHp domain of the first or second variant, and the activity of said response regulatory protein is modulated, particularly activated or inhibited, by phosphorylation by said DHp domain of said first and/or second variant, and the effect of the compound on the specific binding of the first polypeptide and the second polypeptide is determined by the activity of the response regulator protein.

Advantageously, the above method may be used as a screening assay to assess the effect of any compound on any interesting protein-protein interaction.

Yet another aspect of the invention provides a method for for eliciting a desired response in response to a stimulus. The method according to this aspect of the invention comprises the steps of:

providing a cell according to the invention, the cell comprising, a first nucleic acid sequence encoding a first polypeptide fused to the N-terminus of a first variant of a histidine kinase comprising a DHp domain and a CA domain, a second nucleic acid sequence encoding a second polypeptide fused to the N-terminus of a second variant of the histidine kinase comprising a DHp domain and a CA domain, wherein specific binding of the first and second polypeptide is triggered by the stimulus, and a third nucleic acid sequence encoding a response regulatory protein specifically phosphorylatable by the DHp domain of the first or the second variant, wherein upon specific binding of the first polypeptide and the second polypeptide, the first and the second variant dimerize such that the CA domain of the first or the second variant phosphorylates the DHp domain of the first or second variant, and the activity of the response regulatory protein is modulated, particularly activated or inhibited, by phosphorylation by the DHp domain of the first and/or the second variant, and exposing the cell to the stimulus, wherein the desired response is mediated by or is the activity of the response regulatory protein.

Preferably, the first or second polypeptide is a receptor recognizing the stimulus, for example a T cell receptor recognizing a disease related antigen, or a G-coupled receptor, wherein the other polypeptide may be a ligand of this receptor, such as beta-arrestin or ZAP-70, respectively.

The term "specific binding of the first and second polypeptide" particularly refers to a binding with a Kd of less than $10^{-5}$ M $10^{-6}$ M, $10^{-7}$M, $10^{-8}$ M, or $10^{-9}$ M.

In certain embodiments of the methods of the invention, the response regulatory protein comprises a receiver domain fused to an effector domain, wherein the receiver domain is phosphorylatable by the DHp domain of the first or the second variant, and the effector domain is activatable by the phosphorylated receiver domain.

In certain embodiments of the method of the invention, the response regulatory protein comprises a receiver domain fused to an effector domain, wherein the receiver domain is phosphorylatable by the DHp domain of the first or the second variant, and the effector domain is activatable by the phosphorylated receiver domain;

the effector domain is a transcriptional activating domain, the cell further comprises a fourth nucleic acid sequence encoding a gene of interest under control of an inducible promoter recognizable by said transcriptional activating domain, wherein upon activation of the transcriptional activating domain, the expression of the gene of interest is induced.

In certain embodiments of the methods of the invention, the presence of the expression product of the gene of interest is determined as the activity of the response regulatory protein.

In certain embodiments of the method of the invention, the expression product of the gene of interest has an optical quality, e.g. comprises a luminescent moiety, like in the case of the green fluorescent protein (GFP).

In certain embodiments of the methods of the invention, the expression product of the gene of interest is Cerulean.

In certain embodiments of the methods of the invention, the expression product of the gene of interest is or mediates the desired response. For example, the expression product may be a cytokine intended to elicit an immune response by the cell. The expression product may also be a component of a signal cascade eliciting the desired response further downstream of the cascade. The expression product may also be an RNA able to elicit the desired response, such as such as a microRNA or a guide RNA that itself regulate endogenous genes.

Furthermore, the invention provides a vector that is particularly suitable for transfecting or transducing a mammalian cell, particularly a human cell. The vector comprises:

the first nucleic acid sequence as comprised within the cell of the invention, the second nucleic acid sequence as comprised within the cell of the invention, the third nucleic acid sequence as comprised within the cell of the invention, and optionally the fourth nucleic acid sequence as comprised within the cell of the invention.

According to a further aspect of the invention, a fusion protein is provided. The variant comprises a polypeptide fused to a variant of a histidine kinase (E.C. 2.7.13.3) comprising a DHp (dimerization and histidine-containing phosphotransfer) domain and a CA (catalytic ATP-binding) domain.

Particularly, the polypeptide does not comprise any part of the above-mentioned histidine kinase, particularly not the transmembrane domain, the sensor domain or the transmitter domain.

In certain embodiments of the fusion protein of the invention, the variant does not comprise a transmembrane domain of the histidine kinase.

In certain embodiments of the fusion protein of the invention, the variant does not comprise a functional transmitter domain and/or a functional sensor domain of the histidine kinase.

In certain embodiments of the fusion protein of the invention, the variant is a variant of the EnvZ kinase (UniProt No POAEJ4) or a variant of of the NarX kinase (UniProt No POAFA2).

In certain embodiments of the fusion protein of the invention, the variant is or comprises a variant selected from $EnvZ^{180to450}$ (SEQ ID 8), $EnvZ^{223to450}$ (SEQ ID 9), $NarX^{176to598}$ (SEQ ID 10) and $NarX^{379to598}$ (SEQ ID 11) or a functional equivalent polypeptide having a sequence identity of at least 70%, 80%, 85%, 90%, 95%, 98% or 99% to any one of SEQ ID 8 to 11.

In certain embodiments of the fusion protein of the invention, the histidine kinase belongs to the transphosphorylation family.

In certain embodiments of the fusion protein of the invention, the variant comprises a DHp domain that does not comprise a histidine residue accessible by the CA domain of the variant or another variant of the histidine kinase or comprises a CA domain that is not able to bind ATP.

In certain embodiments of the fusion protein of the invention, the variant is or comprises variant $NarX^{379-598}$ (H399Q) (SEQ ID 12), variant $NarX^{379-598}$ (N509A) (SEQ ID 13) or a functional equivalent polypeptide having a sequence identity of at least 70%, 80%, 85%, 90%, 95%, 98% or 99% to SEQ ID 12 or 13.

In certain embodiments of the fusion protein of the invention, the polypeptide consists of or comprises a G-protein coupled receptor or a cytosolic ligand of the G-protein coupled receptor, particularly beta-arrestin.

In certain embodiments of the fusion protein of the invention, the polypeptide comprises a T cell receptor or one of its components or a cytosolic ligand of the T cell receptor or its component, particularly ZAP-70 (UniProt No P43403).

The invention is further illustrated by the following examples and figures, from which further embodiments and advantages can be drawn. These examples are meant to illustrate the invention but not to limit its scope.

DETAILED DESCRIPTION OF CERTAIN EMBODIMENTS OF THE INVENTION

Figure 1A:
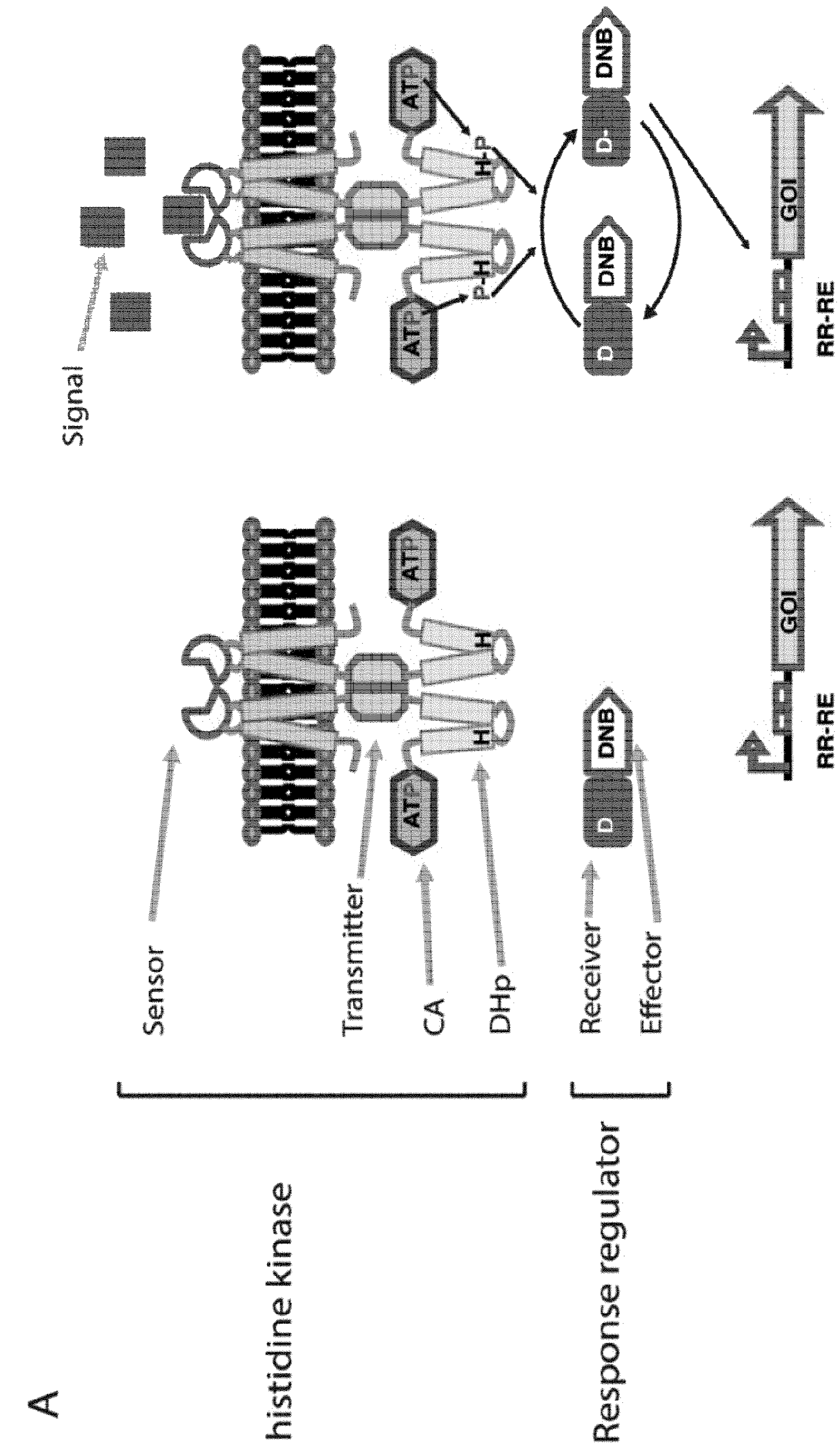
FIG. 1 shows schematics of native and transplanted two-component signaling pathways. (A) The native pathway consists of a receptor histidine kinase (HK) protein, which in presence of its signal would autophosphorylate and phosphorylate its cognate response regulator (RR) at the level of one asparagine present in the receiver domain. The phosphorylated RR would bind the specific response element present in promoter regulated by the RR. (B) The transplanted TCS in mammalian host are expressed from genes with human-optimized codon sequence. The histidine kinase transplanted in mammalian cell are always active and autophosphorylate and phosphorylate the RR. The transplanted RR are augmented with VP48 trans activating domain. The phosphorylated RR will bind the RE present in the engineered promoter that drives the expression of the gene of interest, in this case the fluorescent reporter cerulean. DNB, DNA binding domain. VP48, VP48 transactivator domain; Pmin, minimal mammalian promoter.

The present invention provides a novel approach to transduce protein/protein interactions into gene expression in mammalian cells using components derived from the two-component system present in bacteria. The invention can be used to develop new screening assay for protein-protein interactions in general, and for GPCR signaling modulation in particular. The herein described system is characterized by superior dynamic range compared to the state of the art (e.g., the TANGO system from ThermoFischer), and it has great potential for high-throughput multiplexing thanks to an almost unlimited supply of the building blocks.

The present invention may provide the basis of a synthetic signal transduction module in cell-based biosensors and engineered therapeutic cells, with such properties as low background levels, high dynamic range, and reversibility. As the approach can be multiplexed, it will allow the creation of complex logic-based circuits which could provide novel capabilities to the modified cell.

Particularly, the present invention comprises 3 different features:

- the HK (histidine kinase) component (split into two different mutants)
- the RR component
- the genetic construct containing the chimeric promoter allowing the expression of the gene of interest.

The HK domains fused to the 2 interacting proteins are mutated to increase the dynamic range. Wild-type domains can also be used, but so far this resulted in lower dynamic range. Nevertheless, the use of the wild type domain can confer some advantages when the system is used to detect homodimerization. In addition, in case of homodimerization of a protein of interest, HK belonging to the cis family can be used. The advantage of this approach is the reduction in the number of genetic constructs. Nevertheless, in all cases the important feature of the invention is the fusion of the protein of interest to a size-reduced domain of the HK that does not dimerize on its own and therefore does not transduce transcriptional activity on its own, unless forced to dimerize with the help of the fused components.

The RR (response regulator protein) used in this experiment is fused with VP48 as transcriptional activating domain functional in mammalian cells. Other transcriptional activating domains could be fused to the RR, for example p65 (RelA) domain or Rta. In the present examples, the inventors used RR that binds directly to DNA, but other types of RR can be used depending of the desired readout. For example, some RR can bind to RNA and others are enzymes, catalyzing the production of a compound feeding into a secondary signal transduction chain, e.g., cyclic di-GMP.

The gene construct expressing the gene of interest (GOI) comprises 2 elements. The first part is a chimeric promoter. The inventors used a minimal promoter linked to an upstream sequence with a number of binding sites for the RR. The distance between the minimal promoter and the number of RE can be modified to tune the expression of the GOI, either up- or down.

The GOI used in the experiment is a fluorescent reporter Cerulean but this can be replaced with any other protein- or RNA-coding gene. For example, GOI could be a miRNA or guide RNA that itself can regulate endogenous genes.

The present invention differs from the aforementioned systems TANGO and ChaCha in that these systems release the transcription factor previously fused, respectively, to the GPCR or beta-arrestin, and this transcription factor accumulates over time. On the contrary, in the present invention, all the elements are still functional after one act of protein-protein interaction and therefore they exhibit multiple turnover. The gene of interest modulated by both the TANGO and the system of the invention is under the regulation of a chimeric promoter. In the ChaCha system, endogenous genes can also be modulated using appropriately designed gRNA. Another difference between this invention and the TANGO assay is that in this invention, one needs an additional component, namely, the RR in addition to the chimeric GPCR fusion and beta-arrestin fusion.

The size of the HK domains fused to the GPCR and to the beta-arrestin are only 223 aa. In the TANGO the size of the fused proteins is 240 aa and 341 aa, respectively. For the ChaCha they are 240 aa and 1900 aa, respectively, in addition to the requirement for gRNA expression. Due to this smaller size the system is easier to construct and it places less burden on the cells.

The system of the invention contains two signal amplification steps. The first step, unique to the invention, results from the reconstituted HK which phosphorylates multiple copies of the RR. The second level of amplification, also present in the TANGO and ChaCha system, is the catalytic nature of gene induction by the RR. Two levels of amplification in the present invention result in a 10-fold improvement in the dynamic range compared to the TANGO system.

The system of the invention is not desensitized in the course of time; the same protein can be re-activated after several cycles of presence/absence of ligand. On the contrary, the elements of the TANGO and ChaCha system can only be used once and therefore their system activity relies on the protein degradation and de novo protein synthesis, an inherently slow process. This characteristic lets the system of the invention switch more rapidly from On state to Off and vice versa.

Due to the fact that the present invention contains one extra level of amplification compared to the other approaches, it can detect low amounts of protein and weak protein-protein interactions. The advantage of this feature is that the expression of the components needed for the assay of the invention can be modulated in the cells from low to high. In this way, the level of expression of the system components can be set at a level that enables an appropriate ligand-inducible dynamic range. Therefore, the present approach reduces ligand-independent signalling that can occur due to protein overexpression in the earlier approaches.

Specifically, the assay of the invention shows higher dynamic range than the TANGO assay. This parameter would facilitate the automated analysis of the result generated by the present invention compared to the TANGO.

Another advantage of the system of the invention is that it can be multiplexed by employing different HK-RR pairs simultaneously. Due to the very large number of natural two-component systems, the potential to multiplex is very large. Each chimeric pair would be independent and induce a different output. Therefore, in the same experiment one will be able to test the effect of a compound on multiple protein-protein interactions or multiple GPCRs at once. Multiplexing is more difficult with other approaches because the number of well characterized TEV proteases is limited.

The system of the invention also enables reversibility due to the fact that the RR spontaneously dephosphorylates. In the absence of the interaction between protein pairs, the kinase is not active anymore and does not phosphorylate the RR. The unphosphorylated RR cannot induce the expression of the GOI. In the case of the TANGO and ChaCha, the reversibility of the system is difficult because it requires time-consuming degradation of the transcriptional activator released after the interaction between the GPCR and beta-arrestin.

Lastly, the assay of the invention is highly modular. The same pair of complementing HK fragments can be utilized to detect a protein-protein interaction in the cytoplasm and membrane-localized protein-protein interaction, as in the case of GPCR induction assay. Other assays require big adjustments for probing different types of protein-protein interaction, and assays such as TANGO are specific to GPCR pathways and have not been used to probe generic protein-protein interaction.

The present invention can have multiple applications.

1) It can be used for the development of a new screening assay for the identification of compounds interacting with a GPCR. The resulting assay is expected to have better specificity and a higher dynamic range than the existing ones. It will also be easier to multiplex. The commercialization of the assays can be done by selling stable cell lines containing the GPCR fused to the HK, similar to what is currently done by DiscoverX and ThermoFischer (PathHunter and the TANGO).

2) It can be used to screen for compounds modulating protein-protein interactions and therefore for drug discovery. As opposed to the yeast 2 hybrid, the screening assays could be done in mammalian cells, which is a more relevant system. In addition, with the present invention, the same assay can be used for proteins localized to different cell compartments (nucleus, cytoplasm or at the membrane).

3) Existing therapeutic cell-based agents often use signaling pathways that involve protein-protein interactions at the cytoplasmic side of the membrane. This includes CAR-T cells where the binding of the antigen to the extracellular antibody fragment recruits protein interaction partners; these interactions can then be rewired to result in therapeutic effects using the inventors' approach.

EXAMPLES

It is known that intracellular cytoplasmic domains of HK are capable of dimerizing and autophosphorylating.

Figure 1B:
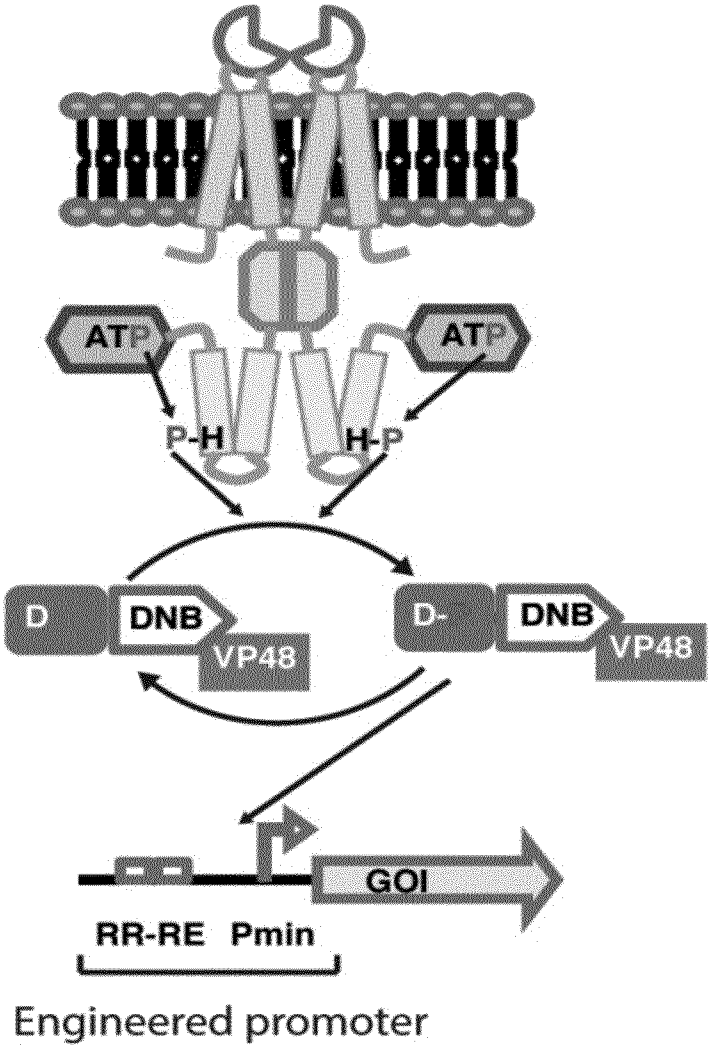

The present invention is based on the question whether partial cytoplasmic domains have a reduced inherent capacity to signal. To this end, the inventors undertook stepwise truncation mutagenesis of the HKs to identify domains that fail to dimerize on their own (FIG. 1*b*). The first set of truncated mutants comprised the entire cytoplasmic domain of EnvZ and NarX (EnvZ$^{180to450}$ and NarX$^{176to598}$, respectively) and the second set featured deeper truncation, with the N-terminus about 20 amino acids (aa) upstream of the histidine (EnvZ$^{223to450}$ and NarX$^{379to598}$, respectively). The inventors found that the truncation mutants of EnvZ, coexpressed with the cognate response regulator OmpR in HEK293 cells, were able to signal constitutively and induce the expression of OmpR-regulated reporter mCerulean at a level comparable with the wild-type EnvZ (FIG. 1*c*). This result is consistent with the fact that a small EnvZ domain containing the histidine ("Domain A", aa 223-289) is responsible for homodimerization. On the other hand, truncated mutants of NarX showed size-dependent reduction in basal signalling in the presence of the cognate RR NarL and NarL-inducible reporter, reaching background levels with the shortest mutant, NarX$^{379to598}$ (FIG. 1*d*). A number of explanations were possible for this result, including (1) reduction in protein stability; (2) the decrease in the kinase activity and/or the increase in the phosphatase activity of the truncated mutant and (3) the inability of the mutant to dimerize on its own. Among these explanations, only the last one would support the eventual establishment of synthetic signalling. To check if forced dimerization would restore signalling, the inventors attempted to fuse the truncated NarX domain to a pair of proteins forming strong heterodimers in mammalian cells. The reasoning was if the dimerization alone was impaired, these same mutants, attached to proteins with strong affinity to each other, would dimerize and transduce the signal downstream.

SynZip1/SynZip2

Figure 6:
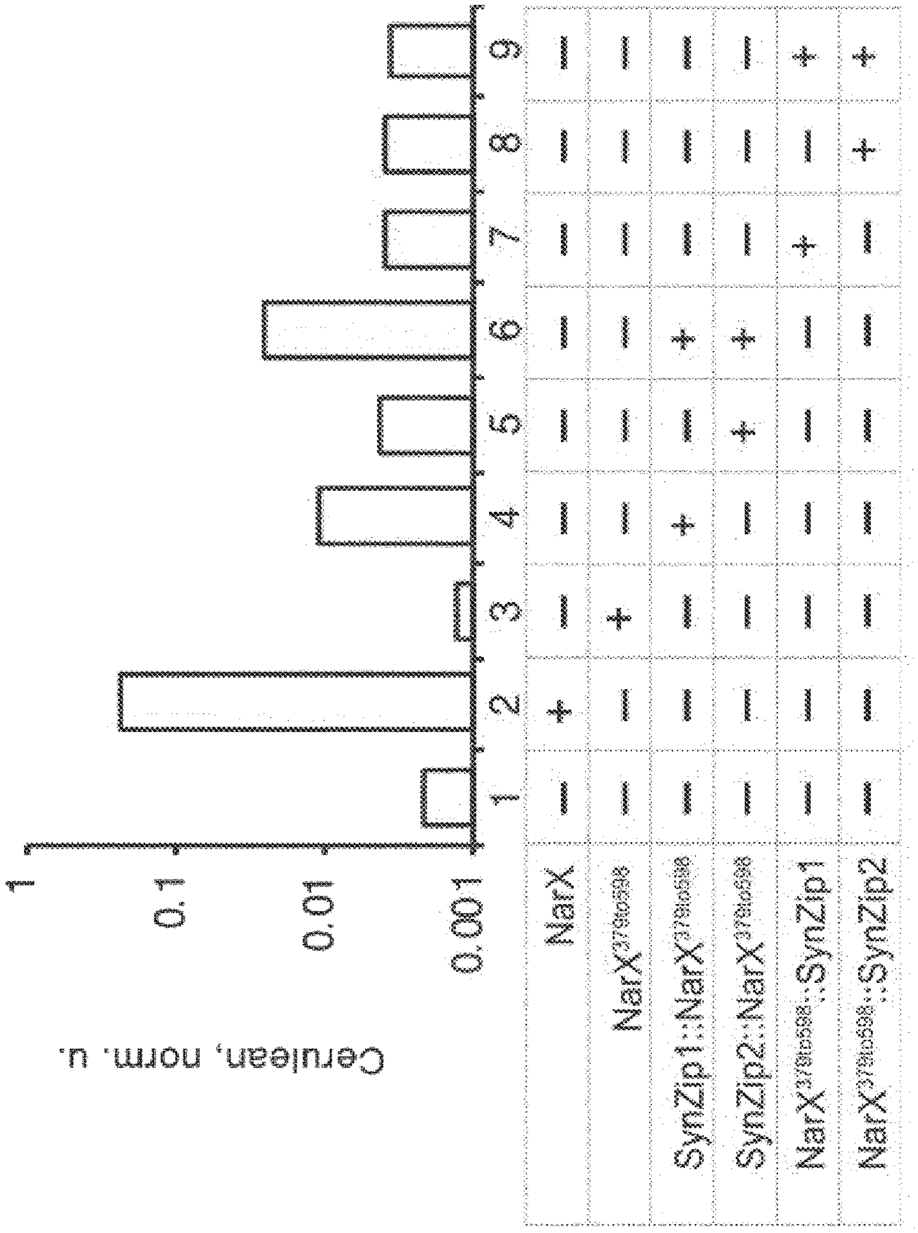
FIG. 6 shows the restoration of two-component signalling via forced dimerization of protein moieties fused at the C-terminus or at the N-terminus of NarX. Signalling levels in mammalian cells expressing the response regulator NarL and NarL-regulated mCerulean fluorescent protein reporter, alone or with different combinations of SynZip1 and SynZip2 fused at the C-terminus or at the N-terminus of NarX, as indicated in the chart. The bar charts display Cerulean level normalized to the expression of the transfection control in norm. u. as mean±SD of independent biological triplicates.
Figure 7:
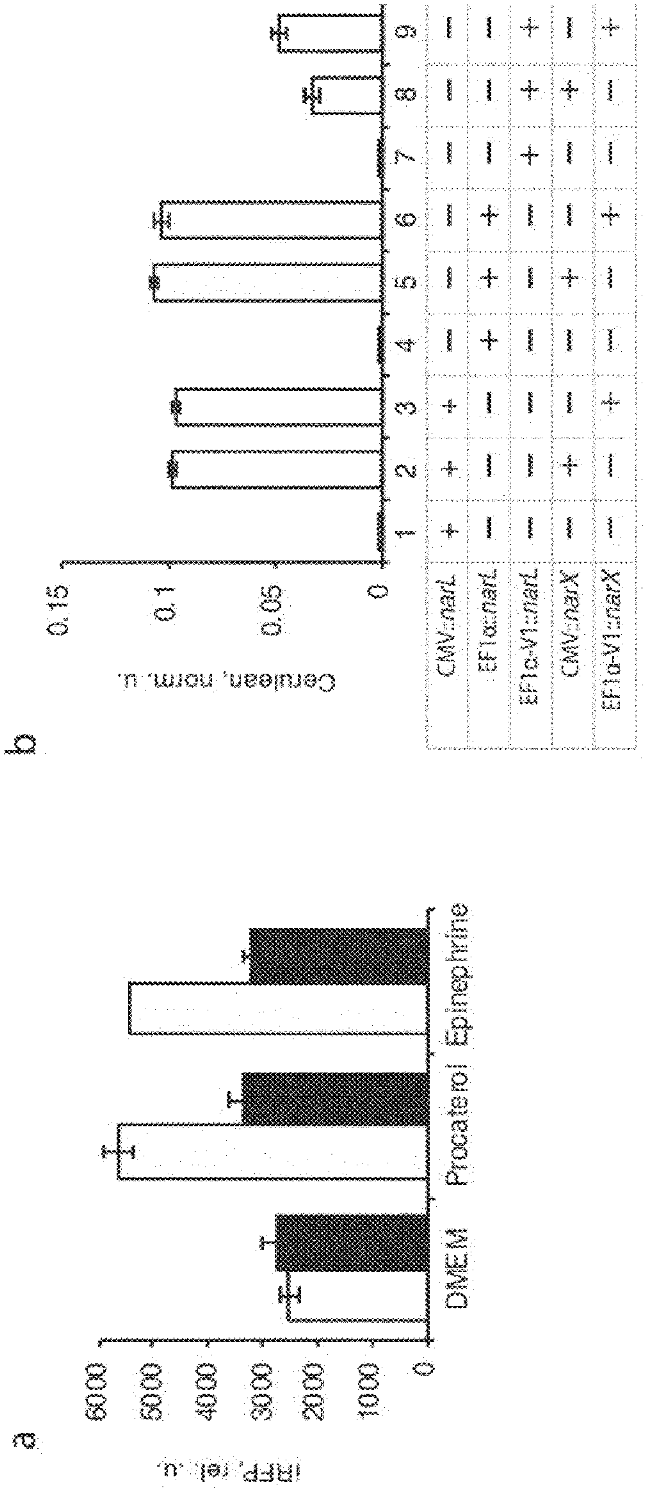
FIG. 7 shows the comparison of CMV and EF1α promoters. (a) iRFP fluorescence of HEK cells transfected with the plasmid expressing iRFP from the CMV promoter (white bar) or from the EF1α promoter (black bars). The reporter expression in DMEM without any ligand or in the presence of 1 μM of procaterol or 2 μM of epinephrine is shown as indicated. The bar charts display iRFP level normalized to the frequency of the transfection marker Citrine-positive cells (rel. u.) as mean±SD of independent biological triplicates. (b) Activity of the NarX/NarL expressed from CMV or EF1α promoters. Every transfection contains NarL-regulated mCerulean fluorescent protein reporter and plasmids expressing NarL and NarX from CMV, EF1α or EF1α-V1 promoters, as indicated in the chart. The bar chart displays Cerulean levels normalized to the expression of the transfection control in norm. u. as mean±SD of independent biological triplicates.

The inventors used a known interaction pair SynZip1 and SynZip2, and fused them to the N- and the C-termini of the short NarX domain NarX$^{379to598}$. It was observed (FIG. 6) that coexpression of SynZip1 and SynZip2 fusions to the N-terminus of the short NarX domain resulted in an increased reporter expression, although the expression was much lower than the signalling of the full-length NarX. On the other hand, coexpression of SynZip fusions to the C-terminus of NarX did not result in any dimerization-triggered increase reporter expression. Overall, the result hinted at the possibility of forced dimerization as a signalling mechanism via fusion to the N-terminus of the short cytoplasmic NarX domain, consistent with the position of the sensor domain relative to the cytoplasmic domain in the full-length HK. However, the quantitative behaviour was poor. In parallel to this study, the inventors optimized the promoters driving their constructs to make sure they do not respond to external stimulation and that the expression levels are balanced (FIG. 7).

For any synthetic signalling system, it is important to avoid non-specific changes to the signalling readout. In the system of the invention, the components are expressed from constitutive promoters. However, these promoters are in fact controlled by highly-expressed transcription factors such as Sp1, and there is always a risk that these factors are directly affected by external stimuli via unrelated endogenous pathways. This would result in the change of constitutive expression, and apparent change in the signalling readout that is unrelated to the studied effect and is artefactual. To eliminate these confounding factors, the inventors examined a number of constitutive promoters for their robustness under various stimulation conditions and compared the expression of iRFP from the CMV and EF1α promoters in the presence of different compounds often used to induce cell signalling (Epinephrine and procaterol). In the medium without any compound, the activity of both promoters is similar. However, in presence of epinephrine and procaterol the activity of the CMV promoter is induced by a factor of two, while the activity of the EF1α promoter is not affected (FIG. 7*a*).

The activity of the NarX/NarL system expressed from CMV, EF1α, and EF1α-V1 promoters was quantified to determine whether a too-high expression of the truncated HK cytoplasmic domain would increase the background level and respond to non-specific interactions. The EF1α-V1 promoter is around 5 times weaker than EF1α. The results demonstrate that comparable expression of the reporter gene is obtained with NarX expressed from any of the tested promoter (FIG. 7*b*, compare lanes 2 and 3 and lanes 5 and 6). However, when NarL is expressed from the weaker promoter, a reduction in the expression of the reporter gene was observed (Supplementary FIG. 2*b*). In the light of these results, the inventors used EF1α-V1 to drive NarX-derived constructs and EF1α to drive NarL expression.

Figure 2A:
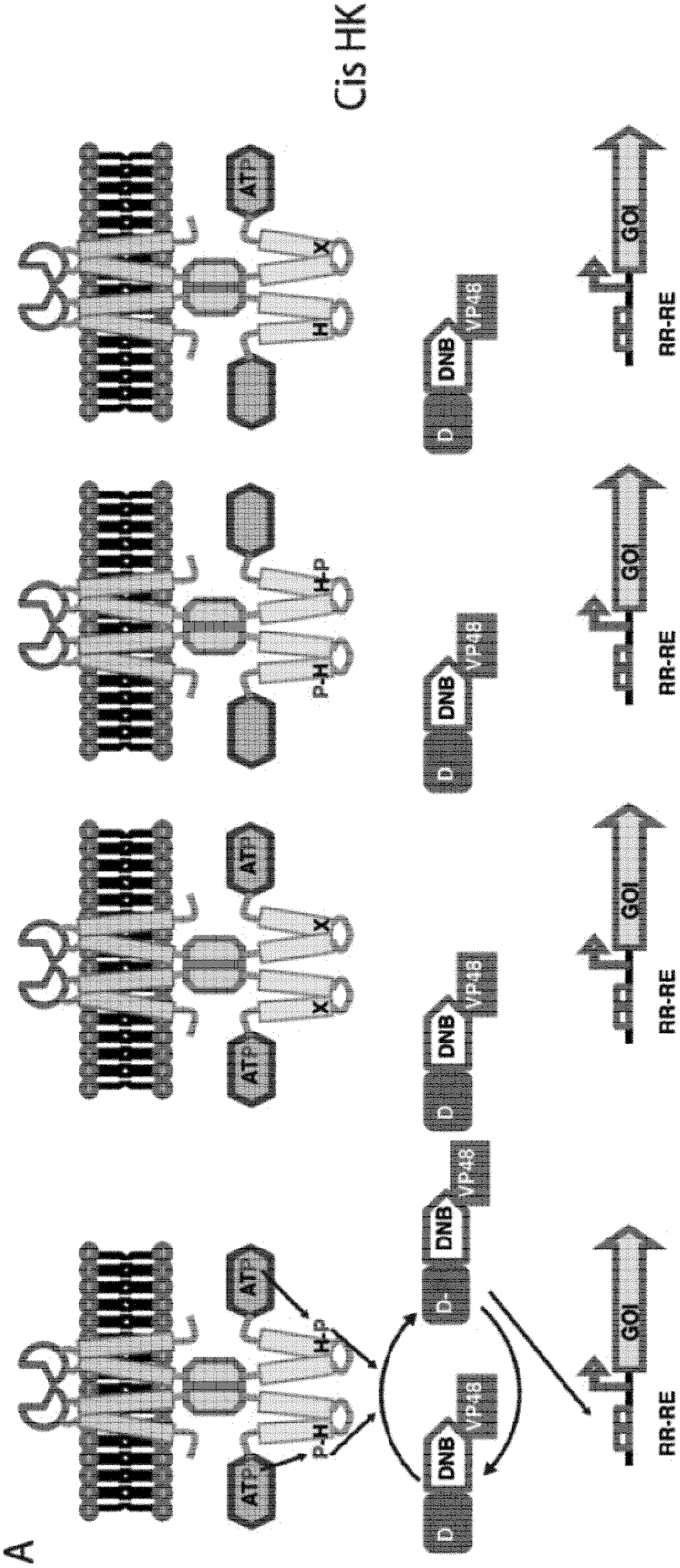
FIG. 2 shows Cis versus Trans autophosphorylation of the HK. (A) Schematics representation of the cis-autophsophorylation (the upper lane) and of the trans-autophosphorylation (lower lane) in mammalian cells expressing WT HK (first column), DHp mutant (second column), CA mutant (third column) or DHp mutant and CA mutant (fourth column). (B) Quantitative data for mammalian cells expressing the reporter gene alone or in combination with wild type HK, DHp mutant (EnvZ H243V, NarX H399Q and DcuS H350L), CA mutant (EnvZ N347A, NarX N509A and DcuS N445A) or DHp mutant and CA mutant. The bar charts display Cerulean level normalized to the expression of the transfection control in norm. u. as mean±SD of independent biological triplicates.
Figure 2:
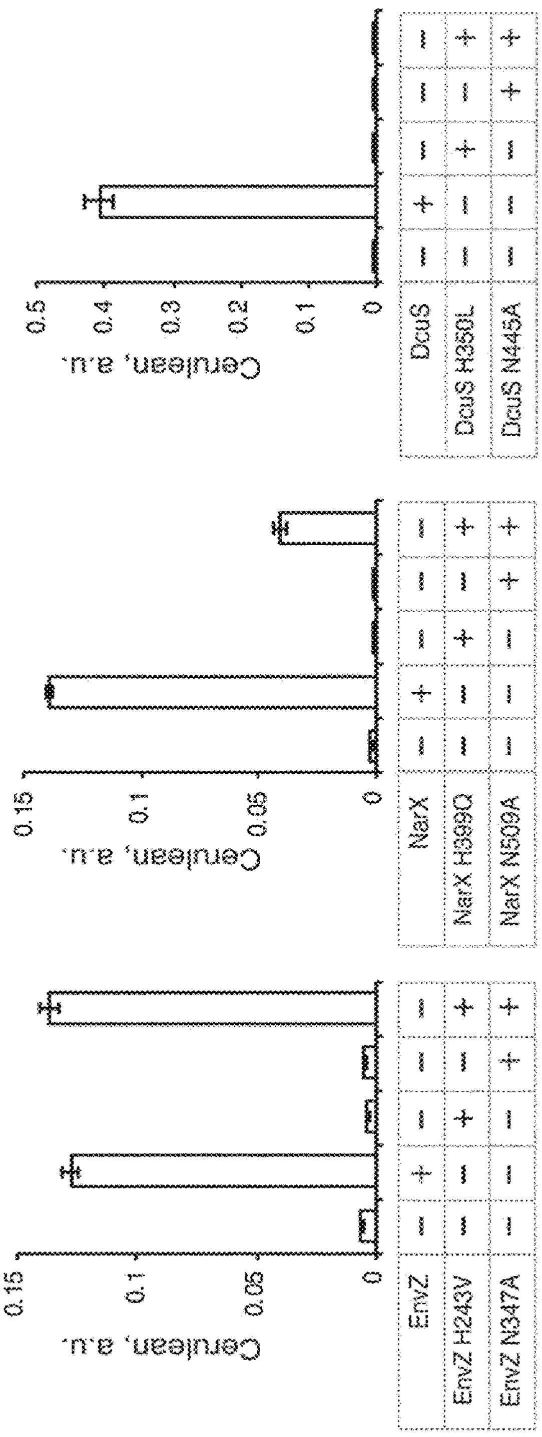

The inventors further explored possibilities to optimize the effect. It is known that the HKs can be divided into two families with respect to the autophosphorylation mechanism. In the "cis"-family, the phosphoryl group is transferred to the histidine from an ATP molecule bound to a CA domain of the same monomer. In the "trans"-family, the phosphoryl group is transferred from an ATP bound to one monomer to the phosphorylatable histidine in the other monomer (FIG. 2*a*). For all HKs, phosphoryl group transfer can be stopped by either mutating the ATP binding site or the histidine. A heterodimer formed between an ATP binding site mutant and a histidine mutant would be incapable of signalling in the case of a "cis"-family HK, but in the case of a "trans"-family HK, it will in fact still be able to signal via unidirectional phosphate transfer from the histidine mutant monomer to the ATP-binding site mutant monomer (FIG. 2*b*). Therefore, the mutants complement each other for "trans"-family HKs.

The inventors hypothesized that dimerization between complementing mutants could result in a more efficient transduction due to reduced phosphatase activity of the mutant HK towards its cognate response regulator. Using protein alignment, the inventors identified the putative residues important for ATP binding in the CA domains of NarX.

Mutational analysis of the aa present in the CA domain of EnvZ had allowed to identify the asparagine in position 347 to be primordial for kinase activity of EnvZ. The CA domains of the histidine kinase belongs to the large family of the ATPase domain of HSP90 chaperone/DNA topoisomerase II/histidine kinase protein (Superfamily 55874, http://supfam.org/SUPERFAMILY/cgi-bin/scop.cgi?sunid=55874). To identify if the N347 of EnvZ is conserved in NarX, the inventors aligned EnvZ and NarX with proteins containing the ATPase domain. The alignment identified the Asn509 for NarX as a conserved residue that is potentially important for ATP binding.

Because the full-length HKs were shown to signal constitutively in the mammalian cells, the inventors set up the complementation assay in HEK293 cells by cotransfecting different combinations of codon-optimized mutants of the NarX together with the cognate downstream RR NarL and the reporter gene driven by NarL-responsive promoter. In this assay (FIG. 2*c*), it was shown that (i) the full-length wild-type NarX is able to signal as shown before; (ii) the mutants of either the aspartate in the CA domain important for ATP binding, or the histidine in the DHp domain, are unable to signal on their own, as expected; (iii) co-expression of the complementing mutants of NarX partially restores the signalling to the levels obtained with the wild-type NarX.

Figure 8:
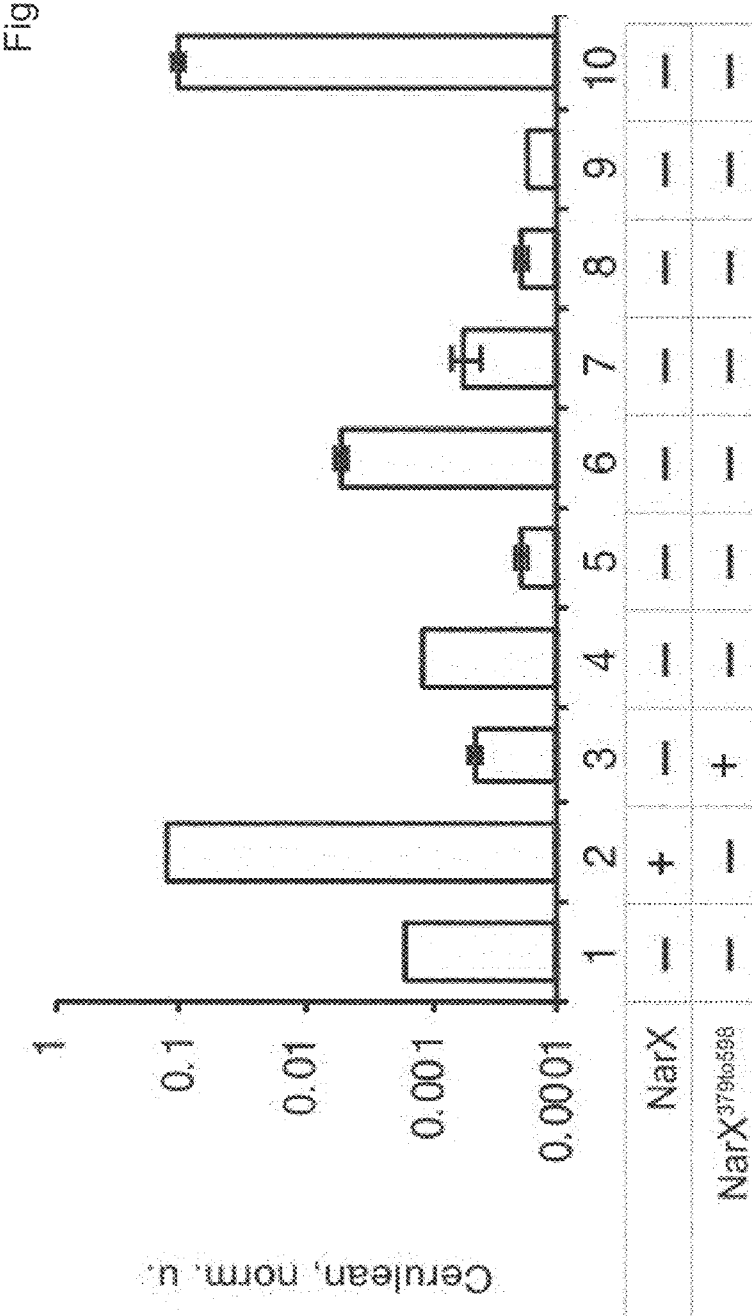
FIG. 8 shows the restoration of two-component signalling via forced dimerization fused to wild-type NarX or various NarX mutants. Signalling levels in mammalian cells expressing the response regulator NarL and NarL-regulated mCerulean fluorescent protein reporter, alone or with different combinations of SynZip1 and SynZip2 fused to wild-type NarX or various NarX mutants, as indicated in the chart. The bar charts display Cerulean level normalized to the expression of the transfection control in norm. u. as mean±SD of independent biological triplicates.
Figure 9:
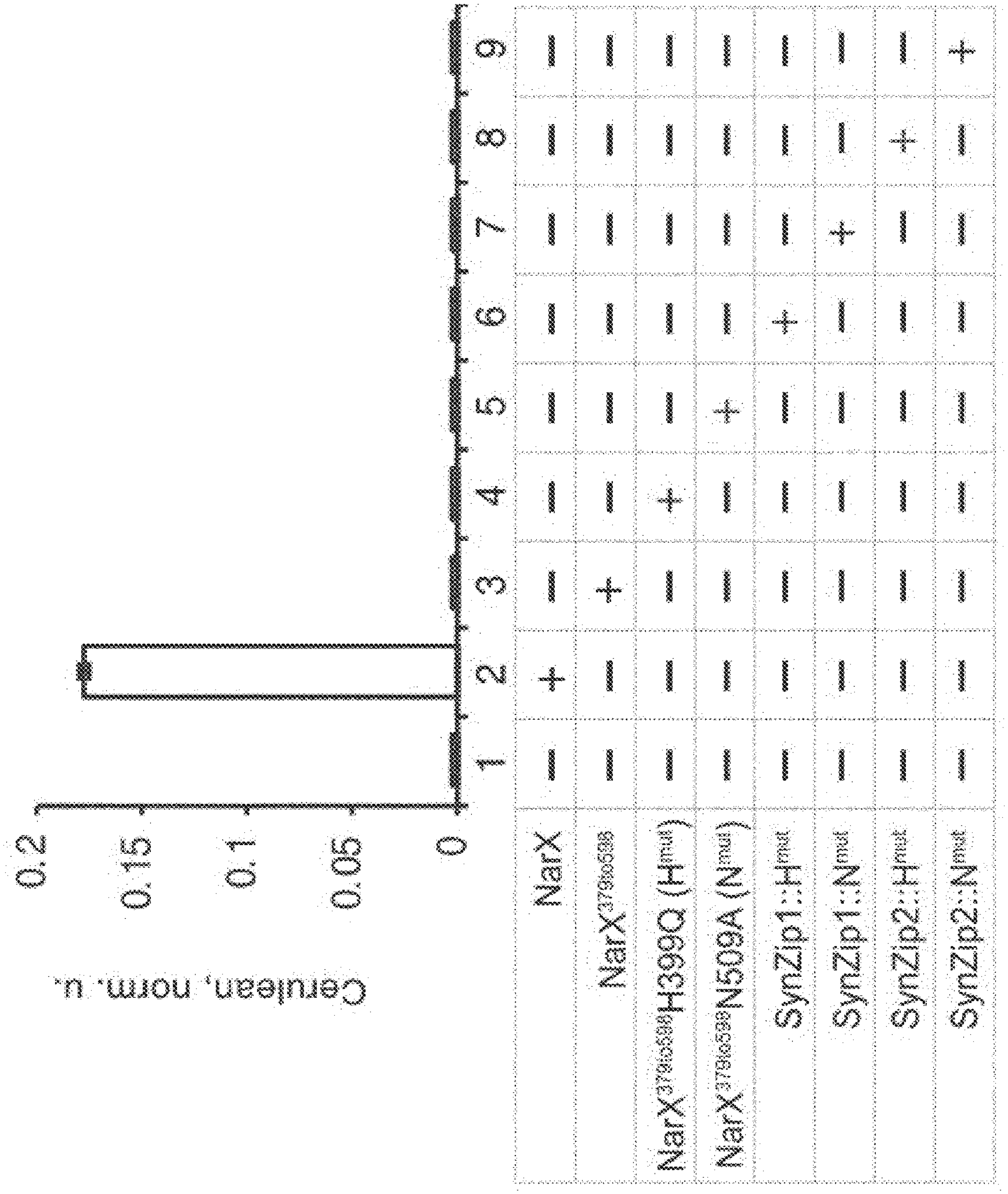
FIG. 9 shows the restoration of two-component signalling via forced dimerization. Signalling levels in mammalian cells expressing the response regulator NarL and NarL-regulated mCerulean fluorescent protein reporter, alone or with only one different variant of NarX mutant fused to SynZip1 or SynZip2, as indicated in the chart. The bar charts display Cerulean level normalized to the expression of the transfection control in norm. u. as mean±SD of independent biological triplicates.
Figure 10:
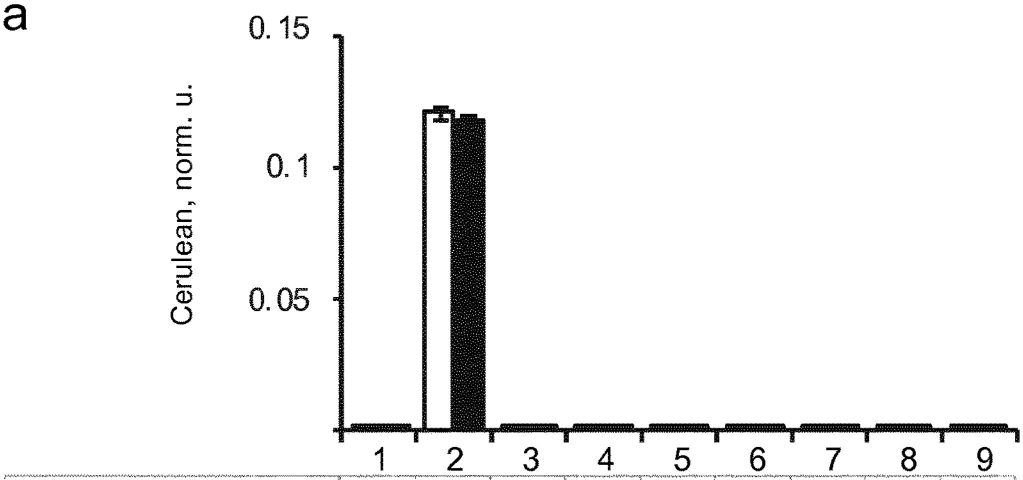
FIG. 10 shows the transduction of cytoplasmic ligand concentration to gene expression. (a) Signalling levels in mammalian cells expressing the response regulator NarL and NarL-regulated mCerulean fluorescent protein reporter, alone or with only one different variant of NarX mutant fused to FKBP and FRB, as indicated in the chart. For each pair of bars, the bar on the left (white) represents reporter expression without the A/C ligand, and the bar on the right (black) represents reporter expression with the ligand (100 nM). The bar charts display Cerulean level normalized to the expression of the transfection control in norm. u. (b) Representative microscopy images of the same transfections whose images are shown in FIG. 3*b*, including the transfection control channel (Red). In all panels the top and the bottom row of images show, respectively, the expression of mCherry transfection reporter (red pseudocolor), and pathway-induced mCerulean protein output (cyan pseudocolor) in the same transfection with or without ligand. The bar charts display Cerulean level normalized to the expression of the transfection control in norm. u. as mean±SD of independent biological triplicates.
Figure 10:
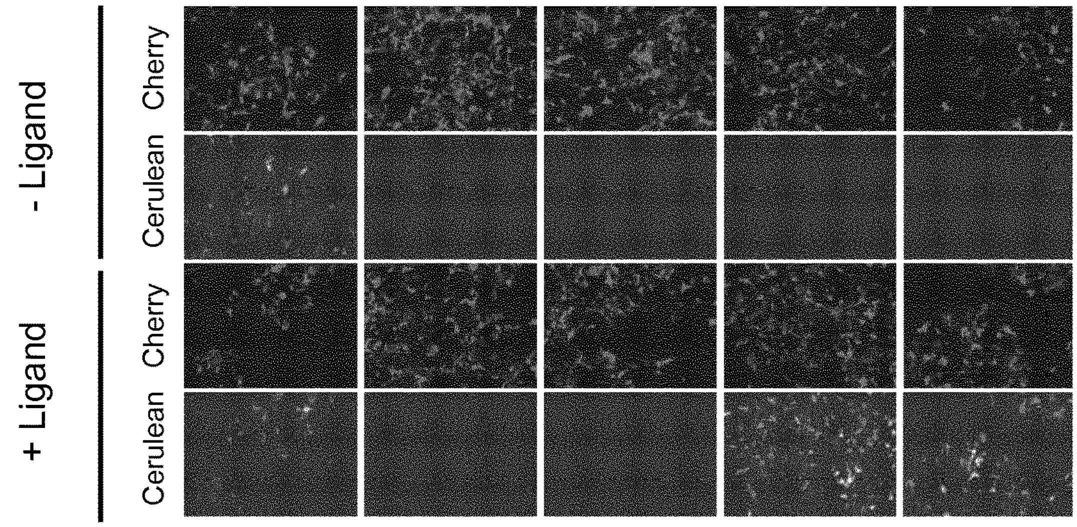

Next, the same mutations were introduced in the short cytoplasmic domain of NarX (FIG. 2*d*), and the resulting mutants were fused at the N-terminus to the SynZip1 and SynZip2 peptides as conducted earlier with the wild-type domain, creating, respectively, the constructs SynZip1::NarX$^{379to598}$H399Q (labelled for brevity from now on as SynZip1::H$^{mut}$) and SynZip2::NarX$^{379to598}$N509A (labelled SynZip2::N$^{mut}$) (FIG. 2*e*). The inventors also inverted the fusion pairs, generating SynZip2::NarX$^{379}$t$^{0598}$H399Q (SynZip2::H$^{mut}$) and SynZip1::NarX$^{379to598}$N509A (SynZip1::N$^{mut}$). It was found that when these pairs of constructs were coexpressed in HEK293 cells together with the NarL RR in the presence of the NarL-responsive reporter, the signalling via the NarL was fully restored to the level obtained with full-length, wild-type NarX, and generating a much stronger signal compared to the wild-type short NarX fusions (FIG. 8). The restoration was the same for both pairs (FIG. 2*f*, bars 11 and 12). When one or both of the fused SynZip domains were missing, the signalling stopped (FIG. 2*f*, bars 4-8, FIG. 9), indicating that the dimerization of the fusion domains was necessary and sufficient to restore the signalling. Interestingly, the pair of complementing NarX mutants, both fused to SynZip1 (SynZip1::H$^{mut}$ and SynZip1::N$^{mut}$) also resulted in elevated signalling activity (FIG. 2*f*, bar 9), consistent with the (weaker) effect observed under similar conditions with the wild type domain (FIG. 6, bar 4). This leads to the hypothesis that SynZip1 domain is capable of homodimerizing, albeit with a reduced affinity compared to SynZip1-SynZip2 interaction. Indeed, examination of the original literature suggests that SynZip1 exists as both a monomer and a dimer in size exclusion chromatography experiment, and it does so to a larger extend than SynZip2 alone. To evaluate the dose-response behaviour of the signalling intensity, the inventors characterized output levels for varying plasmid dosage of the NarX-derived constructs (FIG. 2*g*). The activity increases proportionally to the plasmid dosage, with the full-length wild-type NarX exhibiting the highest dosage sensitivity, likely reflecting the strongest dimerization constant, the SynZip1-SynZip2 pair showing a slightly reduced but comparable dimerization behaviour, and SynZip1 clearly showing inferior dimerization. For example, reducing the plasmid amount by about 16-fold compared to the initially-used conditions (6.25 ng instead of 100 ng) reduces SynZip1-SynZip1 signalling to background level, while still resulting in strong SynZip1-SynZip2 dimerization, consistent with expectation.

In summary, these experiments suggest that NarX-enabled signalling can be restored upon forced dimerization of the complementing, truncated mutant domains, and that this restoration is dose- and interaction strength dependent. Consistently with the current knowledge of two component signalling stoichiometry with about 1:30 HK:RR ratio in *E. coli*, NarX expression of about 10% compared to NarL fully activates the reporter output. This is because the promoter driving NarL, EF1α-V1 (see Methods), is about 5 times weaker than wild-type EF1α promoter driving NarL, and in addition plasmid dosage ratio of 1:2 (i.e., 50 ng of NarX-derived plasmid vs 100 ng of the RR-encoding plasmid) already saturates the response.

FK506/FKBP

To enable bona fide signalling, the dimerization of the NarX domains should be preferably controlled by an external stimulus. Inducible protein-protein interaction is a common signalling mechanism both in the cytoplasm and across the membrane. A well characterized ligand-induced heterodimerization takes place between the proteins FK506-binding protein 12 (FKBP) and FKBP12-rapamycin binding domain (FRB) mutant FRB$^{T2098L}$ in the presence of the small molecule A/C heterodimerize (a rapamycin analog Cl 6-(S)-7-methylindolerapamycin, known also as AP21967).

Figure 3A:
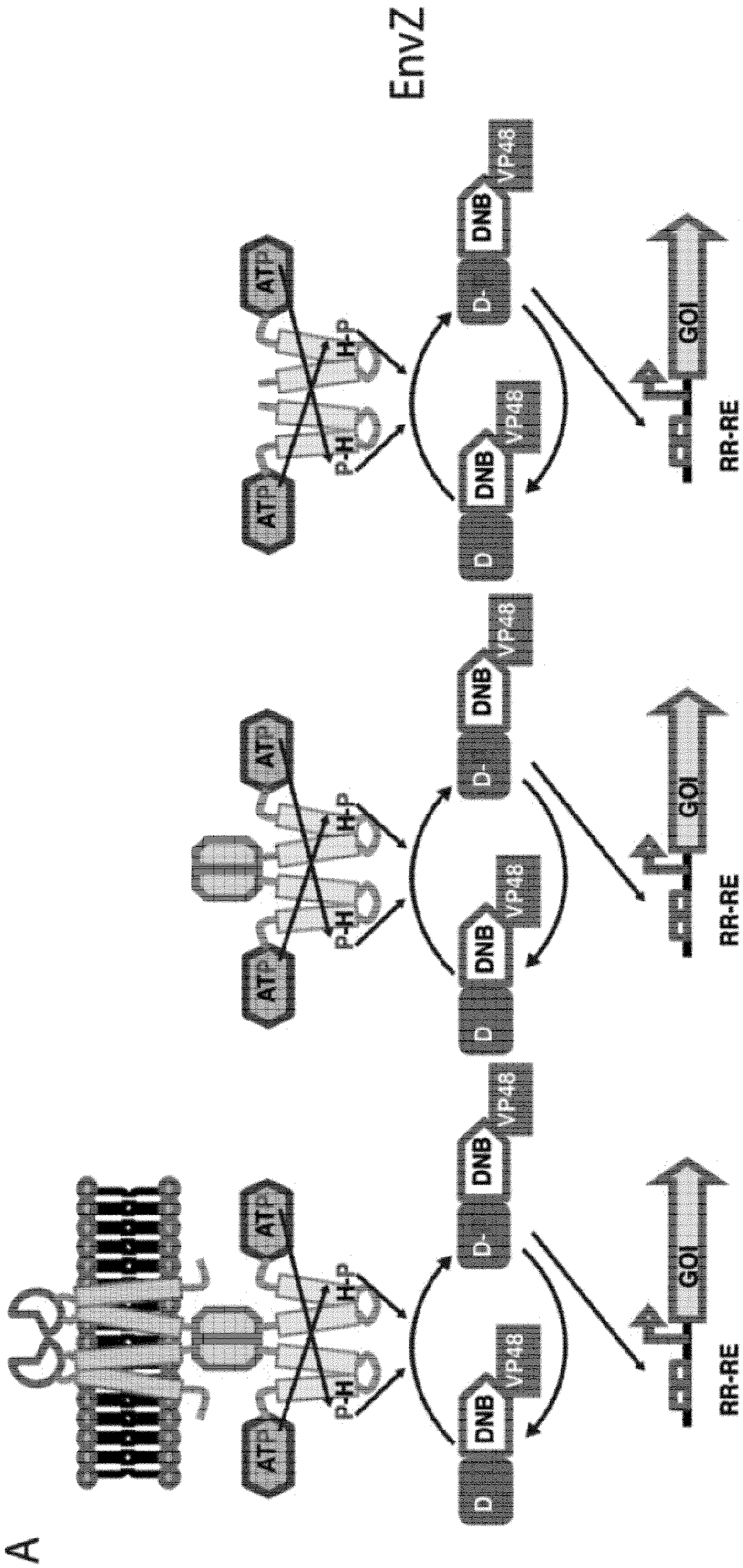
FIG. 3 shows the activity of truncated HK. (A) Schematic representation of phosphotransfer occurring in between element of EnvZ/OmpR (the upper lane) and of NarX/NarL (lower lane) in mammalian cells expressing WT HK (first column), sensor domain truncated mutant (second column), or sensor and transmitter domain truncated mutant (third column). (B) Quantitative data for mammalian cells expressing reporter gene alone or in combination with wild type HK, sensor domain truncated mutant ($EnvZ^{180to450}$ and $NarX^{176to598}$), or sensor and transmitter domain truncated mutant ($EnvZ^{223to450}$ and $NarX^{379to598}$). The bar charts display Cerulean level normalized to the expression of the transfection control in norm. u. as mean±SD of independent biological triplicates.
Figure 3:
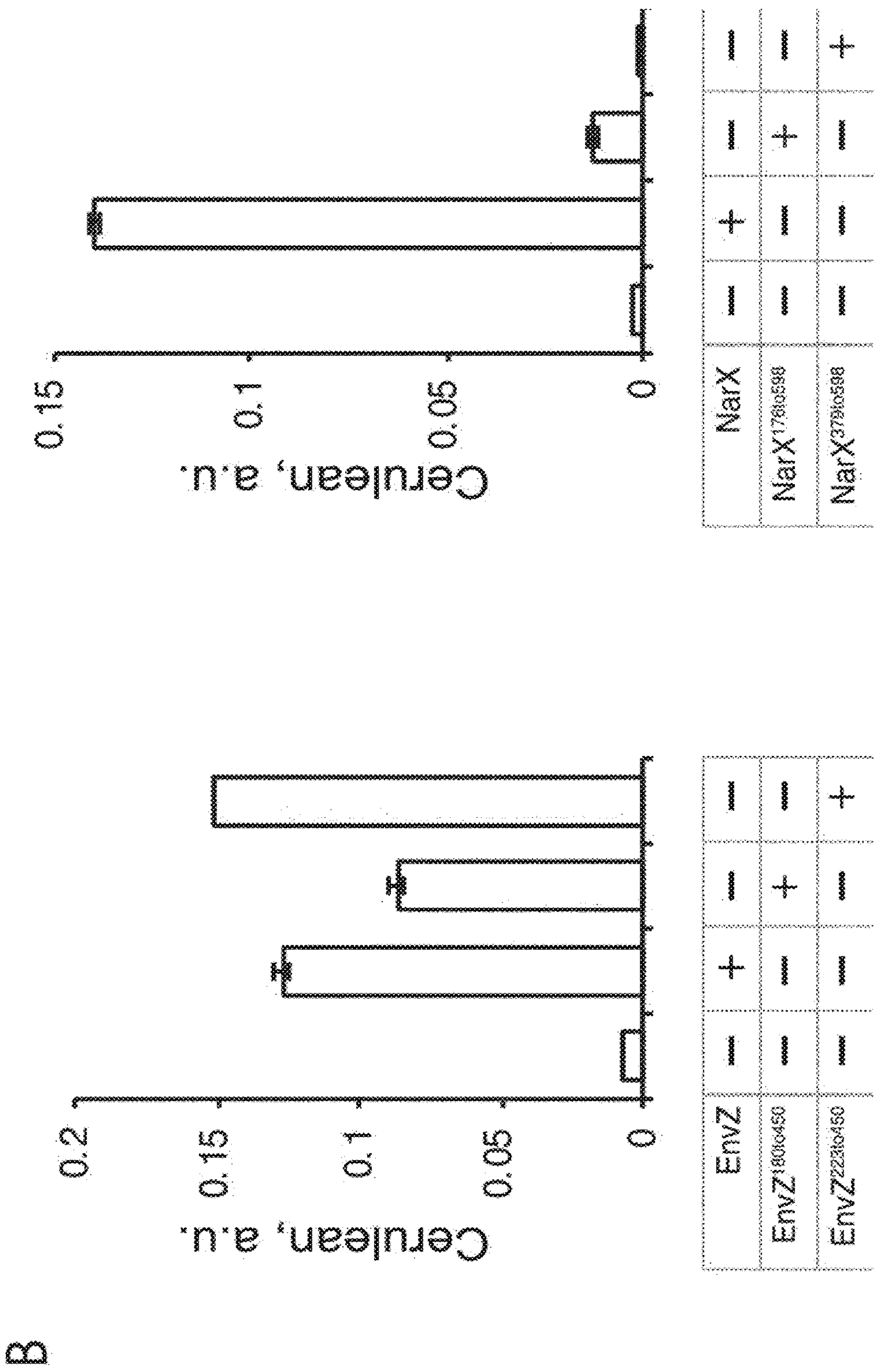

To find out if NarX domains are capable of transducing this interaction (FIG. 3*a*), the complementing histidine and asparagine NarX mutants described above were fused at their N-terminus to the FKBP (FK) and the FRB$^{T2098L}$ (FR) proteins, respectively, resulting in the fusions FK::NarX$^{379to598}$H399Q (FK::H$^{mut}$) and FR::NarX$^{379to598}$N509A (FR::N$^{mut}$), and the inverse pair FR::H$^{mut}$ and FK::N$^{mut}$. First, it was confirmed that NC did not affect the wild-type NarX/NarL system, transfecting HEK cells with NarX or NarX$^{379to598}$ in the absence or the presence of 100 nM of A/C (FIG. 3*b*, bars 2 and 3). Next, the inventors probed the ligand-induced signalling in a fashion similar to the one used for SynZip1-SynZip2 experiments, expressing different fusion variants and control constructs in HEK293 cells, in the presence of the response regulator NarL and NarL-activated reporter construct, this time with and without the ligand (FIG. 3*b*, FIG. 8). As expected, full length wild type NarX was constitutively active. In all the cases except with wild-type NarX, there was no signalling in the absence of the ligand. High level of the ligand was able to induce strong signalling (FIG. 3*b*, bars 11 and 12) only when (i) the NarX-derived domains contained complementary histidine and asparagine mutations and (ii) they were fused, respectively, to FKBP and FRB interaction partners. The inventors then proceeded to characterize the dose-response behaviour of this engineered signal transduction pathway using the pair FR::H$^{mut}$ and FK::N$^{mut}$ (FIG. 3*c*). The dose-response shows an expected Hill function dependency, from which the EC50 in the context of the assay was determined to be 1.3 nM as compared to the published values of 10 nM and 36 nM.

Figure 4:
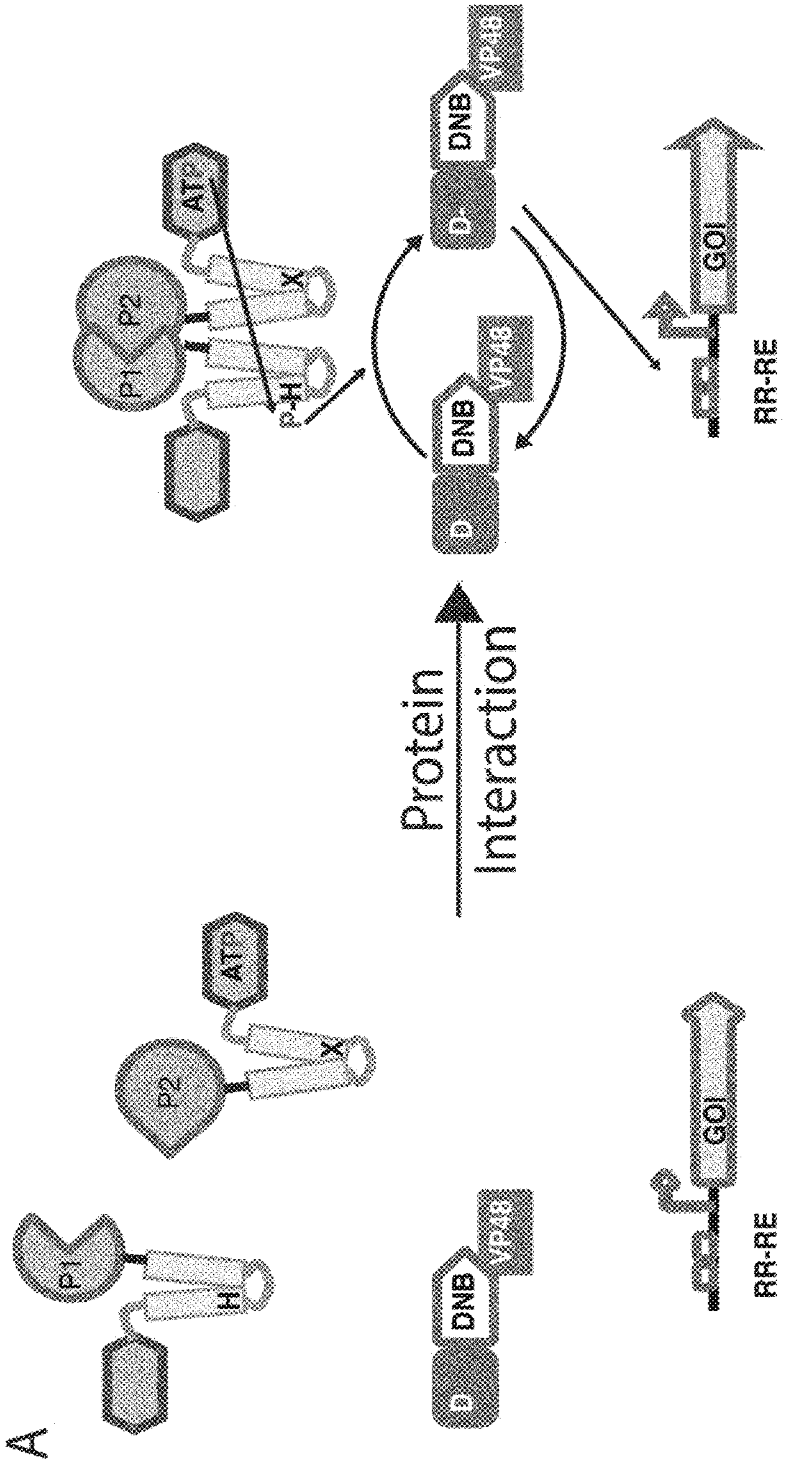
FIG. 4 shows the design of the protein/protein interaction assay. (A) Schematic representation of the PPI assay to monitor the interaction between two proteins P1 and P2. The interaction between P1 and P2, spontaneously or induced by the compound, allow the dimerization of the short cytoplasmic domain of HK of the trans phosphorylation family mutated at the level of the CA domain fused to P1 with short cytoplasmic domain of HK of the trans phosphorylation family mutated at the level of the DHp domain fused to P2. The dimerization will trigger the phosphorylation of the RR which will bind its RE and induces the expression of the reporter gene. (B) Quantitative data for mammalian cells expressing HK mutant fused to SZ1 or SZ2 domain. (C) Quantitative data for mammalian cells expressing HK mutant fused to FKBP or FRB domain in absence (white bar) or in presence of A/C heterodimezer (black bar) which induce the dimerization of the FKBP and FRB domain. The bar charts display Cerulean level normalized to the expression of the transfection control in norm. u. as mean±SD of independent biological triplicates.
Figure 4:
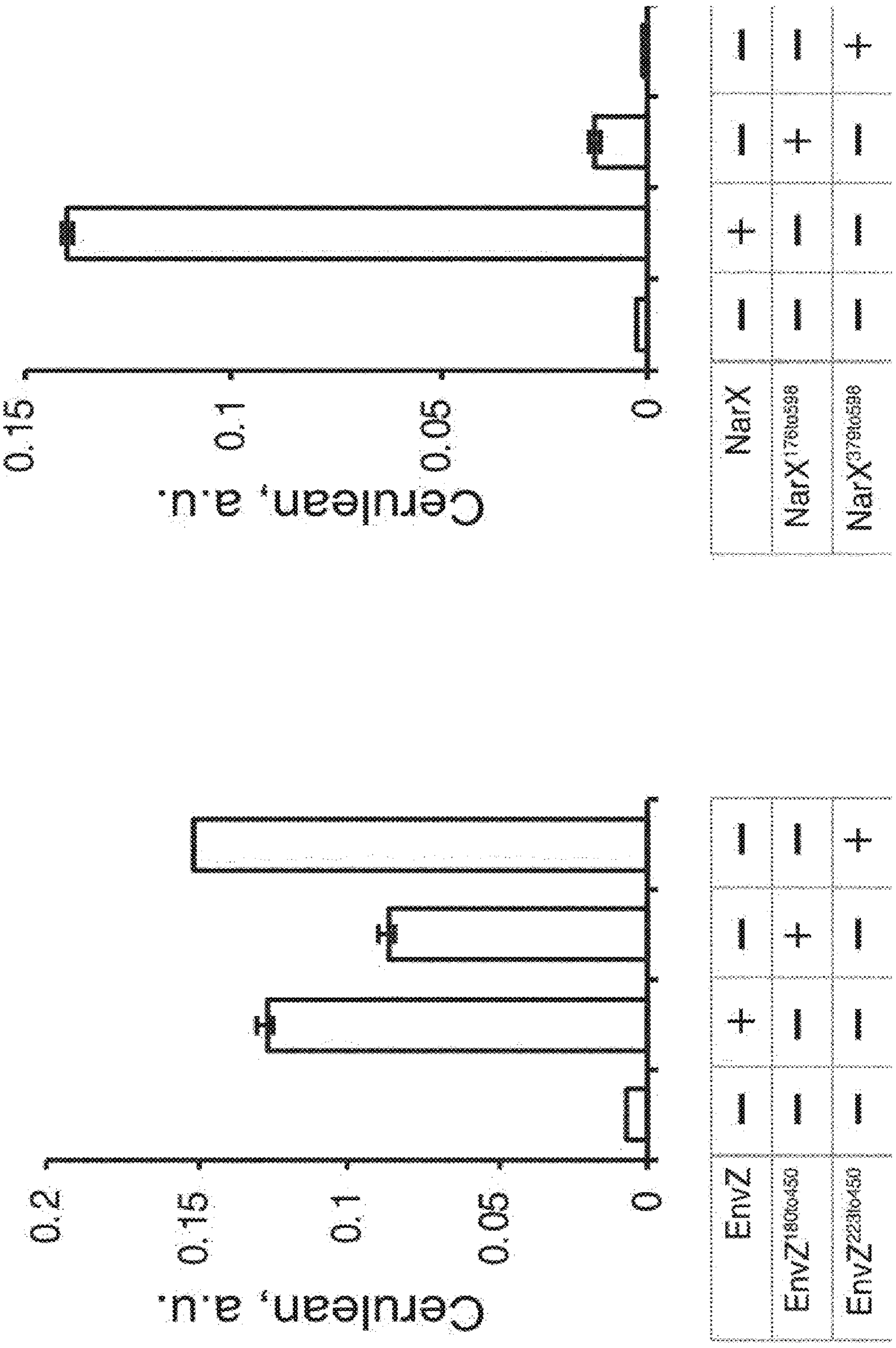
Figure 4:
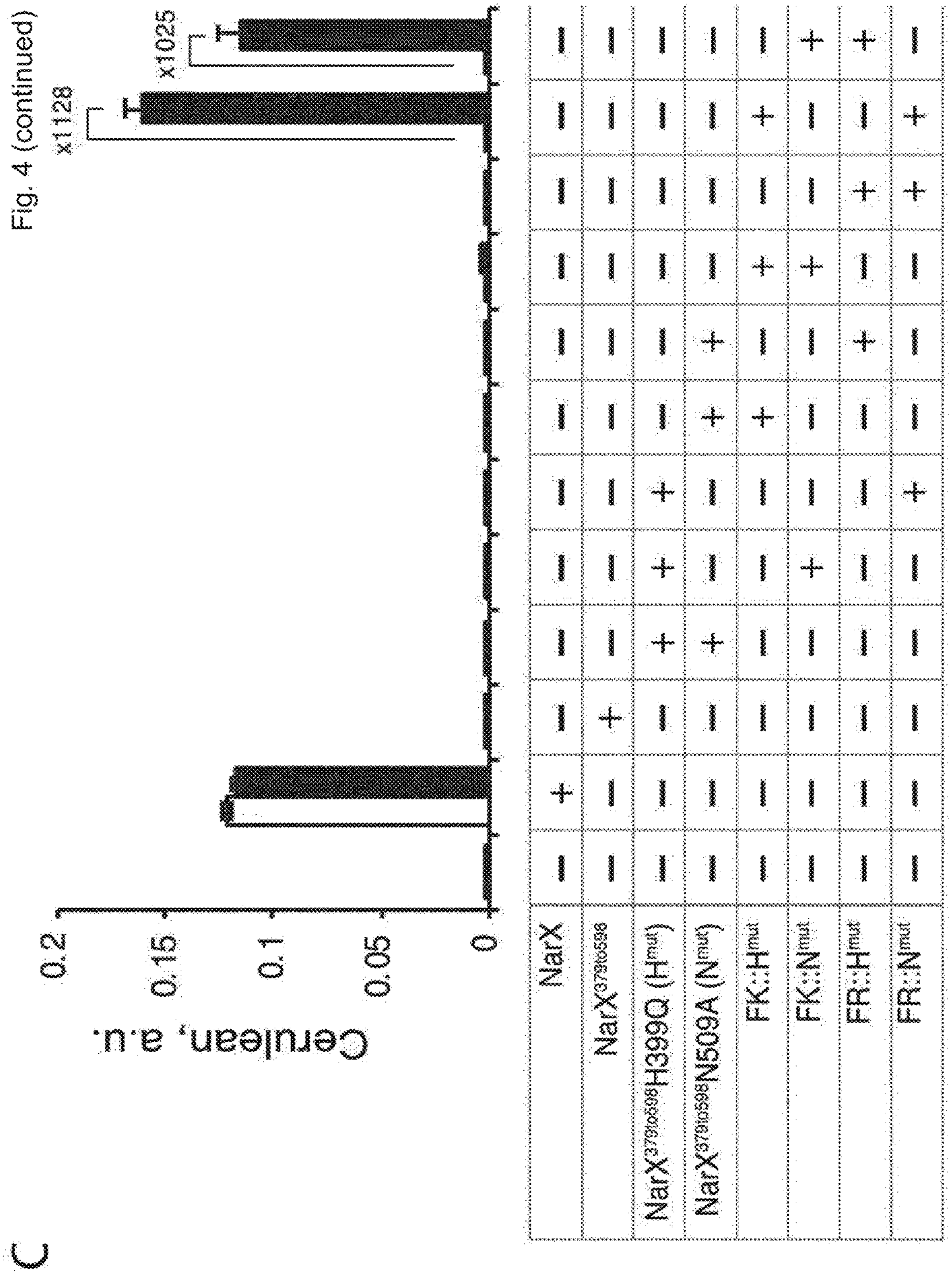
Figure 5A:
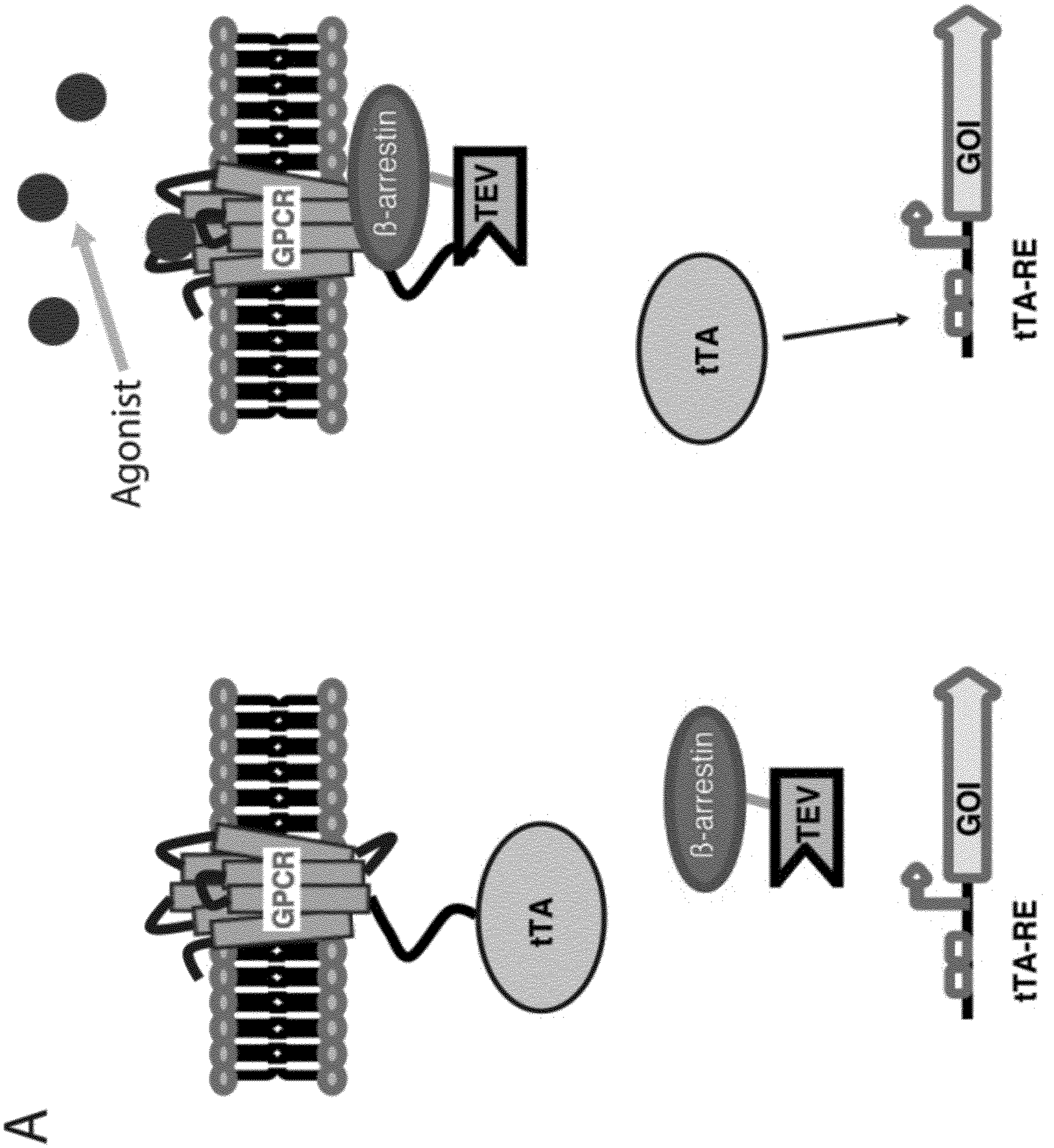
FIG. 5 shows the design of the protein/protein interaction assay (PPI) for GPCR. (A) Schematic representation of the TANGO assay to monitor the interaction between GPCR and beta-arrestin. The interaction between GPCR and beta-arrestin induced by the agonist allow the beta-arrestin-TEV protease fusion to localize at the level of the GPCR-tTA and trigger the release of the transcription factor tTA. (B) Schematic representation of the PPI assay to monitor the interaction between GPCR and beta-arrestin. The interaction of GPCR and beta-arrestin induced by the agonist, allows the dimerization of the short cytoplasmic domain of HK of the trans phosphorylation family mutated at the level of the CA domain fused to GPCR with short cytoplasmic domain of HK of the trans phosphorylation family mutated at the level of the DHp domain fused to beta-arrestin. The dimerization will trigger the phosphorylation of the RR which will bind its RE and induces the expression of the reporter gene. (C) Quantitative data for mammalian cells expressing the TANGO. (D) Quantitative data for mammalian cells expressing HK mutant fused to GPCR or beta-arrestin in absence (white bar) or in presence of procaterol (black bar). The bar charts display Cerulean level normalized to the expression of the transfection control in norm. u. as mean±SD of independent biological triplicates.
Figure 5B:
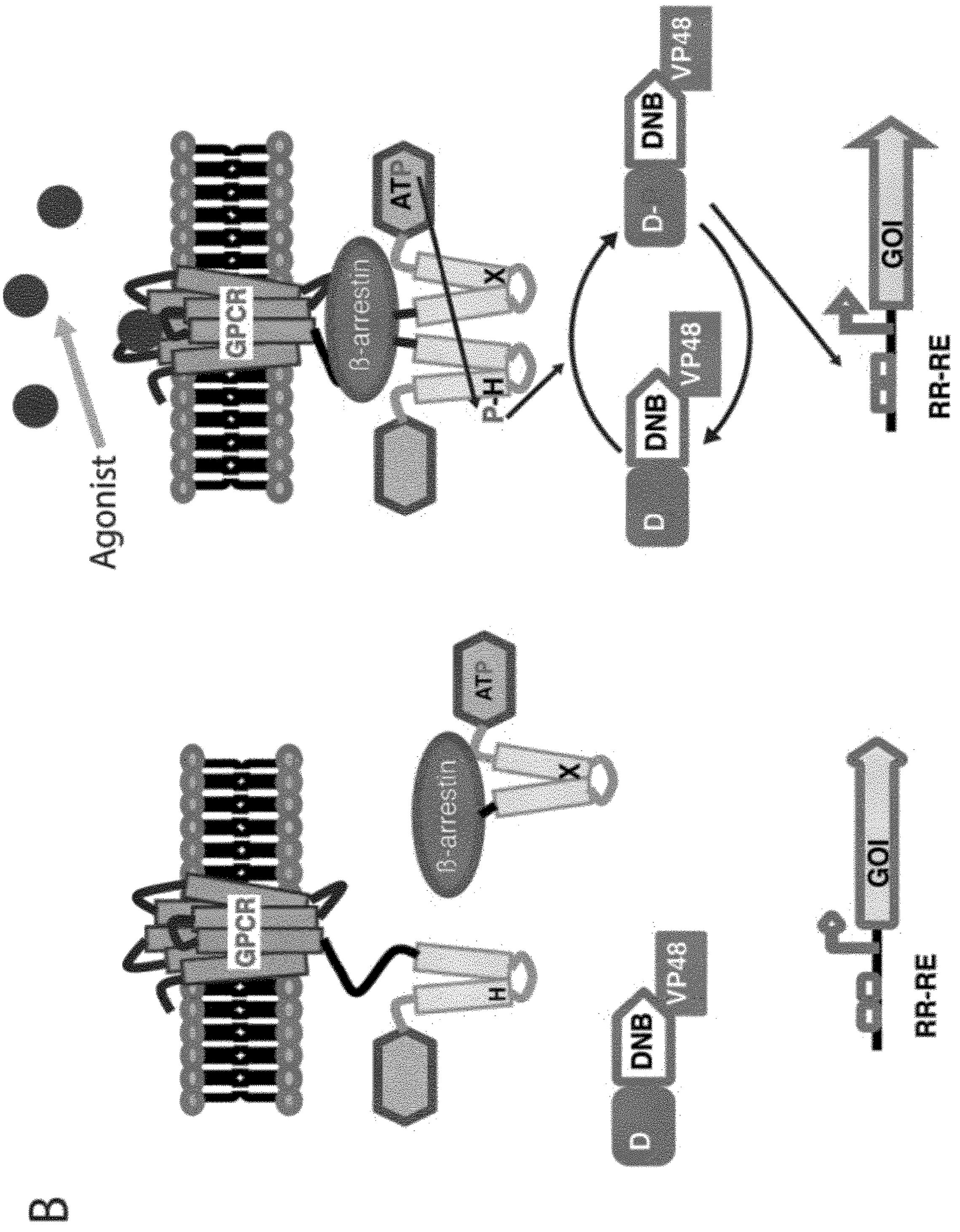
Figure 5:
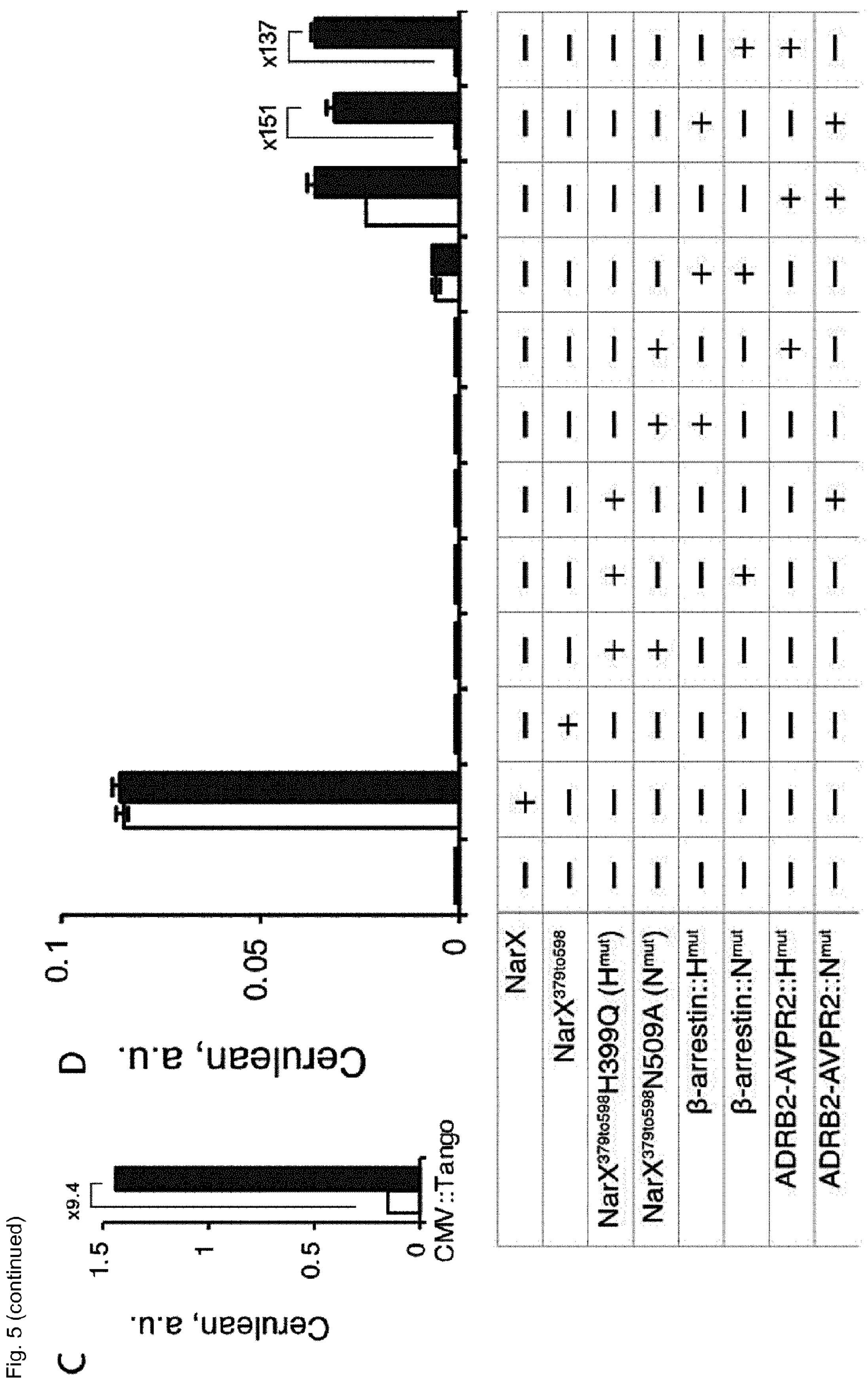

The above results illustrate the ability of TCS-based components to mediate signal transduction in the cytoplasm. However, a bulk of signalling takes place across the membrane. Many transmembrane signalling pathways involve protein-protein interactions at the cytoplasmic surface of the lipid bilayer, including an important class of signalling pathways initiated by G-protein coupled receptors (GPCRs), a family of a few hundred proteins. A key step of GPCR signal transduction is the formation of a complex between the GPCR itself and the protein beta-arrestin, followed by various processes that include GPCR internalization, recycling, and signaling. This interaction was previously shown to be sufficient for rewiring GPCR signalling by specific proteolytic cleavage of a fused transcriptional activator. The inventors hypothesized that this interaction could also enable catalytic transmembrane signalling via the two-component pathway. To this end, the inventors fused truncated histidine mutant of NarX, NarX$^{379to598}$H399Q, to a GPCR ADRB2-AVPR2: the procaterol-activated chimera of Adrenoceptor Beta 2 (ADRB2) and the cytoplasmic fragment of Arginine Vasopressin Receptor 2 (AVPR2). The inventors also fused the truncated asparagine mutant of NarX, NarX$^{379to598}$N509A, to beta-arrestin 2 (FIG. 4*a*). Lastly, the inventors implemented these fusions in reverse to check if the effect was symmetric.

Figure 11:
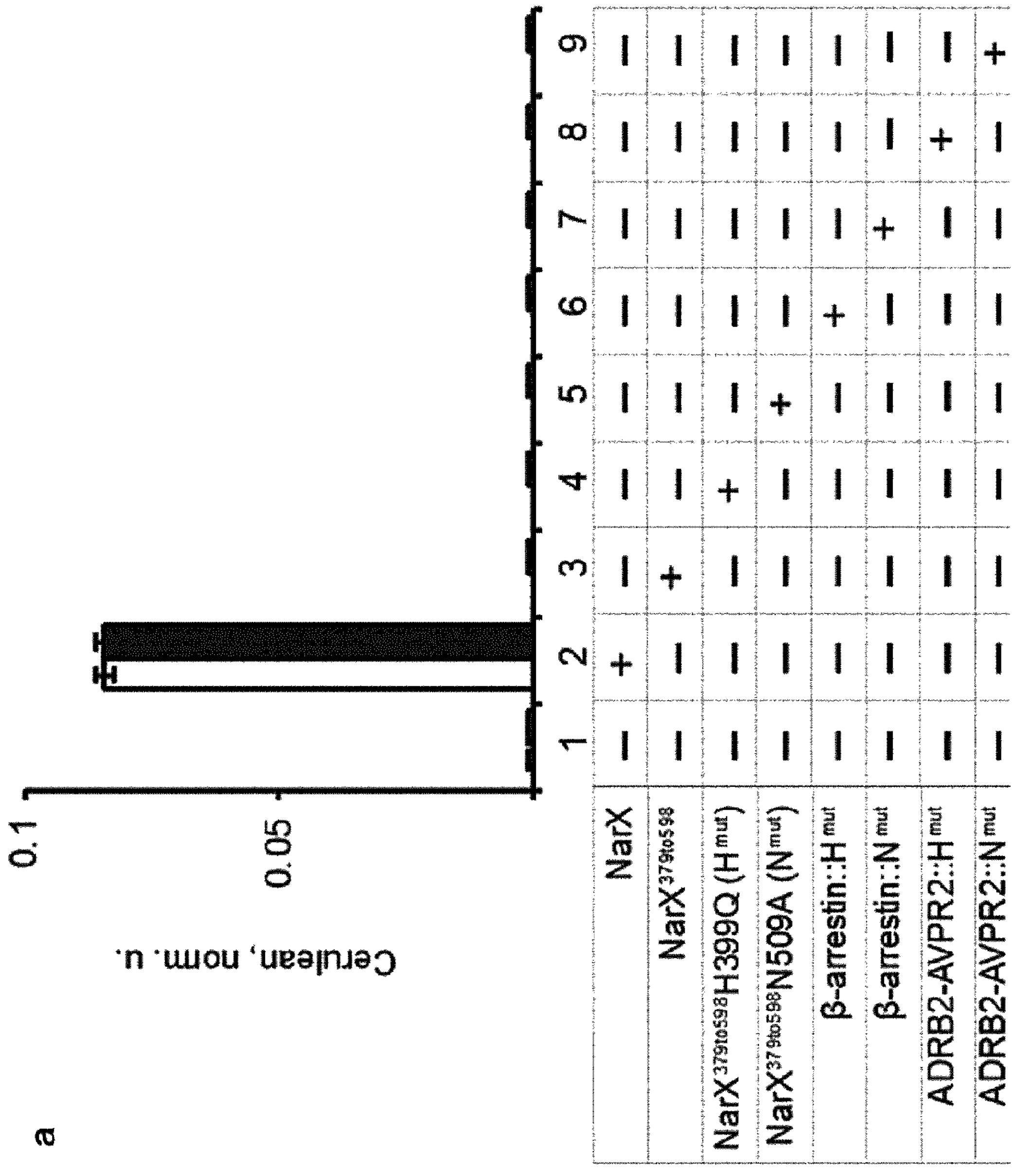
FIG. 11 shows the rewiring of the GPCR activity to the expression of a reporter gene. (a) Signalling levels in mammalian cells expressing the response regulator NarL and NarL-regulated mCerulean fluorescent protein reporter, and different combinations of the indicated protein domains and their fusions. (b) Signalling levels in mammalian cells expressing the TANGO assay components from CMV or EF1α-V1 promoter. For each pair of bars in panels a and b, the bar on the left (white) represents reporter expression without procaterol, and the bar on the right (black) represents reporter expression with procaterol (2 μM). The bar charts display Cerulean level normalized to the expression of the transfection control in norm. u. as mean±SD of independent biological triplicates. (c) Representative microscopy images of the same selected transfections whose images are shown in FIG. 4, here also showing the expression of the mCherry transfection control. In all panels the top and the bottom row of images show, respectively, the expression of mCherry transfection reporter (red pseudocolor), and pathway-induced mCerulean protein output (cyan pseudocolor) in the same transfection with or without ligand.
Figure 11:
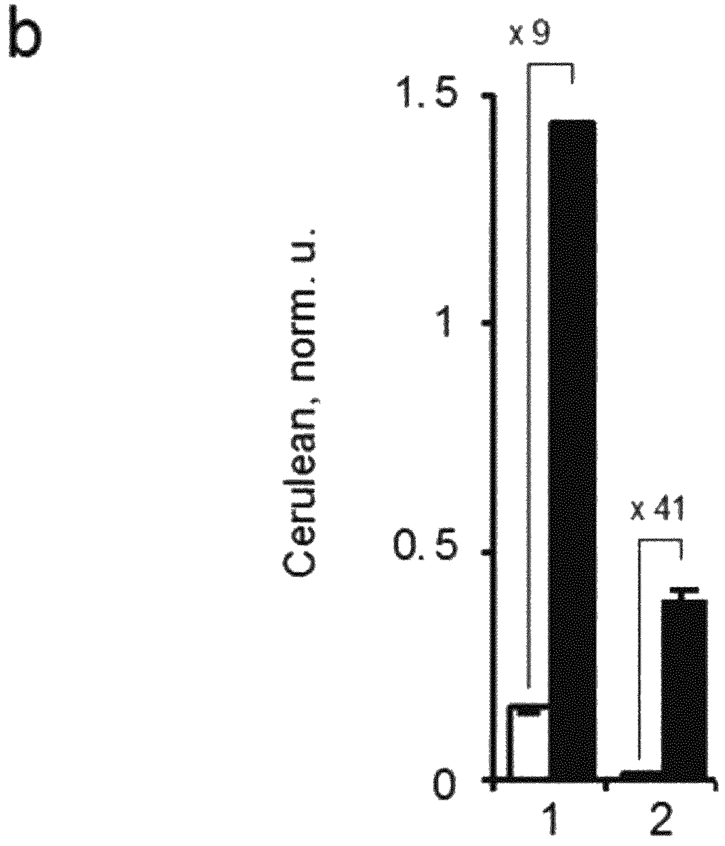
Figure 11:
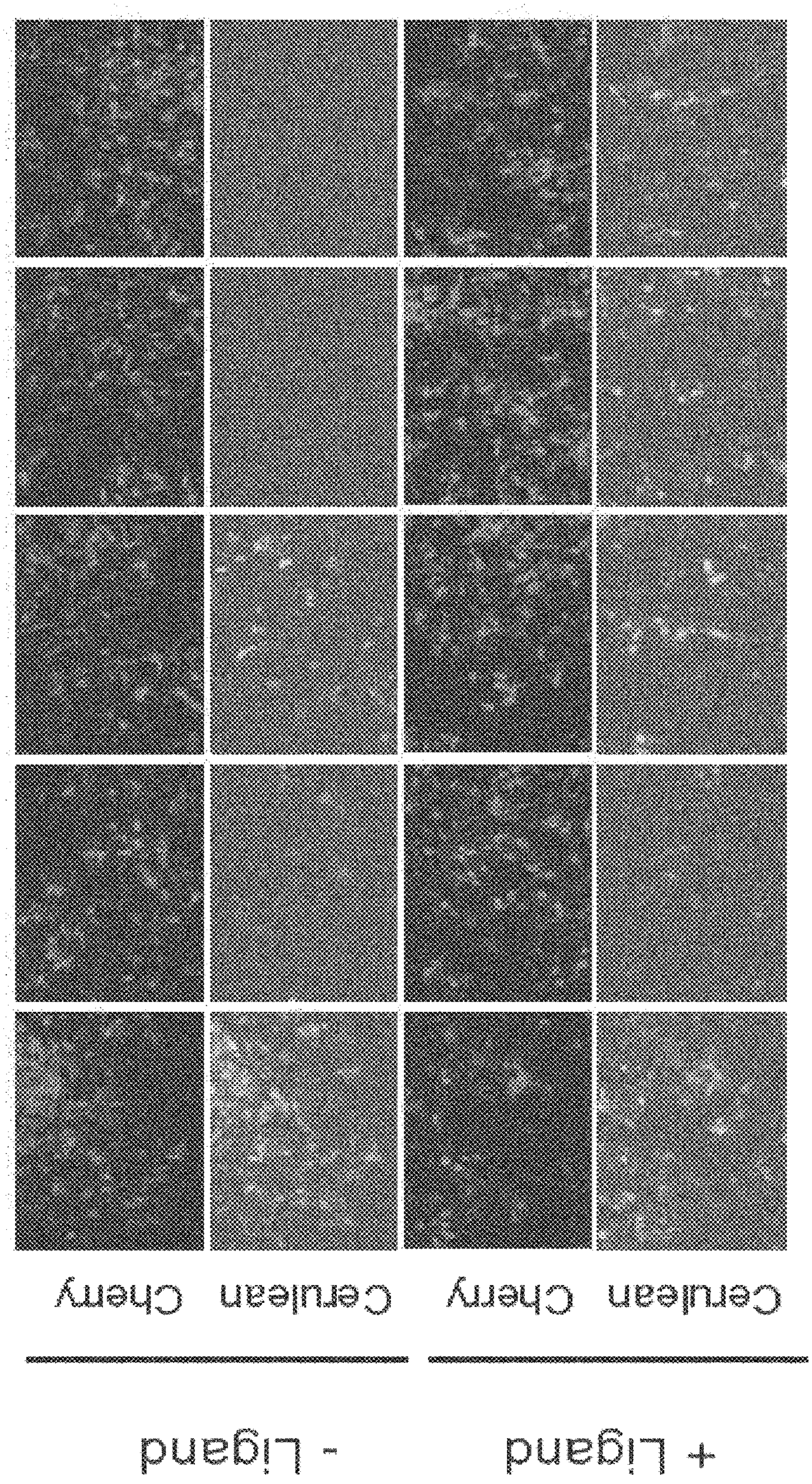

First, it was confirmed that procaterol did not affect the signalling via NarX/NarL system. HEK293 cells co-transfected with NarL and NarL-activated reporter with either NarX or NarX$^{379to598}$, in the absence or presence of 100 nM procaterol, showed respectively fully induced and background reporter expression independent of the procaterol (FIG. 4*b*, bars 2 and 3). In the experiments (FIG. 4*b*, FIG. 11*a*) combining the complementary NarX mutants fused, respectively, to the GPCR receptor, beta-arrestin, or both, it was found that there was a certain amount of procaterol-independent signalling with beta-arrestin and the GPCR receptor alone (FIG. 4*b*, bars 9 and 10). The effect was more pronounced with the GPCR, suggesting that the receptors dimerize in ligand-independent fashion. Importantly, very strong procaterol-triggered signalling took place when the complementary NarX mutants were fused to the GPCR receptor and the beta-arrestin, respectively, with an induction dynamic range above 3 orders of magnitude (FIG. 4*b*, bars 11 and 12). The obtained dynamic range with the two-component based system was higher than the one obtained in a TANGO assay, a proteolysis-based assay for GPCR activation (FIG. 11*b*).

To determine whether the synthetic signalling cascade is able to recapitulate the effects of different known GPCR ligands, the inventors characterized the dose response of a system comprising the pair ADRB2-AVPR2::H$^{mut}$ and beta-arrestin::N$^{mut}$ in the presence of two agonists (procaterol, isoproterenol) and one partial agonist (clenbuterol). It was observed that the two full agonists, procaterol (FIG. 4*c*, blue line) and isoproterenol (FIG. 4*c*, red line), induce strong downstream gene expression in a dose-dependent manner and reach the same maximum response at saturating doses. In the presence of the partial agonist clenbuterol, the expression of the reporter gene is 3.5 times lower than in presence of the full agonists (FIG. 4*c*, compare green line with blue and red lines). In addition, single-cell flow cytometry data suggests monomodal, rather than bimodal, induction (FIG. 4*d*, TCS data). EC50 values of procaterol, isoproterenol and clenbuterol were determined from the dose-response curves to be 5 nM, 30 nM and 14 nM, respectively. These values are similar to the ones described in the literature and to the values that were determined by using the TANGO assay (FIG. 4*c*, dashed lines, secondary axes). Note that while the TANGO assay results in higher absolute reporter expression, the leakage is much higher compared to TCS-based mechanism and the single cell data is bimodal (FIG. 4*d*, TANGO data). The inventors also characterized the effect of the antagonist propranolol in the presence of the procaterol, and found that in the signalling cascade of the invention, the antagonist inhibited the effect of the procaterol in a dose-dependent fashion (FIG. 4*e*, blue line). The inventors determined the $IC_{50}$ of the antagonist in the context of this assay to be 2 nM, which is similar to the value obtained by using the TANGO assay (FIG. 4*e*, dashed line). These results demonstrate that the system of the invention can faithfully transduce a variety of known effects of agonists and antagonists on the GPCR activity and it can be used to extract quantitative data on interaction parameters.

SUMMARY

Implementing non-native signalling modalities in cells, in particular mammalian cells, is highly desirable for rational control of cell behaviour and ultimately, engineering novel cellular functions for basic research, biotechnology and medicine. Two-component signalling is evolutionary extremely divergent from vertebrate signalling, and to the best of the inventors' knowledge, not a single instance of histidine to aspartate phosphoryl transfer has been described in vertebrate cells. The native mechanism of TCS signal transduction in prokaryotes relies on ligand-induced conformation change of the HK dimer in the membrane, but direct implementation of this mechanism in mammalian cells has been elusive. Instead, here the inventors pursued a different strategy to achieve essentially the same end result by controlling the signalling via switching between dissociated and associated states of the HK cytoplasmic domains. In the cases the inventors show here, the switching was accomplished by ligand-induced dimerization of proteins fused, respectively, to histidine and asparagine mutant of a truncated cytoplasmic domain of an HK NarX. A similar qualitative effect is observed when wild-type truncated domain is used instead of the mutants. However, the quantitative behaviour is inferior and more importantly, the resulting effect does not distinguish between ligand-induced dimerization of the two interaction partners and homo-dimerization of one of the partners, as was the case with SynZip1 and GPCR. One reason for the reduced dynamic range could be the stronger phosphatase activity of the wild-type domain, compared to the histidine mutant.

The approach retains many of the features of the original prokaryotic signalling. It is an amplifying, multiple turnover process with a single NarX dimer capable of phosphorylating multiple copies of the response regulator NarL, which in turn can induce multiple transcription initiation events. The inventors speculate that the two-step amplification resulted in a greatly improved dynamic range compared to the proteolytic-cleavage based approach. Further, upon stimulus withdrawal, the signalling will cease due to spontaneous dephosphorylation of the RR; this can be facilitated by judicious employment of the wild-type HK domains that retain their full phosphatase activity if quick signalling quiescence is required. Given the rich variety of TCS pathways, multiplexing of the synthetic signalling pathways is feasible by using the methods described above. Together, the result point toward a novel modality for sensing and signal transduction in mammalian cells, both in the cytoplasm and across the membrane.

Methods

Standard molecular cloning techniques were employed as available to the skilled person.

Plasmid Construction.

Plasmids were constructed using standard cloning techniques. All restriction enzymes used in this work were purchased from New England Biolabs (NEB). Q5 High-Fidelity DNA Polymerase (NEB) was used for fragment amplification. Single-strand oligonucleotides were synthesized by Sigma-Aldrich. Digestion products or PCR fragments were purified using GenElute Gel Extraction Kit or Gen Elute PCR Clean Up Kit (Sigma-Aldrich). Ligations were performed using T4 DNA Ligase (NEB) by temperature cycle ligation with 140 cycles between 30 s at 10° C. and 30 s at 30° C. Gibson assembly was done as described below. 5 µl of the ligation product or the Gibson assembly product were transformed into chemically competent *E. Coli* DH5a or *E. coli* TOP10 that were plated on LB Agar with Ampicillin at 100 µg/ml. The resulting clones where screened directly by colony-PCR (Dream Taq Green PCR Master Mix, Thermo Scientific). The inventors expanded single clones in LB Broth Miller Difco (BD) supplemented with ampicillin and purified their plasmid DNA using GenElute Plasmid Miniprep Kit (Sigma-Aldrich). All the resulting plasmids were sequence-verified by Microsynth using Sanger sequencing method. The DNA for mammalian transfection was obtained from 100 ml of liquid culture using the Promega PureYield™ Plasmid Midiprep System (A2495). The recovered DNA was further purified using the Norgen Endotoxin Removal Kit Mini (Cat. #27700) or Midi (Cat. #52200). A short cloning procedure for each construct used within this work is described below.

Gibson Assembly Protocol

The Gibson assembly was performed in 10 µl final volume by mixing vectors (0.018 pmol) and inserts (0.09 pmol) in 1× Gibson assembly buffer (0.1 M Tris-HCl, pH 7.5, 0.01 M $MgCl_2$, 0.2 mM dGTP, 0.2 mM dATP, 0.2 mM dTTP, 0.2 mM dCTP, 0.01 M DTT, 5% (w/v) PEG-8000, 1 mM NAD), 0.04 units of T5 exonuclease (NEB), 0.25 units of Phusion DNA polymerase (NEB) and 40 units of Taq DNA ligase (NEB). Negative controls for Gibson assemblies included vectors alone. The Gibson assembly was realized at 50° C. for 1 h.

Recombinant DNA Cloning Protocols

OmpR_RE-cerulean (pMZ1): The mCerulean coding sequence from EF1α-cerulean (pKH24) was digested with NotI and SmaI and cloned into the plasmid OmpR_RE-amCyan (pJH008) digested with AfeI and PspOMI CMV-envZN347A (pMZ37): The 5' and the 3' fragments of envZ was PCR amplified with PR3687/PR3708 and PR3707/PR3709 from the plasmid CMV-envZ (pJH001). The primers were designed to introduce a mutation exchanging the codon encoding for the asparagine (N) at the 347th position to codon encoding for an alanine (A). Both PCR products and the plasmid CMV-envZ (pJH001[14]) digested with XhoI and PvuII were assembled using Gibson mix.

CMV-envZ$^{223to450}$ (pMZ123): The 3' fragments of envZ was PCR amplified with PR4345/PR4346 from the plasmid CMV-envZ (pJH1). The primers were designed to amplify the sequence from the 20th codon upstream of the codon encoding for the phosphorylable histidine at the position 243 till the end of the gene, and to insert ATG sequence in front of this amplified sequence. The PCR products and the plasmid CMV-envZ (pJH001) digested with XhoI and AgeI were assembled using Gibson mix.

CMV-narX N509A (pMZ160): The 5' and the 3' fragments of narX were PCR amplified with PR4122/PR4541 and PR4346/PR4542 from the plasmid CMV-narX (pJH002). The primers were designed to introduce a mutation exchanging the codon encoding for the asparagine (N) at the 509th position to codon encoding for an alanine (A). Both PCR products and the plasmid CMV-envZ (pJH001) digested with XhoI and AgeI were assembled using Gibson mix.

CMV-narX$^{379to598}$ (pMZ163): The 3' fragment of narX was PCR amplified with PR4345/PR4546 from the plasmid CMV-narX (pJH002[14]). The primers were designed to amplify the sequence from the 20th codon upstream the codon encoding for the phosphorylable histidine at the position 399 till the end of the gene, and to insert ATG sequence in front of this amplified sequence. The PCR products and the plasmid CMV-envZ (pJH001) digested with XhoI and AgeI were assembled using Gibson mix.

EF1α-V1-envZ-mCherry (pMZ194): The EF1α-V1, as shortened version of EF1α, was PCR amplified with PR4733/PR4734 from the plasmid pRA114 (Altamura et al, manuscript in preparation). The promoter and the plasmid EnvZ-GGGGS-mCherry (pEM017[14]) digested with PspOMI and AgeI were assembled using Gibson mix.

CMV-SynZip1::narX$^{379to598}$ (pMZ200): the inventors performed de novo synthesis of gBlock sequence encoding for SynZip1 and G4S linker (gBlock264) via IDT. The coding sequence of NarX$^{379to598}$ was PCR amplified with PR4346/PR4747 from the plasmid CMV-narX$^{176to598}$ (JH010[14]). The gBlock, the PCR product and the plasmid CMV-envZ (pJH001) digested with AgeI and XhoI were assembled using Gibson mix.

CMV-narX$^{379to598}$::SynZip1 (pMZ202): The inventors performed a de novo synthesis of gBlock sequence encoding for G4S linker and SynZip1 (gBlock265) via IDT. The coding sequence of NarX$^{379to598}$ was PCR amplified with PR4122/PR4747 from the plasmid CMV-narX$^{379to598}$ (pMZ163). The gBlock, the PCR product and the plasmid CMV-envZ (pJH001) digested with AgeI and XhoI were assembled using Gibson mix.

CMV-SynZip2::narX$^{379to598}$ (pMZ206): The inventors performed a de novo synthesis of gBlock sequence encoding for SynZip2 and G4S linker (gBlock269) via IDT. The coding sequence of NarX$^{379to598}$ was PCR amplified with PR4346/PR4747 from the plasmid CMV-narX$^{176to598}$ (JH010). The gBlock, the PCR product and the plasmid CMV-envZ (pJH001) digested with AgeI and XhoI were assembled using Gibson mix.

CMV-narX$^{379to598}$::SynZip1 (pMZ208): The inventors performed a de novo synthesis of gBlock sequence encoding for G4S linker and SynZip1 (gBlock270) via IDT. The coding sequence of NarX$^{379to598}$ was PCR amplified with PR4122/PR4748 from the plasmid CMV-narX$^{379to598}$ (pMZ163). The gBlock, the PCR product and the plasmid CMV-envZ (pJH001) digested with AgeI and XhoI were assembled using Gibson mix.

CMV-FRB T2098L::CBRC (pMZ211): The 5' of FRB and the 3' fragments of FRB with CBRC were PCR amplified with PR4122/PR4541 and PR4346/PR4542 from the plasmid FRB::CBRC[27]. The primers were designed to introduce a mutation exchanging the codon encoding for the threonine (T) at Both098$^{th}$ position (relative to the full protein Serine/Threonine-protein kinase TOR1) to codon encoding for a leucine (L). Both PCR products and the plasmid FRB::CBRC digested with BamHI and AgeI were assembled using Gibson mix.

CMV-FKBP::narX$^{379to598}$ (pMZ214): The sequence encoding for FKBP was PCR amplified with PR4766/PR4767 from the plasmid CBRN::FKBP[27]. The coding sequence of NarX$^{379to598}$ was PCR amplified with PR4346/PR4771 from the plasmid CMV-narX$^{176to598}$ (pJH010). The primers were designed to insert (G4S)2 linker between the amplified fragment. Both PCR products and the plasmid CMV-envZ (pJH001) digested with AgeI and XhoI were assembled using Gibson mix.

CMV-FRB T2098L::narX$^{379to598}$ (pMZ215): The sequence encoding for FRB T2098L was PCR amplified with PR4769/PR4770 from the plasmid CMV-FRB::CBRC (pMZ211). The coding sequence of NarX$^{379to598}$ was PCR amplified with PR4346/PR4771 from the plasmid CMV-narX$^{176to598}$ (pJH010). The primers were designed to insert (G4S)2 linker between the amplified fragment. Both PCR products and the plasmid CMV-envZ (pJH001) digested with AgeI and XhoI were assembled using Gibson mix.

NarL_RE-cerulean (pMZ219): The minimal response element NarL_RE was formed out by annealing the primers PR4892 and PR4893. The annealed product and the plasmid OmpR_RE-cerulean (pMZ1) digested with AscI and NdeI were assembled using Gibson mix.

EF1α-V1-SynZip1::narX$^{379to598}$ (pMZ221): The sequence encoding for SynZip1, G4S linker and NarX$^{379to383}$ was PCR amplified with PR3687/PR4971 from the plasmid CMV-SynZip1::NarX$^{379to598}$ (pMZ200). The PCR product and the plasmid EF1α-V1-envZ-mCherry (pMZ194) digested with AgeI and XhoI were assembled using Gibson mix.

EF1α-V1-SynZip2::narX$^{379to598}$ (pMZ222): The sequence encoding for SynZip2, G4S linker and NarX$^{379to383}$ was PCR amplified with PR3687/PR4971 from the plasmid CMV-SynZip2::narX$^{379to598}$ (pMZ206). The PCR product and the plasmid EF1α-V1-envZ-mCherry (pMZ194) digested with AgeI and XhoI were assembled using Gibson mix.

EF1α-V1-SynZip1::narX$^{379to598}$ H399Q (pMZ223): The sequence encoding for SynZip1 and G4S linker was PCR amplified with PR4971/PR4973 from the plasmid CMV-SynZip1::narX$^{379to598}$ (pMZ200). The sequence encoding for NarX$^{379to598}$ H399Q was PCR amplified with PR3687/PR4972 from the plasmid CMV-narX H399Q (pEM014). Both PCR products and the plasmid EF1α-V1-envZ-mCherry (pMZ194) digested with AgeI and XhoI were assembled using Gibson mix.

EF1α-V1-SynZip2::narX$^{3'}$ H399Q (pMZ224): The sequence encoding for SynZip2 and G4S linker was PCR amplified with PR4971/PR4973 from the plasmid CMV-SynZip2::narX$^{379to598}$ (pMZ206). The sequence encoding for NarX$^{379to598}$ H399Q was PCR amplified with PR3687/PR4972 from the plasmid CMV-narX H399Q (pEM014). Both PCR products and the plasmid EF1α-V1-envZ-mCherry (pMZ194) digested with AgeI and XhoI were assembled using Gibson mix.

EF1α-V1-SynZip1::narX$^{379to598}$ N509A (pMZ225): The sequence encoding for SynZip1 was PCR amplified with PR4971/PR4973 from the plasmid CMV-SynZip1::narX$^{379to598}$ (pMZ200). The sequence encoding for NarX$^{379to598}$ N509A was PCR amplified with PR3687/PR4972 from the plasmid CMV-narX N509A (pMZ160). Both PCR products and the plasmid EF1α-V1-envZ-mCherry (pMZ194) digested with AgeI and XhoI were assembled using Gibson mix.

EF1α-V1-SynZip2::narX$^{379to598}$ N509A (pMZ226): The sequence encoding for SynZip2 was PCR amplified with PR4971/PR4973 from the plasmid CMV-SynZip2::narX$^{379to598}$ (pMZ206). The sequence encoding for NarX$^{379to598}$ N509A was PCR amplified with PR3687/PR4972 from CMV-narX N509A (pMZ160). Both PCR products and the plasmid EF1α-V1-envZ-mCherry (pMZ194) digested with AgeI and XhoI were assembled using Gibson mix.

EF1α-V1-FKBP::narX$^{379to598}$ H399Q (pMZ229): The sequence encoding for FKBP and (G4S)2 linker was PCR amplified with PR4974/PR4973 from the plasmid CMV-FKBP::NarX$^{379to598}$ (pMZ214). The sequence encoding for NarX$^{379to598}$ H399Q was PCR amplified with PR3687/PR4972 from the plasmid CMV-narX H399Q (pEM014). Both PCR products and the plasmid EF1α-V1-envZ-mCherry (pMZ194) digested with AgeI and XhoI were assembled using Gibson mix.

EF1α-V1-FRB T2098L::narX$^{379to598}$ H399Q (pMZ230): The sequence encoding for FRB T2098L and (G4S)2 linker was PCR amplified with PR4975/PR4973 from the plasmid CMV-FRB T2098L::narX$^{379to598}$ (pMZ215). The sequence encoding for NarX$^{379to598}$ H399Q was PCR amplified with PR3687/PR4972 from the plasmid CMV-narX H399Q (pEM014). Both PCR products and the plasmid EF1α-V1-envZ-mCherry (pMZ194) digested with AgeI and XhoI were assembled using Gibson mix.

EF1α-V1-FKBP::narX$^{379to598}$ N509A (pMZ231): The sequence encoding for FKBP and (G4S)2 linker was PCR amplified with PR4974/PR4973 from the plasmid CMV-FKBP::narX$^{379to598}$ (pMZ214). The sequence encoding for NarX$^{379to598}$ N509A was PCR amplified with PR3687/PR4972 from the plasmid CMV-narX N509A (pMZ160). Both PCR products and the plasmid EF1α-V1-envZ-mCherry (pMZ194) digested with AgeI and XhoI were assembled using Gibson mix.

EF1α-V1-FRB T2098L::narX$^{379to598}$ N509A (pMZ232): The sequence encoding for FRB T2098L and (G4S)2 linker was PCR amplified with PR4975/PR4973 from the plasmid CMV-FRB T2098L::narX$^{379to598}$ (pMZ215). The sequence encoding for NarX$^{379to598}$ N509A was PCR amplified with PR3687/PR4972 from the plasmid CMV-narX N509A (pMZ160). Both PCR products and the plasmid EF1α-V1-envZ-mCherry (pMZ194) digested with AgeI and XhoI were assembled using Gibson mix.

EF1α-V1-narX (pMZ239): The sequence encoding for NarX was PCR amplified with PR3687/PR4979 from the plasmid CMV-narX (pJH002[14]). The PCR product and the plasmid EF1α-V1-envZ-mCherry (pMZ194) digested with AgeI and XhoI were assembled using Gibson mix EF1α-V1-narX$^{379to598}$ (pMZ241): The 3' fragment of narX was PCR amplified with PR4977/PR3687 from the plasmid CMV-narX (pJH002). The primers were designed to amplify the sequence from the 20th codon upstream the codon encoding for the phosphorylable histidine at the position 399 till the end of the gene and to insert the ATG sequence in front of this amplified sequence. The PCR product and the plasmid EF1α-V1-envZ-mCherry (pMZ194) digested with AgeI and XhoI were assembled using Gibson mix.

EF1α-V1-narX H399Q (pMZ242): The sequence encoding for NarX was PCR amplified with PR3687/PR4979 from the plasmid CMV-narX H399Q (pEM014[14]). The PCR product and the plasmid EF1α-V1-envZ-mCherry (pMZ194) digested with AgeI and XhoI were assembled using Gibson mix.

EF1α-V1-narX$^{379to598}$ H399Q (pMZ244): The 3' fragments of narX was PCR amplified with PR4977/PR3687 from the plasmid CMV-narX H399Q (pEM014). The primers were designed to amplify the sequence from the 20th codon upstream of the codon encoding for the phosphorylable histidine at the position 399 till the end of the gene and to insert the ATG sequence in front of this amplified sequence. The PCR product and the plasmid EF1α-V1-envZ-mCherry (pMZ194) digested with AgeI and XhoI were assembled using Gibson mix.

EF1α-V1-narX N509A (pMZ245): The sequence encoding for NarX was PCR amplified with PR3687/PR4979 from the plasmid CMV-narX N509A (pMZ160). The PCR product and the plasmid EF1α-V1-envZ-mCherry (pMZ194) digested with AgeI and XhoI were assembled using Gibson mix.

EF1α-V1-narX$^{379to598}$ N509A (pMZ247): The 3' fragment of narX was PCR amplified with PR4977/PR3687 from the plasmid CMV-narX N509A (pMZ160). The primers were designed to amplify the sequence from 20 codon upstream the codon encoding for the phosphorylable histidine at the position 399 to the end of the gene and to insert the ATG sequence in front of this amplified sequence. The PCR product and the plasmid EF1α-V1-envZ-mCherry (pMZ194) digested with AgeI and XhoI were assembled using Gibson mix.

EF1α-narL (pMZ248): The EF1α promoter was PCR amplified with PR4732/PR4978 from the plasmid pRA58 (Altamura et al, manuscript in preparation). The PCR product and the plasmid the plasmid CMV-narL (pJH004) digested with PspOMI and AgeI were assembled using Gibson mix EF1α-V1-narL (pMZ249): The EF1α-V1 promoter was PCR amplified with PR4734/PR4978 from the plasmid pRA114 (Altamura et al, manuscript in preparation). The PCR product and the plasmid the plasmid CMV-narL (pJH004) digested with PspOMI and AgeI were assembled using Gibson mix.

EF1α-V1-ARRB2::narX$^{379to598}$ (pMZ250): The sequence encoding for ARRB2 was PCR amplified with PR4980/PR4981 from the plasmid CMV-ARRB2::TEV protease (pBH302). The sequence encoding for NarX$^{379to598}$ was PCR amplified with PR3687/PR4982 from the plasmid CMV-narX (pJH2). The primers were designed to insert G4S linker between the amplified fragment. Both PCR products and EF1α-V1-envZ-mCherry the plasmid (pMZ194) digested with AgeI and XhoI were assembled using Gibson mix.

EF1α-V1-ARRB2::narX$^{379to598}$ H399Q (pMZ251): The sequence encoding for ARRB2 was PCR amplified with PR4980/PR4981 from the plasmid CMV-ARRB2::TEV protease (pBH302). The sequence encoding for NarX$^{379to598}$ H399Q was PCR amplified with PR3687/PR4982 from the plasmid CMV-narX H399Q (pEM014). The primers were designed to insert G4S linker between the amplified fragment. Both PCR products and the plasmid EF1α-V1-envZ-mCherry (pMZ194) digested with AgeI and XhoI were assembled using Gibson mix.

EF1α-V1-ARRB2::narX$^{3'}$N509A (pMZ252): The sequence encoding for ARRB2 was PCR amplified with PR4980/PR4981 from the plasmid CMV-ARRB2::TEV protease (pBH302). The sequence encoding for NarX$^{379to598}$ N509A was PCR amplified with PR3687/PR4982 from the plasmid CMV-narX N509A (pMZ160). The primers were designed to insert G4S linker between the amplified fragment. Both PCR products and the plasmid EF1α-V1-envZ-mCherry (pMZ194) digested with AgeI and XhoI were assembled using Gibson mix.

EF1α-V1-ADRB2$^{1to371}$::AVPR2$^{343to371}$::narX$^{379to598}$ H399Q (pMZ257): The sequence encoding for ADRB2$^{1to341}$::AVPR2$^{343to371}$ was PCR amplified with PR4983/PR4985 from the plasmid CMV-ADRB2$^{1to341}$::AVPR2$^{343to371}$::tTA (pBH312). The sequence encoding for NarX$^{379to598}$ H399Q was PCR amplified with PR3687/PR4982 from the plasmid CMV-narX H399Q (pEM014). The primers were designed to insert G4S linker between the amplified fragment. Both PCR products and the plasmid EF1α-V1-envZ-mCherry (pMZ194) digested with AgeI and XhoI were assembled using Gibson mix.

EF1α-V1-ADRB2$^{1to341}$::AVPR2$^{343to371}$::narX$^{379to598}$ N509A (pMZ258): The sequence encoding for ADRB2$^{1to341}$::AVPR2$^{343to371}$ was PCR amplified with PR4983/PR4985 from the plasmid CMV-ADRB2$^{1to341}$::AVPR2$^{343to371}$::tTA (pBH312). The sequence encoding for NarX$^{379to598}$ N509A was PCR amplified with PR3687/PR4982 from the plasmid CMV-narX N509A (pMZ160). The primers were designed to insert G4S linker between the amplified fragment. Both PCR products and the plasmid EF1α-V1-envZ-mCherry (pMZ194) digested with AgeI and XhoI were assembled using Gibson mix.

tTA_RE-cerulean (pMZ290): The promoter regulated by tTA was PCR amplified with PR5226/PR5227 from the plasmid tTA_RE-mCherry (pIM003[12]). The PCR product and the plasmid DcuR_RE-cerulean (pMZ259) digested with AscI and AgeI were assembled using Gibson mix.

EF1α-V1-ARRB2::TEV protease (pMZ291): The sequence encoding for ARRB2$^{283to409}$ and for the TEV protease was PCR amplified with PR5228/PR5229 from the plasmid CMV-ARRB2::TEV protease (pBH302). The sequence of the bGH poly(A) signal was PCR amplified with PR5230/PR5231 from the plasmid EF1α-V1-ARRB2::narX$^{379to598}$ (pMZ250). Both PCR products and the plasmid EF1α-V1-ARRB2::narX$^{379to598}$ (pMZ250) digested with BsaI and AvrII were assembled using Gibson mix.

EF1α::iRFP (pCS184): The iRFP coding sequence from CMV-iRFP (pCS12) was PCR amplified with PR2258/PR2259. The PCR product and the plasmid EF1α::citrine (pRA001, Altamura et al, manuscript in preparation) digested with BmtI and XbaI were assembled using ligation mix.

EF1α-V1-ADRB2$^{1to341}$::AVPR2$^{343to371}$::tTA (pBH292): The sequence encoding for ADRB2$^{254to341}$ AVPR2$^{343to371}$ and tTA was PCR amplified with PR5232/PR5233 from the plasmid CMV-ADRB2$^{1to341}$::AVPR2$^{343to371}$::tTA (pBH312). The PCR products and the the plasmid EF1α-V1-ADRB2$^{1to341}$::AVPR2$^{343to371}$::narX$^{379to598}$ H399Q (pMZ257) digested with BglII and XhoI were assembled using Gibson mix.

CMV-ARRB2::TEV protease (pBH302): the inventors performed de novo synthesis of gBlock sequence encoding for Beta-arrestin-2 fused with the TEV protease with 2 gBlock (gBlock112 and gBlock 113) via IDT. The gBlock and the plasmid pZsYellow1-N1 (Clontech 632445) digested with NotI and EcoRI were assembled using Gibson mix.

CMV-OPRK1$^{1to345}$::AVPR2$^{343to371}$::tTA (pBH309): Via IDT, the inventors performed de novo synthesis of gBlock (gBlock114) sequence encoding for KOR-1 and of gBlock (gBlock115) sequence encoding for V2R fused to tTA. The sequence encoding for KOR-1$^{1to345}$ was PCR amplified with PR2442/PR2443 from gBlock114. The PCR product, gBlock115 and the plasmid pZsYellow1-N1 (Clontech 632445) digested with XhoI and MfeI were assembled using Gibson mix.

CMV-ADRB2$^{1to341}$::AVPR2$^{343to371}$::tTA (pBH312): Via IDT, the inventors performed de novo synthesis of gBlock (gBlock118) sequence encoding for Beta-2 adrenergic receptor. The sequence encoding for ADRB2$^{1to341}$ was PCR amplified with PR2442/PR2444 from gBlock118. The PCR product and the plasmid CMV-OPRK1$^{1to345}$::

AVPR2$^{343to371}$::tTA (pBH309) digested with XhoI and BasHII were assembled using Gibson mix.

CMV-narX$^{176to598}$ (pJH010): The 3' fragment of narX was PCR amplified with PR1021/PR1023 from CMV-narX (pJH002). The primers were designed to amplify the sequence of NarX from the codon encoding the alanine at the position 176 to the end of the gene and to insert the ATG sequence in front of this amplified sequence. The PCR products and CMV-narX (pJH002) were digested with XhoI and AgeI. The two digested products are then ligated together.

The following plasmids were reported previously: CMV-envZ (pJH001), CMV-narX (pJH002), CMV-ompR (pJH003), CMV-narL (pJH004), OmpR_RE-AmCyan (pJH008), CMV-envZ_cyt (pJH009), CMV-envZ H243V (pEM013), CMV-narX H399Q (pEM014) and EnvZ-GGGGS-mCherry (pEM017) (Hansen, J. et al. *Proc Natl Acad Sci USA* 111, 15705-15710 (2014)). CBRN::FKBP and FRB::CBRC (Schramm, A. et al. *Int J Mol Sci* 19 (2018)). Ef1α-mCerulean (pKH024), Ef1α-citrine (pKH025) Ef1α-mCherry (pKH026) and Junk-DNA (pBH265) (Prochazka, et al., *Nat Commun* 5, 4729 (2014)). pTRE Bidirectional mCherry-pA (pIM003) (Angelici, B., et al., *Cell Rep* 16, 2525-2537 (2016)). The plasmid CMV-iRFP (pCS12) was obtained from Addgene (plasmid 31857 (Filonov, G. S. et al. *Angewandte Chemie International Edition* 51, 1448-1451 (2012))).

Cell Culture

The experiments in this work are performed on HEK293 purchased from Life technology (Cat #11631-017). Cell were cultured at 37° C., 5% $CO_2$ in DMEM (Gibco, Life Technologies; Cat #41966-052), supplemented with 10% FBS (Sigma-Aldrich; Cat #F9665) and with 1% Penicillin/Streptogamine Solution (Sigma-Aldrich, Cat #P4333). Splitting was performed every 3-4 days using 0.25% Trypsin-EDTA (Gibco, Life technologies; Cat #25200-072). Cultures were propagated for at most two months before being replaced by fresh cell stock.

Transfections

All transfections were performed using Lipofectamine 2000 Transfection Reagent (Life Technologies; Cat #11668027). All transfections were performed in 24-well plates (Thermo Scientific Nunc; NC-142475) and 400 ng of DNA was transfected. The cells were seeded 24 h before transfection at a density per well of 50 000 in 500 μl of DMEM. The plasmids for each sample were mixed as indicated in Supplementary Tables 3-18 and completed with the volume of Opti-MEM I Reduced Serum (Gibco, Life technologies Cat #31985-962) to have final volume of 50 μl. 1.5 μl of lipofectamine 2000 was diluted in 50 μl Opti-MEM I per sample to have a final amount of 3.75:1 μl Reagent/μg DNA ratio. After an incubation at least of 5 minutes the diluted Lipofectamine was added to the mixed DNA sample. The resulting mixture was briefly mixed by gentle vortexing and incubated 20 minutes at room temperature before being added to the cells. 4 hours after the DNA was added to the cells the medium was removed and replaced with 500 μl of fresh medium. When required 5 μl of the chemical tested were added to the medium. The different stock solution at 100× of the desired final concentration were prepared as indicated below:

A/C Heterodimerizer (Clontech; Cat #635057) stock solution was prepared in ethanol (Honeywell; Cat #02860): 250 μM, 50 μM, 20 μM, 8 μM, 3.2 μM, 1.28 μM, 512 nM, 205 nM, 81.9 nM, 32.8 nM, 13.1 nM, 5.24 nM, 1.04 nM.

Procaterol (Sigma; Cat #P9180-10MG) stock solution was prepared in DMSO (Sigma; Cat #D4540, BCBT0803): 1 mM, 286 μM, 81.6 μM, 23.3 μM, 10 μM, 6.6 μM, 1.9 μM, 544 nM, 155 nM, 44.4 nM and 12.7 nM Isoproterenol (Sigma; Cat #16504) stock solution was prepared in DMSO (Sigma; Cat #D4540): 1 mM, 286 μM, 81.6 μM, 23.3 μM, 6.6 μM, 1.9 μM, 544 nM, 155 nM, 44.4 nM and 12.7 nM Clenbuterol (Sigma; Cat #C5423) stock solution was prepared in DMSO (Sigma; Cat #D4540): 1 mM, 286 μM, 81.6 μM, 23.3 μM, 6.6 μM, 1.9 μM, 544 nM, 155 nM, 44.4 nM and 12.7 nM Propranolol (Sigma; Cat #P0884) stock solution was prepared in water (Invitrogen; Cat #10977-035): 1 mM, 286 μM, 81.6 μM, 23.3 μM, 6.6 μM, 1.9 μM, 544 nM, 155 nM, 44.4 nM and 12.7 nM Microscopy Microscopy images were taken from 48 h after transfection. The inventors used a Nikon Eclipse Ti microscope equipped with a mechanized stage and temperature control chamber held at 37° C. during the image acquisition. The excitation light was generated by a Nikon IntensiLight C-HGFI mercury lamp and filtered through a set of optimized Semrock filter cubes. The resulting images were collected by an Hamamatsu, ORCA R2 camera using a 10× objective. Each Semrock cube is assembled from an excitation filter, a dichroic mirror and an emission filter. In order to minimize the crosstalk between the different fluorescent proteins the inventors used the following setup: Cerulean: CFP HC (HC 438/24, BS 458, HC 483/32), mCherry: TxRed HC (HC 624/40, BS 593, HC 562/40). The images were acquired with an exposure of 40 ms for Cerulean and mCherry.

The acquired images were processed by ImageJ software performing uniform contrast-enhancement to improve visualization.

Flow Cytometry

The cells were prepared for FACS analysis 48 h after transfection by removing the medium and incubating the cells with 200 μl StemPro™ Accutase™ Cell Dissociation Reagent (Gibco, cat #A11105-01) at 37° C. for 5 minutes. After incubation, the plates was transferred on ice. To avoid potential cell damage the samples were prepared in successive batches so that no single sample was kept on ice for more than 1 h. The prepared samples were measured using a BD LSR Fortessa II Cell Analyzer with a combination of excitation and emission that minimizes the crosstalk between different fluorescent reporters. Cerulean was measured with a 445 nm laser and a 473/10 nm emission filter, mCherry with a 561 nm excitation laser coupled to a 600 nm longpass filter and 610/20 emission filter. The Cerulean and the mCherry were measured, respectively, at PMT voltage of 330 and 310 in all the experiments. SPHERO RainBow Calibration particles (Spherotech; Cat #RCP-30-5A, BD) were used to ensure constant device performance.

Data Analysis

General flow cytometry data analysis for bar charts was performed using FlowJo software. In this work, the fluorescence values in the bar charts, shown as normalized expression units (Cerulean, norm. u.) are calculated as follows. Live cells are gated based on their forward and side scatters readouts. From this population single cell are gated based on their forward scatters area and forward scatters height. Within this gate, cells positive in a Cerulean are gated based on a negative control such that 99.9% of cells in this control sample fall outside of the selected gate. For each Cerulean positive cell, the mean value of the fluorescent intensity is calculated and multiplied by the frequency of the positive cells. This value is used as a measure for the total reporter signal in a sample and can be defined as Total Intensity (TI). The TI of the Cerulean is normalized by the TI of mCherry-positive cells (constitutive transfection control). The relative formula is therefore: Reporter intensity in norm. u.=[mean (Reporter in Reporter+ cells)*Frequency (Reporter+ cells)]/[mean (Transfection Marker in Transfection Marker+ cells) *Frequency (Transfection Marker+ cells)].

Sequences

The nucleic and amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_315_29_seqlist, created Apr. 15, 2021, about 42 KB, which is incorporated by reference herein. In case that the sequences given below vary from the Sequence Listingsubmitted herewith in text format, the below sequences shall prevail.

TABLE 1

Primer Sequences

| Primer name | Sequence |
|---|---|
| PR1021 | GCTGCTGCTCTCGAGTCATTATCATTCGTGAGTGTC (SEQ ID NO 14) |
| PR1023 | GCTGCTACCGGTCGCCACCATGGCCCGCTTGCTCCAGCCGTGG (SEQ ID NO 15) |
| PR1964 | CGCGCCTGATTACAAAACTTTAAAAAGTGCTGTAGCGCCGGCTGATTACAAAACTTTAAA AAGTGCTGTCCA (SEQ ID NO 16) |
| PR1965 | TATGGACAGCACTTTTTAAAGTTTTGTAATCAGCCGGCGCTACAGCACTTTTTAAAGTTTT GTAATCAGG (SEQ ID NO 17) |
| PR2196 | TAAGCGGAATTCATCTTGGCTGAGGAATCTT (SEQ ID NO 18) |
| PR2197 | GCGAATTCTAGACTACTTGTACAGCTCGTCC (SEQ ID NO 19) |
| PR2258 | AATGTGAAGCTAGCGCCACCATGGCTGAAGGATCCGTCG (SEQ ID NO 20) |
| PR2259 | AATGTAATCTAGATCACTCTTCCATCACGCCGATC (SEQ ID NO 21) |
| PR2442 | GCTAGCGCTACCGGACTCAGAT (SEQ ID NO 22) |
| PR2443 | TGGGTGGGGTGCGTCCGCGCGCACAGAAGTCCCGGAAACACCG (SEQ ID NO 23) |
| PR2444 | TGGGTGGGGTGCGTCCGCGCGCACACAGAAGCTCCTGGAAGGCAA (SEQ ID NO 24) |
| PR3687 | GGCACAGTCGAGGCTGATTTTC (SEQ ID NO 25) |
| PR3707 | TGGCAGCGGGCGTCAAGCAG (SEQ ID NO 26) |
| PR3708 | ATGGTGGTGGCAGCGGCGAGGTATGGCAACG (SEQ ID NO 27) |
| PR3709 | CTCGCCGCTGCCACCACCATGTTGGCGACG (SEQ ID NO 28) |
| PR4122 | GAAATTAATACGACTCACTATAGGGGAC (SEQ ID NO 29) |
| PR4345 | GAAATTAATACGACTCACTATAGGGGACCGGTCGCCACCATGGCAGCGGGCGTCAAG (SEQ ID NO 30) |
| PR4346 | CACAGTCGAGGCTGATTTTC (SEQ ID NO 31) |
| PR4541 | GTTTGAGAGCTGCCGAGAGTGCTTCTCTCGCG (SEQ ID NO 32) |
| PR4542 | AGCACTCTCGGCAGCTCTCAAACATAGCCAGG (SEQ ID NO 33) |
| PR4543 | CTTCCAGTGCAGCTTCAATCAGATTTCCCAGTGTG (SEQ ID NO 34) |
| PR4544 | TCTGATTGAAGCTGCACTGGAAGCTCTGGGAC (SEQ ID NO 35) |
| PR4546 | GAAATTAATACGACTCACTATAGGGGACCGGTCGCCACCATGCAAGAGCGGCAGCAGC AG (SEQ ID NO 36) |
| PR4732 | GACGGCCAGTCTTAAGCTCGGGCCCGCTCCGGTGCCCGTCAG (SEQ ID NO 37) |
| PR4733 | GAAGTCGTCGCATGGTGGCGACCGGTTCACGACACCTGAAATGGAAG (SEQ ID NO 38) |
| PR4734 | GACGGCCAGTCTTAAGCTCGGGCCCTGGGCGGGATTCGTCTTG (SEQ ID NO 39) |
| PR4747 | CAAGAGCGGCAGCAGCAG (SEQ ID NO 40) |
| PR4748 | TTCGTGAGTGTCACCCTGC (SEQ ID NO 41) |
| PR4766 | GAAATTAATACGACTCACTATAGGGGACCGGTCGCCACCATGGGCGTGCAGGTGGAG (SEQ ID NO 42) |

TABLE 1-continued

| Primer Sequences | |
|---|---|
| Primer name | Sequence |
| PR4767 | CGCCACCGCCTGAACCGCCTCCACCTTCCAGTTTTAGAAGCTCCACATC (SEQ ID NO 43) |
| PR4769 | GAAATTAATACGACTCACTATAGGGGACCGGTCGCCACCATGGTAGCCATCCTCTGG (SEQ ID NO 44) |
| PR4770 | CGCCACCGCCTGAACCGCCTCCACCTGATATCCGTCTGAACACGTG (SEQ ID NO 45) |
| PR4771 | AGGCGGTTCAGGCGGTGGCGGGTCGCAAGAGCGGCAGCAGCAG (SEQ ID NO 46) |
| PR4892 | CGCGCCTACCCCTATAGGGGTATAGCGCCGGCTACCCCTATAGGGGTATCCA (SEQ ID NO 47) |
| PR4893 | TATGGATACCCCTATAGGGGTAGCCGGCGCTATACCCCTATAGGGGTAGG (SEQ ID NO 48) |
| PR4971 | TTCTTCCATTTCAGGTGTCGTGAACCGGTCGCCACCATGGGCTC (SEQ ID NO 49) |
| PR4972 | CATCGTCATGGAAGAGAGGGCGACTATTGC (SEQ ID NO 50) |
| PR4973 | GCAATAGTCGCCCTCTCTTCCATGACGATG (SEQ ID NO 51) |
| PR4974 | TTCTTCCATTTCAGGTGTCGTGAACCGGTCGCCACCATGGGCGT (SEQ ID NO 52) |
| PR4975 | TTCTTCCATTTCAGGTGTCGTGAACCGGTCGCCACCATGGTAGC (SEQ ID NO 53) |
| PR4977 | TTCTTCCATTTCAGGTGTCGTGAACCGGTCGCCACCATGCAAGAGCGGCAGCAGCAG (SEQ ID NO 54) |
| PR4978 | CCTGATTGGACATGGTGGCGACCGGTTCACGACACCTGA (SEQ ID NO 55) |
| PR4979 | TTCTTCCATTTCAGGTGTCGTGAACCGGTCGCCACCATGCTT (SEQ ID NO 56) |
| PR4980 | TCCATTTCAGGTGTCGTGAACCGGTCGCCACCATGGGGGAGAAACCCGGGAC (SEQ ID NO 57) |
| PR4981 | CTCTTGCGAGCCACCGCCACCGCAGAGTTGATCATCATAGTCGTC (SEQ ID NO 58) |
| PR4982 | GGTGGCGGTGGCTCGCAAGAGCGGCAGCAGCAG (SEQ ID NO 59) |
| PR4983 | TCCATTTCAGGTGTCGTGAACCGGTCGCCACCATGGGGCAACCCGGGAAC (SEQ ID NO 60) |
| PR4985 | CTCTTGCGAGCCACCGCCACCCGATGAAGTGTCCTTGGCC (SEQ ID NO 61) |
| PR5226 | ATTACGCCAAGCTACGGGGGCACCTCGACATACTCGAG (SEQ ID NO 62) |
| PR5227 | CCTTGCTCACCATGGTGGCGAGGTACCGAGCTCGAAATCTC (SEQ ID NO 63) |
| PR5228 | ACCGGGAGAAGCGGGGTCTCG (SEQ ID NO 64) |
| PR5229 | CAGTCGAGGCTGATTTTCTCGCTCAAGCGTAATCTGGAAC (SEQ ID NO 65) |
| PR5230 | GTTCCAGATTACGCTTGAGCGAGAAAATCAGCCTCGACTG (SEQ ID NO 66) |
| PR5231 | CCGGGAGCTTTTTGCAAAAGC (SEQ ID NO 67) |
| PR5232 | GGACGGGGCATGGACTCCGCAG (SEQ ID NO 68) |
| PR5233 | GCACAGTCGAGGCTGATTTTCTCGAGTCATTACTACCCACCGTACTCGTCAATTCC (SEQ ID NO 69) |

TABLE 2

| List of synthetic DNA used for plasmid constructs | |
|---|---|
| Synthetic DNA name | Sequence |
| gBlock112 | agatctcgagctcaagcttcGAATTCGCCACCatgggggagaaacccgggaccagggtcttcaagaagtcgagc cctaactgcaagctcaccgtgtacttgggcaagcgggacttcgtagatcacctggacaaagtggaccctgtagatggcgtgg |

TABLE 2-continued

| Synthetic DNA name | Sequence |
|---|---|
| List of synthetic DNA used for plasmid constructs | |
| | tgcttgtggaccctgactacctgaaggaccgcaaagtgtttgtgaccctcacctgcgccttccgctatggccgtgaagacctgg<br>atgtgctgggcttgtccttccgcaaagacctgttcatcgccacctaccaggccttccccccggtgcccaacccaccccggccc<br>cccacccgcctgcaggaccggctgctgaggaagctgggccagcatgcccacccccttcttcttcaccataccccagaatcttc<br>catgctccgtcacactgcagccaggcccagaggatacaggaaaggcctgcggcgtagactttgagattcgagccttctgtg<br>ctaaatcactagaagagaaaagccacaaaaggaactctgtgcggctggtgatccgaaaggtgcagttcgccccggagaa<br>acccggcccccagccttcagccgaaaccacacgccacttcctcatgtctgaccggtccctgcacctcgaggcttccctggac<br>aaggagctgtactaccatggggagcccctcaatgtaaatgtccacgtcaccaacaactccaccaagaccgtcaagaagat<br>caaagtctctgtgagacagtacgccgacatctgcctcttcagcaccgcccagtacaagtgtcctgtggctcaactcgaacaa<br>gatgaccaggtatctcccagctccacattctgtaaggtgtacaccataaccccactgctcagcgacaaccgggagaagcgg<br>ggtctcgccctggatgggaaactcaagcacgaggacaccaacctggcttccagcaccatcgtgaaggagggtgccaaca<br>aggaggtgctgggaatcctggtgtcct (SEQ ID NO 70) |
| gBlock113 | gctgggaatcctggtgtcctacagggtcaaggtgaagctggtggtgtctcgaggcggggatgtctctgtggagctgccttttgtt<br>cttatgcaccccaagccccacgaccacatccccctccccagaccccagtcagccgctccggagacagatgtccctgtgga<br>caccaacctcattgaatttgataccaactatgccacagatgatgacattgtgtttgaggactttgcccggcttcggctgaaggg<br>gatgaAGGATGACGACTATGATGATCAACTCTGCGGATCCagcttgtttaagggaccacgtgattac<br>aacccgatatcgagcaccatttgtcatttgacgaatgaatctgatgggcacacaacatcgttgtatggtattggatttggtccctt<br>catcattacaaacaagcacttgtttagaagaaataatggaacactgttggtccaatcactacatggtgtattcaaggtcaaga<br>acaccacgactttgcaacaacacctcattgatgggagggacatgataattattcgcatgcctaaggatttcccaccatttcctc<br>aaaagctgaaatttagagagccacaaagggaagagcgcatatgtcttgtgacaaccaacttccaaactaagagcatgtcta<br>gcatggtgtcagacactagttgcacattcccttcatctgatggcatattctggaagcattggattcaaaccaaggatgggcagt<br>gtggcagtccattagtatcaactagagatgggttcattgttggtatacactcagcatcgaatttcaccaacacaaacaattatttc<br>acaagcgtgccgaaaaacttcatggaattgttgacaaatcaggaggcgcagcagtgggttagtggttggcgattaaatgctg<br>actcagtattgtgggggggccataaagttttcatgagcaaacctgaagagccttttcagccagttaaggaagcgactcAAC<br>TCATGAATGAATTGGTGTACTCGCAATACCCATACGATGTTCCAGATTACGCTTGAgc<br>GGCCGCgactctagatcataatcag (SEQ ID NO 71) |
| gBlock114 | GcgctaccggactcagatctcgagGCCACCatggactccccgatccagatcttccgcggggagccgggccctacctg<br>cgcccgagcgcctgcctgcccccaacagcagcgcctggtttcccggctgggccgagcccgacagcaacggcagcgc<br>cggctcggaggacgcgcagctggagcccgcgcacatctccccggccatcccggtcatcatcacggcggtctactccgtagt<br>gttcgtcgtgggcttggtgggcaactcgctggtcatgttcgtgatcatccgatacacaaagatgaagacagcaaccaacattt<br>acatatttaacctggctttggcagatgctttagttactacaaccatgccctttcagagtacggtctacttgatgaattcctggcctttt<br>ggggatgtgctgtgcaagatagtaatttccattgattactacaacatgttcaccagcatcttcaccttgaccatgatgagcgtgg<br>accgctacattgccgtgtgccaccccgtgaaggctttggacttccgcacacccttgaaggcaaagatcatcaatatctgcatct<br>ggctgctgtcgtcatctgttggcatctctgcaatagtccttggaggcaccaaagtcagggaagacgtcgatgtcattgagtgct<br>ccttgcagttcccagatgatgactactcctggtgggacctcttcatgaagatctgcgtcttcatctttgccttcgtgatccctgtcctc<br>atcatcatcgtctgctacaccctgatgatcctgcgtctcaagagcgtccggctcctttctggctcccgagagaaagatcgcaac<br>ctgcgtaggatcaccagactggtcctggtggtggtggcagtcttcgtcgtctgctggactcccattcacatattcatcctggtgga<br>ggctctggggagcacctcccacagcacagctgctctctccagctattacttctgcatcgccttaggctataccaacagtagcct<br>gaatcccattctctacgcctttcttgatgaaaacttcaagcggtgtttccgggacttctgTtttccactgaagatgaggatggagc<br>ggcagagcactagcagagtccgaaatacagttcaggaCcctgcttacctgagggacatcgatgggatgaataaaccagt<br>atgacaattgttgttgttaacttgtttattgc (SEQ ID NO 72) |
| gBlock115 | AGCGGTGTTTCCGGGACTTCTGTGCGCGCggacgcaccccacccagcctgggtccccaagatgagtc<br>ctgcaccaccgccagctcctccccTGGCCAAGGACACTTCATCGGGATCCGAGAATCTGTACTTT<br>CAGCTGagattagataaaagtaaagtgattaacagcgcattagagctgcttaatgaggtcggaatcgaaggtttaacaa<br>cccgtaaactcgcccagaagctaggtgtagagcagcctacattgtattggcatgtaaaaaataagcgggctttgctcgacgc<br>cttagccattgagatgttagataggcaccatactcacttttgccctttagaaggggaaagctggcaagattttttacgtaataacg<br>ctaaaagttttagatgtgctttactaagtcatcgcgatggagcaaaagtacatttaggtacacggcctacagaaaaacagtat<br>gaaactctcgaaaatcaattagcctttttatgccaacaaggtttttcactagagaatgcattatatgcactcagcgctgtggggc<br>atttactttaggttgcgtattggaagatcaagagcatcaagtcgctaaagaagaaagggaaacacctactactgatagtatg<br>ccgccattattacgacaagctatcgaattatttgatcaccaaggtgcagagccagccttcttattcggccttgaattgatcatatg<br>cggattagaaaaacaacttaaatgtgaaagtgggtccgcgtacagccgGgcgcgtacgaaaaacaattacgggtctacc<br>atcgagggcctgctcgatctccccggacgacgacgcccccgaagaggcggggctggcggctccgcgcctgtcctttctcccc<br>gcgggacacacgcgcagactgtcgacggcccccccgaccgatgtcagcctgggggacgagctccacttagacggcgag<br>gacgtggcgatggcgcatgccgacgcgctagacgatttcgatctggacatgttgggggacggggattccccgggtccggg<br>atttaccccccacgactccgccccctacggcgctctggatatggccgacttcgagtttgagcagatgtttaccgatgcccTTG<br>GAATTGACGAGTACGGTGGGTAGcaattgttgttgttaacttgtttattgc (SEQ ID NO 73) |
| gBlock118 | gctagcgctaccggactcagatctcgagGCCACCatggggcaacccgggaacggcagcgccttcttgctggcaccca<br>atagaagccatgcgccggaccacgacgtcacgcagcaaagggacgaggtgtgggtggtgggcatgggcatcgtcatgtc<br>tctcatcgtcctggccatcgtgtttggcaatgtgctggtcatcacagccattgccaagttcgagcgtctgcagacggtcaccaac<br>tacttcatcacttcactggcctgtgctgatctggtcatgggcctggcagtggtgccctttggggccgcccatattcttatgaaaatg<br>tggacttttggcaacttctggtgcgagttttggacttccattgatgtgctgtgcgtcacggccagcattgagaccctgtgcgtgatc<br>gcagtggatcgctactttgccattacttcacctttcaagtaccagagcctgctgaccaagaataaggcccgggtgatcattctg<br>atggtgtggattgtgtcaggccttacctccttcttgcccattcagatgcactggtaccgggccacccaccaggaagccatcaac<br>tgctatgccaatgagacctgctgtgacttcttcacgaaccaagcctatgccattgcctcttccatcgtgtccttctacgttcccctg<br>gtgatcatggtcttcgtctactccagggtctttcaggaggccaaaaggcagctccagaagattgacaaatctgagggccgctt<br>ccatgtccagaaccttagccaggtggagcaggatgggcggacggggcatggactccgcagatcttccaagttctgcttgaa<br>ggagcacaaagccctcaagacgttaggcatcatcatgggcactttcaccctctgctggctgcccttcttcatcgttaacattgtg<br>catgtgatccaggataacctcatccgtaaggaagtttacatcctcctaaattggataggctatgtcaattctggtttcaatcccctt<br>atctactgccggagcccagatttcaggattgccttccaggagcttctgtgTctgcgcaggtcttctttgaaggcctatgggaatg<br>gctactccagcaacggcaacacaggggagcagagtggatatcacgtggaacaggagaaagaaaataaactgctgtgtg<br>aagacctcccaggcacggaagactttgtgggccatcaaggtactgtgcctagcgataacattgattcacaagggaggaatt<br>gtagtacaaatgactcactgctgtaacaattgttgttgttaacttgtttattgc (SEQ ID NO 74) |

TABLE 2-continued

List of synthetic DNA used for plasmid constructs

| Synthetic DNA name | Sequence |
| --- | --- |
| gBlock143 | ATCTTGGCTGAGGAATCTTCTAACAATTTAGAGCTTAAAAACGCCCACGAGGCGGAG AACGAAATATCCAGAGAGACGTTAGAAACGTTCAAAAACGTTCGCTAGCGCCACCAT GGTGAGCAAGGGCGAGGAGCTGTTCACCGGGGTGGTGCCCATCCTGGTCGAGCTG GACGGCGACGTAAACGGCCACAAGTTCAGCGTGTCCGGCGAGGGCGAGGGCGATG CCACCTACGGCAAGCTGACCCTGAAGTTCATCTGCACCACCGGCAAGCTGCCCGTG CCCTGGCCCACCCTCGTGACCACCTTCGGCTACGGCCTGATGTGCTTCGCCCGCTA CCCCGACCACATGAAGCAGCACGACTTCTTCAAGTCCGCCATGCCCGAAGGCTACG TCCAGGAGCGCACCATCTTCTTCAAGGACGACGGCAACTACAAGACCCGCGCCGAG GTGAAGTTCGAGGGCGACACCCTGGTGAACCGCATCGAGCTGAAGGGCATCGACTT CAAGGAGGACGGCAACATCCTGGGGCACAAGCTGGAGTACAACTACAACAGCCACA ACGTCTATATCATGGCCGACAAGCAGAAGAACGGCATCAAGGTGAACTTCAAGATCC GCCACAACATCGAGGACGGCAGCGTGCAGCTCGCCGACCACTACCAGCAGAACAC CCCCATCGGCGACGGCCCCGTGCTGCTGCCCGACAACCACTACCTGAGCTACCAGT CCAAGCTGAGCAAAGACCCCAACGAGAAGCGCGATCACATGGTCCTGCTGGAGTTC GTGACCGCCGCCGGGATCACTCTCGGCATGGACGAGCTGTACAAGTAG (SEQ ID NO 75) |
| gBlock264 | gaaattaatacgactcactataggggaccggtcgccaccATGGGCTCGAGCAACCTGGTTGCGCAGCT CGAAAACGAAGTTGCGTCTCTGGAAAATGAGAACGAAACCCTGAAGAAAAAGAACCT GCACAAAAAAGACCTGATCGCGTACCTGGAGAAAGAAATCGCGAATCTGCGTAAGA AAATCGAAGAAGGCGGTGGCGGGTCGCAAGAGCGGCAGCAGCAGCT (SEQ ID NO 76) |
| gBlock265 | TGCAGGGTGACACTCACGAAGGCGGTGGCGGGTCGAACCTGGTTGCGCAGCTCGA AAACGAAGTTGCGTCTCTGGAAAATGAGAACGAAACCCTGAAGAAAAAGAACCTGCA CAAAAAAGACCTGATCGCGTACCTGGAGAAAGAAATCGCGAATCTGCGTAAGAAAAT CGAAGAATGATAATGACTCGAGAAAATCAGCCTCGACTGTG (SEQ ID NO 77) |
| gBlock269 | gaaattaatacgactcactataggggaccggtcgccaccATGGGCTCGAGCGCGCGTAACGCGTATCT GCGTAAGAAAATCGCACGTCTGAAAAAAGACAACCTGCAGCTGGAACGTGATGAAC AGAACCTGGAAAAAATCATCGCGAACCTGCGTGACGAAATCGCGCGTCTCGAAAAC GAAGTTGCGTCTCACGAACAGGGCGGTGGCGGGTCGCAAGAGCGGCAGCAGCAGC T (SEQ ID NO 78) |
| gBlock270 | TGCAGGGTGACACTCACGAAGGCGGTGGCGGGTCGGCGCGTAACGCGTATCTGCG TAAGAAAATCGCACGTCTGAAAAAAGACAACCTGCAGCTGGAACGTGATGAACAGAA CCTGGAAAAAATCATCGCGAACCTGCGTGACGAAATCGCGCGTCTCGAAAACGAAG TTGCGTCTCACGAACAGTGATAATGACTCGAGAAAATCAGCCTCGACTGTG (SEQ ID NO 79) |

The sequences of the synthetic promoters are indicated in the following table (underlinded sequences indicates the RR DNA binding sites, italic letters indicate the TATA Box. Start codon is shown in bold)

| | |
| --- | --- |
| OmpR RE (SEQ ID 1) | ATTTACATTTTGAAACATCTATAGCGCCGGCATTTACATTTTGAAACATC TATCCATATGCTCTAGAGGG*TATATAA*TGGGGGCCACTAGTCTACTACC AGAGCTCATCGCTAGCGCTACCGGTCGCCACC**ATG** |
| NarL RE (SEQ ID 2) | TACCCCTATAGGGGTATAGCGCCGGCTACCCCTATAGGGGTATCCATA TGCTCTAGAGGG*TATATAA*TGGGGGCCACTAGTCTACTACCAGAGCTCA TCGCTAGCGCTACCGGTCGCCACC**ATG** |

The sequence of the promoter CMV, EF1α, and EF1α-V1

>CMV promoter (SEQ ID 3)

gcgttgacattgattattgactagttattaatagtaatcaattacggggtcattagttcatagcccatatatggagttccgcgttacataa cttacggtaaatggcccgcctggctgaccgcccaacgacccccgcccattgacgtcaataatgacgtatgttcccatagtaacgc caatagggactttccattgacgtcaatgggtggagtatttacggtaaactgcccacttggcagtacatcaagtgtatcatatgccaa gtacgccccctattgacgtcaatgacggtaaatggcccgcctggcattatgcccagtacatgaccttatgggactttcctacttggca gtacatctacgtattagtcatcgctattaccatggtgatgcggttttggcagtacatcaatgggcgtggatagcggtttgactcacggg -continued gatttccaagtctccaccccattgacgtcaatgggagtttgttttggcaccaaaatcaacgggactttccaaaatgtcgtaacaactc cgccccattgacgcaaatgggcggtaggcgtgtacggtgggaggtctatataagcagagctctctggctaact

>EF1α

(SEQ ID 4)

GCTCCGGTGCCCGTCAGTGGGCAGAGCGCACATCGCCCACAGTCCCCGAGAAGTTGG

GGGGAGGGGTCGGCAATTGAACCGGTGCCTAGAGAAGGTGGCGCGGGGTAAACTGGG

AAAGTGATGTCGTGTACTGGCTCCGCCTTTTTCCCGAGGGTGGGGGAGAACCGTATAT

AAGTGCAGTAGTCGCCGTGAACGTTCTTTTTCGCAACGGGTTTGCCGCCAGAACACAG

GTAAGTGCCGTGTGTGGTTCCCGCGGGCCTGGCCTCTTTACGGGTTATGGCCCTTGCG

TGCCTTGAATTACTTCCACGCCCCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGT

GCTTGAGTTGAGGCCTGGCCTGGGCGCTGGGGCCGCCGCGTGCGAATCTGGTGGCAC

CTTCGCGCCTGTCTCGCTGCTTTCGATAAGTCTCTAGCCATTTAAAATTTTTGATGACCT

GCTGCGACGCTTTTTTTCTGGCAAGATAGTCTTGTAAATGCGGGCCAAGATCTGCACAC

TGGTATTTCGGTTTTTGGGGCCGCGGGCGGCGACGGGGCCCGTGCGTCCCAGCGCAC

ATGTTCGGCGAGGCGGGGCCTGCGAGCGCGGCCACCGAGAATCGGACGGGGGTAGT

CTCAAGCTGGCCGGCCTGCTCTGGTGCCTGGCCTCGCGCCGCCGTGTATCGCCCCGC

CCTGGGCGGCAAGGCTGGCCCGGTCGGCACCAGTTGCGTGAGCGGAAAGATGGCCG

CTTCCCGGCCCTGCTGCAGGGAGCTCAAAATGGAGGACGCGGCGCTCGGGAGAGCGG

GCGGGTGAGTCACCCACACAAAGGAAAAGGGCCTTTCCGTCCTCAGCCGTCGCTTCAT

GTGACTCCACGGAGTACCGGGCGCCGTCCAGGCACCTCGATTAGTTCTCGAGCTTTTG

GAGTACGTCGTCTTTAGGTTGGGGGGAGGGGTTTTATGCGATGGAGTTTCCCCACACT

GAGTGGGTGGAGACTGAAGTTAGGCCAGCTTGGCACTTGATGTAATTCTCCTTGGAATT

TGCCCTTTTTGAGTTTGGATCTTGGTTCATTCTCAAGCCTCAGACAGTGGTTCAAAGTTT

TTTTCTTCCATTTCAGGTGTCGTGA

>EF1α-V1

(SEQ ID 5)

ttaagctcgggcccTGGGCGGGATTCGTCTTGGGCGGGATCCTTGTCCACGTGATCGGGGGA

GGGACTTTCCCGCTGGAGTGACTCATCTAGCCCACGTGATCTTCATGCCACGTGATCGA

TATGGGGACTTTCCTGACTCCCACGTGATCGCACCCCCACGTGATCCCGTAAGGGACT

TTCCCTACTTTGCCTAGAGAAGGTGGCGCGGGGTAAACTGGGAAAGTGATGTCGTGTA

CTGGCTCCGCCTTTTTCCCGTGCTCAGGGGAGAACCGTATATAAGTGCAGTAGTCGCC

GTGAACGTTCTTTTTCGCAACGTTAACTAGCACAGAACACAGGTAAGTGCCGTGTGTGG

TTCCCGCGGGCGGCGACGGGGCCCGTGCCCACGTGATCAGGAGTTGGGCGGGATGTT

ATGAGTGACTCACGCCATCCACGTGATCTCAGACGGGACTTTCCATATTAAGTGACTCA

GGATAAGGGACTTTCCCTACGGCCACGTGATCTCTTTTTGGGCGGGATGAGATTGGGA

CTTTCCTGTCCTGGGACTTTCCTACAGTTCAAACTCGACCACGTGATCTTATGACTGACG

GGCGGGTGAGTCACCCACGGTGGCATGGGGGACTTTCCTTTAGGCGTTCATGTGACTC

CACGGACAAGCCTCAGACAGTGGTTCAAAGTTTTTTTCTTCCATTTCAGGTGTCGTGAa

The sequence of narL:
>NarL (SEQ ID 6)

MSNQEPATILLIDDHPMLRTGVKQLISMAPDITVVGEASNGEQGIELAESLDPDLILLD

LNMPGMNGLETLDKLREKSLSGRIVVFSVSNHEEDVVTALKRGADGYLLKDMEPED

-continued

LLKALHQAAAGEMVLSEALTPVLAASLRANRATTERDVNQLTPRERDILKLIAQGLP

NKMIARRLDITESTVKVHVKHMLKKMKLKSRVEAAVWVHQERIF

The sequence of VP48
>VP48

(SEQ ID 7)

GPADALDDFDLDMLPADALDDFDLDMLPADALDDFDLDMLPG

The aa sequence of EnvZ$^{180to450}$, EnvZ$^{223to450}$, NarX$^{176to598}$ and NarX$^{379to598}$ are indicated below the phosphorylatable histidine is underlined and italic, the asparagine important for the ATP binding domain is bold and underlined
>EnvZ$^{180to450}$ (SEQ ID 8)

MRIQNRPLVDLEHAALQVGKGIIPPPLREYGASEVRSVTRAFNHMAAGVKQLADDRTLLMA

GVS*H*DLRTPLTRIRLATEMMSEQDGYLAESINKDIEECNAIIEQFIDYLRTGQEMPMEMADLN

AVLGEVIAAESGYEREIETALYPGSIEVKMHPLSIKRAVANMVVNAARYGNGWIKVSSGTEP

NRAWFQVEDDGPGIAPEQRKHLFQPFVRGDSARTISGTGLGLAIVQRIVDNHNGMLELGTS

ERGGLSIRAWLPVPVTRAQGTTKEG

>EnvZ$^{223to450}$ (SEQ ID 9)

MAAGVKQLADDRTLLMAGVS*H*DLRTPLTRIRLATEMMSEQDGYLAESINKDIEECNAIIEQFI

DYLRTGQEMPMEMADLNAVLGEVIAAESGYEREIETALYPGSIEVKMHPLSIKRAVANMVVN

AARYGNGWIKVSSGTEPNRAWFQVEDDGPGIAPEQRKHLFQPFVRGDSARTISGTGLGLAI

VQRIVDNHNGMLELGTSERGGLSIRAWLPVPVTRAQGTTKEG

>NarX$^{176to598}$ (SEQ ID 10)

MARLLQPWRQLLAMASAVSHRDFTQRANISGRNEMAMLGTALNNMSAELAESYAVLEQRV

QEKTAGLEHKNQILSFLWQANRRLHSRAPLCERLSPVLNGLQNLTLLRDIELRVYDTDDEEN

HQEFTCQPDMTCDDKGCQLCPRGVLPVGDRGTTLKWRLADSHTQYGILLATLPQGRHLSH

DQQQLVDTLVEQLTATLALDRHQERQQQLIVMEERATIAREL*H*DSIAQSLSCMKMQVSCLQ

MQGDALPESSRELLSQIRNELNASWAQLRELLTTFRLQLTEPGLRPALEASCEEYSAKFGFP

VKLDYQLPPRLVPSHQAIHLLQIAREALSNALKHSQASEVVVTVAQNDNQVKLTVQDNGCG

VPENAIRSNHYGMIIMRDRAQSLRGDCRVRRRESGGTEVVVTFIPEKTFTDVQGDTHE

>NarX$^{379to598}$ (SEQ ID 11)

MQERQQQLIVMEERATIAREL*H*DSIAQSLSCMKMQVSCLQMQGDALPESSRELLSQIRNEL

NASWAQLRELLTTFRLQLTEPGLRPALEASCEEYSAKFGFPVKLDYQLPPRLVPSHQAIHLL

QIAREALSNALKHSQASEVVVTVAQNDNQVKLTVQDNGCGVPENAIRSNHYGMIIMRDRAQ

SLRGDCRVRRRESGGTEVVVTFIPEKTFTDVQGDTHE

The aa of the mutated version of NarX379to598 the mutated aa is indicated in bold and underlined
>NarX$^{379to598}$ (H399Q)

(SEQ ID 12)

MQERQQQLIVMEERATIARELQDSIAQSLSCMKMQVSCLQMQGDALPESSRELLSQIRNEL

NASWAQLRELLTTFRLQLTEPGLRPALEASCEEYSAKFGFPVKLDYQLPPRLVPSHQAIHLL

QIAREALSNALKHSQASEVVVTVAQNDNQVKLTVQDNGCGVPENAIRSNHYGMIIMRDRAQ

SLRGDCRVRRRESGGTEVVVTFIPEKTFTDVQGDTHE

>NarX$^{379to598}$ (N509A)

(SEQ ID 13)

MQERQQQLIVMEERATIARELHDSIAQSLSCMKMQVSCLQMQGDALPESSRELLSQIRNEL

NASWAQLRELLTTFRLQLTEPGLRPALEASCEEYSAKFGFPVKLDYQLPPRLVPSHQAIHLL

QIAREALSAALKHSQASEVVVTVAQNDNQVKLTVQDNGCGVPENAIRSNHYGMIIMRDRAQ

SLRGDCRVRRRESGGTEVVVTFIPEKTFTDVQGDTHE

The invention claimed is:

1. A mammalian cell comprising a first nucleic acid sequence encoding a first polypeptide fused to the N-terminus of a first variant of a histidine kinase comprising a dimerization and histidine-containing phosphotransfer (DHp) domain and a catalytic ATP-binding (CA) domain, wherein the first variant of the histidine kinase is a truncation variant that comprises neither a histidine kinase sensor domain nor a histidine kinase transmitter domain;

a second nucleic acid sequence encoding a second polypeptide fused to the N-terminus of a second variant of said histidine kinase comprising a DHp domain and a CA domain, wherein the second variant of the histidine kinase is a truncation variant that comprises neither a histidine kinase sensor domain nor a histidine kinase transmitter domain; and a third nucleic acid sequence encoding a response regulatory protein specifically phosphorylatable by said DHp domain of said first or said second variant, wherein the histidine kinase belongs to the transphosphorylation family, wherein, upon specific binding of said first polypeptide and said second polypeptide, said first and second variants dimerize such that said CA domain of said first or second variant phosphorylates said DHp domain of said first or second variant, and the activity of said response regulatory protein is modulated by phosphorylation by said DHp domain of said first and/or second variant, and wherein:

(a) each of said first and second variants comprises an amino acid sequence of SEQ ID NO: 11; or (b) said first variant comprises an amino acid sequence of SEQ ID NO: 12, and said second variant comprises an amino acid sequence of SEQ ID NO: 13.

2. The mammalian cell according to claim 1, wherein said response regulatory protein comprises a receiver domain fused to an effector domain, wherein said receiver domain is phosphorylatable by said DHp domain of said first and/or said second variant, and said effector domain is activatable or inhibitable by the phosphorylated receiver domain.

3. The mammalian cell according to claim 2, wherein said effector domain is a transcriptional activating domain, and said mammalian cell comprises a fourth nucleic acid comprising a gene of interest under control of an inducible promoter recognizable by said transcriptional activating domain, and wherein upon activation of said transcriptional activating domain the expression of said gene of interest is induced.

4. The mammalian cell according to claim 3, wherein said inducible promoter is NarL-RE (SEQ ID NO; 2).

5. The mammalian cell according to claim 3, wherein said gene of interest encodes an immunoprotein or a microRNA that affects the mammalian cell's function or internal state.

6. The mammalian cell according to claim 2, wherein said receiver domain comprises or is a NarL response regulatory protein (SEQ ID NO: 6), and said effector domain is or comprises a VP16 transcriptional activation domain (Vp48, SEQ ID NO: 7).

7. The mammalian cell according to claim 1, wherein each of said first and second variants comprises an amino acid sequence of SEQ ID NO: 11.

8. The mammalian cell according to claim 1, wherein said first nucleic acid sequence and/or said second nucleic acid sequence and/or said third nucleic acid sequence is under transcriptional control of a constitutive promoter.

9. The mammalian cell according to claim 8, wherein said constitutive promoter is selected from CMV (SEQ ID NO; 3), EF1α (SEQ ID NO: 4), and EF1α-V1 (SEQ ID NO; 5).

10. The mammalian cell according to claim 1, wherein said first variant and said second variant are identical.

11. The mammalian cell according to claim 1, wherein said first variant comprises a DHp domain that does not comprise a histidine residue accessible by said CA domain of first or said second variant of said histidine kinase, and/or said second variant comprises a CA domain that is not able to bind ATP.

12. The mammalian cell according to claim 1, wherein said first variant comprises an amino acid sequence of SEQ ID NO: 12, and said second variant comprises an amino acid sequence of SEQ ID NO: 13.

13. The mammalian cell according to claim 1, wherein specific binding of said first polypeptide and said second polypeptide is triggerable by a ligand specifically recognizable by said first and/or said second polypeptide.

14. The mammalian cell according to claim 13, wherein said first polypeptide is or comprises a receptor and said second polypeptide is or comprises a binding partner of said receptor, wherein binding of said receptor and said binding partner is triggerable by said ligand recognizable by said receptor.

15. The mammalian cell according to claim 14, wherein said receptor is a transmembrane receptor, and said binding partner is a cytosolic protein.

16. The mammalian cell according to claim 1, wherein said first polypeptide consists of or comprises a G-protein coupled receptor and said second polypeptide consists of or comprises a cytosolic ligand of said G-protein coupled receptor, or said first polypeptide consists of or comprises a T cell receptor and said second polypeptide is or comprises ZAP-70.

17. The mammalian cell according to claim 1, wherein said first variant and said second variant are unable to dimerize on their own in the absence of said first and second polypeptides.

18. The mammalian cell according to claim 1, wherein formation of a heterodimer of said first variant and said second variant is required to modulate the activity of said response regulatory protein.

* * * * *

SEQUENCE LISTING

<160> NUMBER OF SEQ ID NOS: 79

<210> SEQ ID NO 1
<211> LENGTH: 134
<212> TYPE: DNA
<213> ORGANISM: Artificial Sequence
<220> FEATURE:
<223> OTHER INFORMATION: synthetic promoter

<400> SEQUENCE: 1
atttacattt tgaaacatct atagcgccgg catttacatt ttgaaacatc tatccatatg 60
ctctagaggg tatataatgg gggccactag tctactacca gagctcatcg ctagcgctac 120
cggtcgccac catg 134

<210> SEQ ID NO 2
<211> LENGTH: 124
<212> TYPE: DNA
<213> ORGANISM: Artificial Sequence
<220> FEATURE:
<223> OTHER INFORMATION: synthetic promoter

<400> SEQUENCE: 2 taccccctata ggggtatagc gccggctacc cctatagggg tatccatatg ctctagaggg 60
tatataatgg gggccactag tctactacca gagctcatcg ctagcgctac cggtcgccac 120
catg 124

<210> SEQ ID NO 3
<211> LENGTH: 601
<212> TYPE: DNA
<213> ORGANISM: Cytomegalovirus

<400> SEQUENCE: 3
gcgttgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga gtatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatggtgat gcggttttgg cagtacatca atgggcgtgg 420
atagcggttt gactcacggg gatttccaag tctccacccc attgacgtca atgggagttt 480
gttttggcac caaaatcaac gggactttcc aaaatgtcgt aacaactccg ccccattgac 540
gcaaatgggc ggtaggcgtg tacggtggga ggtctatata agcagagctc tctggctaac 600
t 601

<210> SEQ ID NO 4
<211> LENGTH: 1182
<212> TYPE: DNA
<213> ORGANISM: Homo sapiens

<400> SEQUENCE: 4
gctccggtgc ccgtcagtgg gcagagcgca catcgcccac agtccccgag aagttggggg 60
gaggggtcgg caattgaacc ggtgcctaga gaaggtggcg cggggtaaac tgggaaagtg 120
atgtcgtgta ctggctccgc ctttttcccg agggtggggg agaaccgtat ataagtgcag 180
tagtcgccgt gaacgttctt tttcgcaacg ggtttgccgc cagaacacag gtaagtgccg 240
tgtgtggttc ccgcgggcct ggcctcttta cgggttatgg cccttgcgtg ccttgaatta 300
cttccacgcc cctggctgca gtacgtgatt cttgatcccg agcttcgggt tggaagtggg 360
tgggagagtt cgaggccttg cgcttaagga gccccttcgc ctcgtgcttg agttgaggcc 420
tggcctgggc gctggggccg ccgcgtgcga atctggtggc accttcgcgc ctgtctcgct 480
gctttcgata agtctctagc catttaaaat ttttgatgac ctgctgcgac gctttttttc 540
tggcaagata gtcttgtaaa tgcgggccaa gatctgcaca ctggtatttc ggtttttggg 600
gccgcgggcg gcgacggggc ccgtgcgtcc cagcgcacat gttcggcgag gcggggcctg 660
cgagcgcggc caccgagaat cggacggggg tagtctcaag ctggccggcc tgctctggtg 720
cctggcctcg cgccgccgtg tatcgccccg ccctgggcgg caaggctggc ccggtcggca 780
ccagttgcgt gagcggaaag atggccgctt cccggccctg ctgcagggag ctcaaaatgg 840
aggacgcggc gctcgggaga gcgggcgggt gagtcaccca cacaaaggaa aagggccttt 900
ccgtcctcag ccgtcgcttc atgtgactcc acggagtacc gggcgccgtc caggcacctc 960
gattagttct cgagcttttg gagtacgtcg tctttaggtt ggggggaggg gttttatgcg 1020
atggagtttc cccacactga gtgggtggag actgaagtta ggccagcttg gcacttgatg 1080
taattctcct tggaatttgc cctttttgag tttggatctt ggttcattct caagcctcag 1140
acagtggttc aaagtttttt tcttccattt caggtgtcgt ga 1182

<210> SEQ ID NO 5
<211> LENGTH: 705
<212> TYPE: DNA
<213> ORGANISM: Homo sapiens

<400> SEQUENCE: 5
ttaagctcgg gccctgggcg ggattcgtct tgggcgggat ccttgtccac gtgatcgggg 60
gagggacttt cccgctggag tgactcatct agcccacgtg atcttcatgc cacgtgatcg 120
atatggggac tttcctgact cccacgtgat cgcacccccca cgtgatcccg taagggactt 180
tccctacttt gcctagagaa ggtggcgcgg ggtaaactgg gaaagtgatg tcgtgtactg 240
gctccgcctt tttcccgtgc tcaggggaga accgtatata agtgcagtag tcgccgtgaa 300
cgttcttttt cgcaacgtta actagcacag aacacaggta agtgccgtgt gtggttcccg 360
cgggcggcga cggggcccgt gcccacgtga tcaggagttg ggcgggatgt tatgagtgac 420
tcacgccatc cacgtgatct cagacgggac tttccatatt aagtgactca ggataaggga 480
ctttccctac ggccacgtga tctctttttg ggcgggatga gattgggact ttcctgtcct 540
gggactttcc tacagttcaa actcgaccac gtgatcttat gactgacggg cgggtgagtc 600
acccacggtg gcatggggga ctttccttta ggcgttcatg tgactccacg gacaagcctc 660
agacagtggt tcaaagtttt tttcttccat ttcaggtgtc gtgaa 705

<210> SEQ ID NO 6
<211> LENGTH: 216
<212> TYPE: PRT
<213> ORGANISM: Escherichia coli

<400> SEQUENCE: 6

Met Ser Asn Gln Glu Pro Ala Thr Ile Leu Leu Ile Asp Asp His Pro
1 5 10 15

Met Leu Arg Thr Gly Val Lys Gln Leu Ile Ser Met Ala Pro Asp Ile
20 25 30

```
Thr Val Val Gly Glu Ala Ser Asn Gly Glu Gln Gly Ile Glu Leu Ala
        35                  40                  45

Glu Ser Leu Asp Pro Asp Leu Ile Leu Leu Asp Leu Asn Met Pro Gly
    50                  55                  60

Met Asn Gly Leu Glu Thr Leu Asp Lys Leu Arg Glu Lys Ser Leu Ser
65                  70                  75                  80

Gly Arg Ile Val Val Phe Ser Val Ser Asn His Glu Glu Asp Val Val
                85                  90                  95

Thr Ala Leu Lys Arg Gly Ala Asp Gly Tyr Leu Leu Lys Asp Met Glu
            100                 105                 110

Pro Glu Asp Leu Leu Lys Ala Leu His Gln Ala Ala Ala Gly Glu Met
        115                 120                 125

Val Leu Ser Glu Ala Leu Thr Pro Val Leu Ala Ala Ser Leu Arg Ala
    130                 135                 140

Asn Arg Ala Thr Thr Glu Arg Asp Val Asn Gln Leu Thr Pro Arg Glu
145                 150                 155                 160

Arg Asp Ile Leu Lys Leu Ile Ala Gln Gly Leu Pro Asn Lys Met Ile
                165                 170                 175

Ala Arg Arg Leu Asp Ile Thr Glu Ser Thr Val Lys Val His Val Lys
            180                 185                 190

His Met Leu Lys Lys Met Lys Leu Lys Ser Arg Val Glu Ala Ala Val
        195                 200                 205

Trp Val His Gln Glu Arg Ile Phe
    210                 215


<210> SEQ ID NO 7
<211> LENGTH: 42
<212> TYPE: PRT
<213> ORGANISM: Escherichia coli

<400> SEQUENCE: 7

Gly Pro Ala Asp Ala Leu Asp Asp Phe Asp Leu Asp Met Leu Pro Ala
1               5                   10                  15

Asp Ala Leu Asp Asp Phe Asp Leu Asp Met Leu Pro Ala Asp Ala Leu
            20                  25                  30

Asp Asp Phe Asp Leu Asp Met Leu Pro Gly
        35                  40


<210> SEQ ID NO 8
<211> LENGTH: 272
<212> TYPE: PRT
<213> ORGANISM: Escherichia coli

<400> SEQUENCE: 8

Met Arg Ile Gln Asn Arg Pro Leu Val Asp Leu Glu His Ala Ala Leu
1               5                   10                  15

Gln Val Gly Lys Gly Ile Ile Pro Pro Pro Leu Arg Glu Tyr Gly Ala
            20                  25                  30

Ser Glu Val Arg Ser Val Thr Arg Ala Phe Asn His Met Ala Ala Gly
        35                  40                  45

Val Lys Gln Leu Ala Asp Asp Arg Thr Leu Leu Met Ala Gly Val Ser
    50                  55                  60

His Asp Leu Arg Thr Pro Leu Thr Arg Ile Arg Leu Ala Thr Glu Met
65                  70                  75                  80

Met Ser Glu Gln Asp Gly Tyr Leu Ala Glu Ser Ile Asn Lys Asp Ile
                85                  90                  95
```

```
Glu Glu Cys Asn Ala Ile Ile Glu Gln Phe Ile Asp Tyr Leu Arg Thr
            100                 105                 110

Gly Gln Glu Met Pro Met Glu Met Ala Asp Leu Asn Ala Val Leu Gly
        115                 120                 125

Glu Val Ile Ala Ala Glu Ser Gly Tyr Glu Arg Glu Ile Glu Thr Ala
    130                 135                 140

Leu Tyr Pro Gly Ser Ile Glu Val Lys Met His Pro Leu Ser Ile Lys
145                 150                 155                 160

Arg Ala Val Ala Asn Met Val Val Asn Ala Ala Arg Tyr Gly Asn Gly
                165                 170                 175

Trp Ile Lys Val Ser Ser Gly Thr Glu Pro Asn Arg Ala Trp Phe Gln
            180                 185                 190

Val Glu Asp Asp Gly Pro Gly Ile Ala Pro Glu Gln Arg Lys His Leu
        195                 200                 205

Phe Gln Pro Phe Val Arg Gly Asp Ser Ala Arg Thr Ile Ser Gly Thr
    210                 215                 220

Gly Leu Gly Leu Ala Ile Val Gln Arg Ile Val Asp Asn His Asn Gly
225                 230                 235                 240

Met Leu Glu Leu Gly Thr Ser Glu Arg Gly Gly Leu Ser Ile Arg Ala
                245                 250                 255

Trp Leu Pro Val Pro Val Thr Arg Ala Gln Gly Thr Thr Lys Glu Gly
            260                 265                 270


<210> SEQ ID NO 9
<211> LENGTH: 228
<212> TYPE: PRT
<213> ORGANISM: Escherichia coli

<400> SEQUENCE: 9

Met Ala Ala Gly Val Lys Gln Leu Ala Asp Asp Arg Thr Leu Leu Met
1               5                   10                  15

Ala Gly Val Ser His Asp Leu Arg Thr Pro Leu Thr Arg Ile Arg Leu
            20                  25                  30

Ala Thr Glu Met Met Ser Glu Gln Asp Gly Tyr Leu Ala Glu Ser Ile
        35                  40                  45

Asn Lys Asp Ile Glu Glu Cys Asn Ala Ile Ile Glu Gln Phe Ile Asp
    50                  55                  60

Tyr Leu Arg Thr Gly Gln Glu Met Pro Met Glu Met Ala Asp Leu Asn
65                  70                  75                  80

Ala Val Leu Gly Glu Val Ile Ala Ala Glu Ser Gly Tyr Glu Arg Glu
                85                  90                  95

Ile Glu Thr Ala Leu Tyr Pro Gly Ser Ile Glu Val Lys Met His Pro
            100                 105                 110

Leu Ser Ile Lys Arg Ala Val Ala Asn Met Val Val Asn Ala Ala Arg
        115                 120                 125

Tyr Gly Asn Gly Trp Ile Lys Val Ser Ser Gly Thr Glu Pro Asn Arg
    130                 135                 140

Ala Trp Phe Gln Val Glu Asp Asp Gly Pro Gly Ile Ala Pro Glu Gln
145                 150                 155                 160

Arg Lys His Leu Phe Gln Pro Phe Val Arg Gly Asp Ser Ala Arg Thr
                165                 170                 175

Ile Ser Gly Thr Gly Leu Gly Leu Ala Ile Val Gln Arg Ile Val Asp
            180                 185                 190

Asn His Asn Gly Met Leu Glu Leu Gly Thr Ser Glu Arg Gly Gly Leu
        195                 200                 205
```

```
Ser Ile Arg Ala Trp Leu Pro Val Pro Val Thr Arg Ala Gln Gly Thr
    210                 215                 220

Thr Lys Glu Gly
225


<210> SEQ ID NO 10
<211> LENGTH: 424
<212> TYPE: PRT
<213> ORGANISM: Escherichia coli

<400> SEQUENCE: 10

Met Ala Arg Leu Leu Gln Pro Trp Arg Gln Leu Leu Ala Met Ala Ser
1               5                   10                  15

Ala Val Ser His Arg Asp Phe Thr Gln Arg Ala Asn Ile Ser Gly Arg
            20                  25                  30

Asn Glu Met Ala Met Leu Gly Thr Ala Leu Asn Asn Met Ser Ala Glu
        35                  40                  45

Leu Ala Glu Ser Tyr Ala Val Leu Glu Gln Arg Val Gln Glu Lys Thr
    50                  55                  60

Ala Gly Leu Glu His Lys Asn Gln Ile Leu Ser Phe Leu Trp Gln Ala
65                  70                  75                  80

Asn Arg Arg Leu His Ser Arg Ala Pro Leu Cys Glu Arg Leu Ser Pro
                85                  90                  95

Val Leu Asn Gly Leu Gln Asn Leu Thr Leu Leu Arg Asp Ile Glu Leu
            100                 105                 110

Arg Val Tyr Asp Thr Asp Asp Glu Glu Asn His Gln Glu Phe Thr Cys
        115                 120                 125

Gln Pro Asp Met Thr Cys Asp Asp Lys Gly Cys Gln Leu Cys Pro Arg
    130                 135                 140

Gly Val Leu Pro Val Gly Asp Arg Gly Thr Thr Leu Lys Trp Arg Leu
145                 150                 155                 160

Ala Asp Ser His Thr Gln Tyr Gly Ile Leu Leu Ala Thr Leu Pro Gln
                165                 170                 175

Gly Arg His Leu Ser His Asp Gln Gln Gln Leu Val Asp Thr Leu Val
            180                 185                 190

Glu Gln Leu Thr Ala Thr Leu Ala Leu Asp Arg His Gln Glu Arg Gln
        195                 200                 205

Gln Gln Leu Ile Val Met Glu Glu Arg Ala Thr Ile Ala Arg Glu Leu
    210                 215                 220

His Asp Ser Ile Ala Gln Ser Leu Ser Cys Met Lys Met Gln Val Ser
225                 230                 235                 240

Cys Leu Gln Met Gln Gly Asp Ala Leu Pro Glu Ser Ser Arg Glu Leu
                245                 250                 255

Leu Ser Gln Ile Arg Asn Glu Leu Asn Ala Ser Trp Ala Gln Leu Arg
            260                 265                 270

Glu Leu Leu Thr Thr Phe Arg Leu Gln Leu Thr Glu Pro Gly Leu Arg
        275                 280                 285

Pro Ala Leu Glu Ala Ser Cys Glu Glu Tyr Ser Ala Lys Phe Gly Phe
    290                 295                 300

Pro Val Lys Leu Asp Tyr Gln Leu Pro Pro Arg Leu Val Pro Ser His
305                 310                 315                 320

Gln Ala Ile His Leu Leu Gln Ile Ala Arg Glu Ala Leu Ser Asn Ala
                325                 330                 335

Leu Lys His Ser Gln Ala Ser Glu Val Val Val Thr Val Ala Gln Asn
```

340 345 350

Asp Asn Gln Val Lys Leu Thr Val Gln Asp Asn Gly Cys Gly Val Pro
355 360 365

Glu Asn Ala Ile Arg Ser Asn His Tyr Gly Met Ile Ile Met Arg Asp
370 375 380

Arg Ala Gln Ser Leu Arg Gly Asp Cys Arg Val Arg Arg Arg Glu Ser
385 390 395 400

Gly Gly Thr Glu Val Val Val Thr Phe Ile Pro Glu Lys Thr Phe Thr
405 410 415

Asp Val Gln Gly Asp Thr His Glu
420

<210> SEQ ID NO 11
<211> LENGTH: 221
<212> TYPE: PRT
<213> ORGANISM: Escherichia coli

<400> SEQUENCE: 11

Met Gln Glu Arg Gln Gln Gln Leu Ile Val Met Glu Glu Arg Ala Thr
1 5 10 15

Ile Ala Arg Glu Leu His Asp Ser Ile Ala Gln Ser Leu Ser Cys Met
20 25 30

Lys Met Gln Val Ser Cys Leu Gln Met Gln Gly Asp Ala Leu Pro Glu
35 40 45

Ser Ser Arg Glu Leu Leu Ser Gln Ile Arg Asn Glu Leu Asn Ala Ser
50 55 60

Trp Ala Gln Leu Arg Glu Leu Leu Thr Thr Phe Arg Leu Gln Leu Thr
65 70 75 80

Glu Pro Gly Leu Arg Pro Ala Leu Glu Ala Ser Cys Glu Glu Tyr Ser
85 90 95

Ala Lys Phe Gly Phe Pro Val Lys Leu Asp Tyr Gln Leu Pro Pro Arg
100 105 110

Leu Val Pro Ser His Gln Ala Ile His Leu Leu Gln Ile Ala Arg Glu
115 120 125

Ala Leu Ser Asn Ala Leu Lys His Ser Gln Ala Ser Glu Val Val Val
130 135 140

Thr Val Ala Gln Asn Asp Asn Gln Val Lys Leu Thr Val Gln Asp Asn
145 150 155 160

Gly Cys Gly Val Pro Glu Asn Ala Ile Arg Ser Asn His Tyr Gly Met
165 170 175

Ile Ile Met Arg Asp Arg Ala Gln Ser Leu Arg Gly Asp Cys Arg Val
180 185 190

Arg Arg Arg Glu Ser Gly Gly Thr Glu Val Val Val Thr Phe Ile Pro
195 200 205

Glu Lys Thr Phe Thr Asp Val Gln Gly Asp Thr His Glu
210 215 220

<210> SEQ ID NO 12
<211> LENGTH: 221
<212> TYPE: PRT
<213> ORGANISM: Escherichia coli

<400> SEQUENCE: 12

Met Gln Glu Arg Gln Gln Gln Leu Ile Val Met Glu Glu Arg Ala Thr
1 5 10 15

Ile Ala Arg Glu Leu Gln Asp Ser Ile Ala Gln Ser Leu Ser Cys Met

```
            20                  25                  30

Lys Met Gln Val Ser Cys Leu Gln Met Gln Gly Asp Ala Leu Pro Glu
        35                  40                  45

Ser Ser Arg Glu Leu Leu Ser Gln Ile Arg Asn Glu Leu Asn Ala Ser
    50                  55                  60

Trp Ala Gln Leu Arg Glu Leu Leu Thr Thr Phe Arg Leu Gln Leu Thr
65                  70                  75                  80

Glu Pro Gly Leu Arg Pro Ala Leu Glu Ala Ser Cys Glu Glu Tyr Ser
                85                  90                  95

Ala Lys Phe Gly Phe Pro Val Lys Leu Asp Tyr Gln Leu Pro Pro Arg
            100                 105                 110

Leu Val Pro Ser His Gln Ala Ile His Leu Leu Gln Ile Ala Arg Glu
        115                 120                 125

Ala Leu Ser Asn Ala Leu Lys His Ser Gln Ala Ser Glu Val Val Val
    130                 135                 140

Thr Val Ala Gln Asn Asp Asn Gln Val Lys Leu Thr Val Gln Asp Asn
145                 150                 155                 160

Gly Cys Gly Val Pro Glu Asn Ala Ile Arg Ser Asn His Tyr Gly Met
                165                 170                 175

Ile Ile Met Arg Asp Arg Ala Gln Ser Leu Arg Gly Asp Cys Arg Val
            180                 185                 190

Arg Arg Arg Glu Ser Gly Gly Thr Glu Val Val Val Thr Phe Ile Pro
        195                 200                 205

Glu Lys Thr Phe Thr Asp Val Gln Gly Asp Thr His Glu
    210                 215                 220


<210> SEQ ID NO 13
<211> LENGTH: 221
<212> TYPE: PRT
<213> ORGANISM: Escherichia coli

<400> SEQUENCE: 13

Met Gln Glu Arg Gln Gln Gln Leu Ile Val Met Glu Glu Arg Ala Thr
1               5                   10                  15

Ile Ala Arg Glu Leu His Asp Ser Ile Ala Gln Ser Leu Ser Cys Met
            20                  25                  30

Lys Met Gln Val Ser Cys Leu Gln Met Gln Gly Asp Ala Leu Pro Glu
        35                  40                  45

Ser Ser Arg Glu Leu Leu Ser Gln Ile Arg Asn Glu Leu Asn Ala Ser
    50                  55                  60

Trp Ala Gln Leu Arg Glu Leu Leu Thr Thr Phe Arg Leu Gln Leu Thr
65                  70                  75                  80

Glu Pro Gly Leu Arg Pro Ala Leu Glu Ala Ser Cys Glu Glu Tyr Ser
                85                  90                  95

Ala Lys Phe Gly Phe Pro Val Lys Leu Asp Tyr Gln Leu Pro Pro Arg
            100                 105                 110

Leu Val Pro Ser His Gln Ala Ile His Leu Leu Gln Ile Ala Arg Glu
        115                 120                 125

Ala Leu Ser Ala Ala Leu Lys His Ser Gln Ala Ser Glu Val Val Val
    130                 135                 140

Thr Val Ala Gln Asn Asp Asn Gln Val Lys Leu Thr Val Gln Asp Asn
145                 150                 155                 160

Gly Cys Gly Val Pro Glu Asn Ala Ile Arg Ser Asn His Tyr Gly Met
                165                 170                 175
```

```
Ile Ile Met Arg Asp Arg Ala Gln Ser Leu Arg Gly Asp Cys Arg Val
            180                 185                 190

Arg Arg Arg Glu Ser Gly Gly Thr Glu Val Val Val Thr Phe Ile Pro
        195                 200                 205

Glu Lys Thr Phe Thr Asp Val Gln Gly Asp Thr His Glu
    210                 215                 220


<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14

gctgctgctc tcgagtcatt atcattcgtg agtgtc                               36


<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15

gctgctaccg gtcgccacca tggcccgctt gctccagccg tgg                       43


<210> SEQ ID NO 16
<211> LENGTH: 72
<212> TYPE: DNA
<213> ORGANISM: Artificial Sequence
<220> FEATURE:
<223> OTHER INFORMATION: Primer

<400> SEQUENCE: 16

cgcgcctgat tacaaaactt taaaaagtgc tgtagcgccg gctgattaca aaactttaaa     60

aagtgctgtc ca                                                         72


<210> SEQ ID NO 17
<211> LENGTH: 70
<212> TYPE: DNA
<213> ORGANISM: Artificial Sequence
<220> FEATURE:
<223> OTHER INFORMATION: Primer

<400> SEQUENCE: 17

tatggacagc actttttaaa gttttgtaat cagccggcgc tacagcactt tttaaagttt     60

tgtaatcagg                                                            70


<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18

taagcggaat tcatcttggc tgaggaatct t                                    31


<210> SEQ ID NO 19
<211> LENGTH: 31
<212> TYPE: DNA
<213> ORGANISM: Artificial Sequence
<220> FEATURE:
```

<223> OTHER INFORMATION: Primer

<400> SEQUENCE: 19
gcgaattcta gactacttgt acagctcgtc c 31

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
aatgtgaagc tagcgccacc atggctgaag gatccgtcg 39

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
aatgtaatct agatcactct tccatcacgc cgatc 35

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gctagcgcta ccggactcag at 22

<210> SEQ ID NO 23
<211> LENGTH: 43
<212> TYPE: DNA
<213> ORGANISM: Artificial Sequence
<220> FEATURE:
<223> OTHER INFORMATION: Primer

<400> SEQUENCE: 23
tgggtggggt gcgtccgcgc gcacagaagt cccggaaaca ccg 43

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
tgggtggggt gcgtccgcgc gcacacagaa gctcctggaa ggcaa 45

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ggcacagtcg aggctgattt tc 22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tggcagcggg cgtcaagcag 20

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
atggtggtgg cagcggcgag gtatggcaac g 31

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
ctcgccgctg ccaccaccat gttggcgacg 30

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
gaaattaata cgactcacta taggggac 28

<210> SEQ ID NO 30
<211> LENGTH: 57
<212> TYPE: DNA
<213> ORGANISM: Artificial Sequence
<220> FEATURE:
<223> OTHER INFORMATION: Primer

<400> SEQUENCE: 30
gaaattaata cgactcacta taggggaccg gtcgccacca tggcagcggg cgtcaag 57

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cacagtcgag gctgattttc 20

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
gtttgagagc tgccgagagt gcttctctcg cg 32

<210> SEQ ID NO 33
<211> LENGTH: 32
<212> TYPE: DNA
<213> ORGANISM: Artificial Sequence
<220> FEATURE:
<223> OTHER INFORMATION: Primer

<400> SEQUENCE: 33
agcactctcg gcagctctca aacatagcca gg 32

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34
cttccagtgc agcttcaatc agatttccca gtgtg 35

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
tctgattgaa gctgcactgg aagctctggg ac 32

<210> SEQ ID NO 36
<211> LENGTH: 60
<212> TYPE: DNA
<213> ORGANISM: Artificial Sequence
<220> FEATURE:
<223> OTHER INFORMATION: Primer

<400> SEQUENCE: 36
gaaattaata cgactcacta taggggaccg gtcgccacca tgcaagagcg gcagcagcag 60

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
gacggccagt cttaagctcg ggcccgctcc ggtgcccgtc ag 42

<210> SEQ ID NO 38
<211> LENGTH: 47
<212> TYPE: DNA
<213> ORGANISM: Artificial Sequence
<220> FEATURE:
<223> OTHER INFORMATION: Primer

<400> SEQUENCE: 38
gaagtcgtcg catggtggcg accggttcac gacacctgaa atggaag 47

<210> SEQ ID NO 39
<211> LENGTH: 43

<212> TYPE: DNA
<213> ORGANISM: Artificial Sequence
<220> FEATURE:
<223> OTHER INFORMATION: Primer

<400> SEQUENCE: 39
gacggccagt cttaagctcg ggccctgggc gggattcgtc ttg 43

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
caagagcggc agcagcag 18

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
ttcgtgagtg tcaccctgc 19

<210> SEQ ID NO 42
<211> LENGTH: 57
<212> TYPE: DNA
<213> ORGANISM: Artificial Sequence
<220> FEATURE:
<223> OTHER INFORMATION: Primer

<400> SEQUENCE: 42
gaaattaata cgactcacta taggggaccg gtcgccacca tgggcgtgca ggtggag 57

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
cgccaccgcc tgaaccgcct ccaccttcca gttttagaag ctccacatc 49

<210> SEQ ID NO 44
<211> LENGTH: 57
<212> TYPE: DNA
<213> ORGANISM: Artificial Sequence
<220> FEATURE:
<223> OTHER INFORMATION: Primer

<400> SEQUENCE: 44
gaaattaata cgactcacta taggggaccg gtcgccacca tggtagccat cctctgg 57

<210> SEQ ID NO 45
<211> LENGTH: 46
<212> TYPE: DNA
<213> ORGANISM: Artificial Sequence
<220> FEATURE:
<223> OTHER INFORMATION: Primer

<400> SEQUENCE: 45
cgccaccgcc tgaaccgcct ccacctgata tccgtctgaa cacgtg 46

<210> SEQ ID NO 46
<211> LENGTH: 43
<212> TYPE: DNA
<213> ORGANISM: Artificial Sequence
<220> FEATURE:
<223> OTHER INFORMATION: Primer

<400> SEQUENCE: 46
aggcggttca ggcggtggcg ggtcgcaaga gcggcagcag cag 43

<210> SEQ ID NO 47
<211> LENGTH: 52
<212> TYPE: DNA
<213> ORGANISM: Artificial Sequence
<220> FEATURE:
<223> OTHER INFORMATION: Primer

<400> SEQUENCE: 47
cgcgcctacc cctatagggg tatagcgccg gctaccccta taggggtatc ca 52

<210> SEQ ID NO 48
<211> LENGTH: 50
<212> TYPE: DNA
<213> ORGANISM: Artificial Sequence
<220> FEATURE:
<223> OTHER INFORMATION: Primer

<400> SEQUENCE: 48
tatggatacc cctatagggg tagccggcgc tatacccta taggggtagg 50

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
ttcttccatt tcaggtgtcg tgaaccggtc gccaccatgg gctc 44

<210> SEQ ID NO 50
<211> LENGTH: 30
<212> TYPE: DNA
<213> ORGANISM: Artificial Sequence
<220> FEATURE:
<223> OTHER INFORMATION: Priomer

<400> SEQUENCE: 50
catcgtcatg gaagagaggg cgactattgc 30

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
gcaatagtcg ccctctcttc catgacgatg 30

<210> SEQ ID NO 52
<211> LENGTH: 44
<212> TYPE: DNA
<213> ORGANISM: Artificial Sequence
<220> FEATURE:
<223> OTHER INFORMATION: Primer

<400> SEQUENCE: 52
ttcttccatt tcaggtgtcg tgaaccggtc gccaccatgg gcgt 44

<210> SEQ ID NO 53
<211> LENGTH: 44
<212> TYPE: DNA
<213> ORGANISM: Artificial Sequence
<220> FEATURE:
<223> OTHER INFORMATION: Primer

<400> SEQUENCE: 53
ttcttccatt tcaggtgtcg tgaaccggtc gccaccatgg tagc 44

<210> SEQ ID NO 54
<211> LENGTH: 57
<212> TYPE: DNA
<213> ORGANISM: Artificial Sequence
<220> FEATURE:
<223> OTHER INFORMATION: Primer

<400> SEQUENCE: 54
ttcttccatt tcaggtgtcg tgaaccggtc gccaccatgc aagagcggca gcagcag 57

<210> SEQ ID NO 55
<211> LENGTH: 39
<212> TYPE: DNA
<213> ORGANISM: Artificial Sequence
<220> FEATURE:
<223> OTHER INFORMATION: Primer

<400> SEQUENCE: 55
cctgattgga catggtggcg accggttcac gacacctga 39

<210> SEQ ID NO 56
<211> LENGTH: 42
<212> TYPE: DNA
<213> ORGANISM: Artificial Sequence
<220> FEATURE:
<223> OTHER INFORMATION: Primer

<400> SEQUENCE: 56
ttcttccatt tcaggtgtcg tgaaccggtc gccaccatgc tt 42

<210> SEQ ID NO 57
<211> LENGTH: 52
<212> TYPE: DNA
<213> ORGANISM: Artificial Sequence
<220> FEATURE:
<223> OTHER INFORMATION: Primer

<400> SEQUENCE: 57
tccatttcag gtgtcgtgaa ccggtcgcca ccatggggga gaaacccggg ac 52

<210> SEQ ID NO 58
<211> LENGTH: 45
<212> TYPE: DNA
<213> ORGANISM: Artificial Sequence
<220> FEATURE:
<223> OTHER INFORMATION: Primer

<400> SEQUENCE: 58
ctcttgcgag ccaccgccac cgcagagttg atcatcatag tcgtc 45

<210> SEQ ID NO 59
<211> LENGTH: 33
<212> TYPE: DNA
<213> ORGANISM: Artificial Sequence
<220> FEATURE:
<223> OTHER INFORMATION: Primer

<400> SEQUENCE: 59
ggtggcggtg gctcgcaaga gcggcagcag cag 33

<210> SEQ ID NO 60
<211> LENGTH: 50
<212> TYPE: DNA
<213> ORGANISM: Artificial Sequence
<220> FEATURE:
<223> OTHER INFORMATION: Primer

<400> SEQUENCE: 60
tccatttcag gtgtcgtgaa ccggtcgcca ccatggggca acccgggaac 50

<210> SEQ ID NO 61
<211> LENGTH: 40
<212> TYPE: DNA
<213> ORGANISM: Artificial Sequence
<220> FEATURE:
<223> OTHER INFORMATION: Primer

<400> SEQUENCE: 61
ctcttgcgag ccaccgccac ccgatgaagt gtccttggcc 40

<210> SEQ ID NO 62
<211> LENGTH: 38
<212> TYPE: DNA
<213> ORGANISM: Artificial Sequence
<220> FEATURE:
<223> OTHER INFORMATION: Primer

<400> SEQUENCE: 62
attacgccaa gctacggggg cacctcgaca tactcgag 38

<210> SEQ ID NO 63
<211> LENGTH: 41
<212> TYPE: DNA
<213> ORGANISM: Artificial Sequence
<220> FEATURE:
<223> OTHER INFORMATION: Primer

<400> SEQUENCE: 63
ccttgctcac catggtggcg aggtaccgag ctcgaaatct c 41

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
accgggagaa gcggggtctc g 21

<210> SEQ ID NO 65
<211> LENGTH: 40
<212> TYPE: DNA
<213> ORGANISM: Artificial Sequence
<220> FEATURE:
<223> OTHER INFORMATION: Primer

<400> SEQUENCE: 65
cagtcgaggc tgattttctc gctcaagcgt aatctggaac 40

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
gttccagatt acgcttgagc gagaaaatca gcctcgactg 40

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
ccgggagctt tttgcaaaag c 21

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
ggacggggca tggactccgc ag 22

<210> SEQ ID NO 69
<211> LENGTH: 56
<212> TYPE: DNA
<213> ORGANISM: Artificial Sequence
<220> FEATURE:
<223> OTHER INFORMATION: primer

<400> SEQUENCE: 69
gcacagtcga ggctgatttt ctcgagtcat tactacccac cgtactcgtc aattcc 56

<210> SEQ ID NO 70
<211> LENGTH: 996
<212> TYPE: DNA
<213> ORGANISM: Artificial Sequence
<220> FEATURE:
<223> OTHER INFORMATION: synthetic DNA used for plasmid constructs

<400> SEQUENCE: 70
agatctcgag ctcaagcttc gaattcgcca ccatggggga gaaacccggg accagggtct 60
tcaagaagtc gagccctaac tgcaagctca ccgtgtactt gggcaagcgg gacttcgtag 120
atcacctgga caaagtggac cctgtagatg gcgtggtgct tgtggaccct gactacctga 180
aggaccgcaa agtgtttgtg accctcacct gcgccttccg ctatggccgt gaagacctgg 240
atgtgctggg cttgtccttc cgcaaagacc tgttcatcgc cacctaccag gccttccccc 300
cggtgcccaa cccaccccgg ccccccaccc gcctgcagga ccggctgctg aggaagctgg 360
gccagcatgc ccaccccttc ttcttcacca taccccagaa tcttccatgc tccgtcacac 420
tgcagccagg cccagaggat acaggaaagg cctgcggcgt agactttgag attcgagcct 480
tctgtgctaa atcactagaa gagaaaagcc acaaaaggaa ctctgtgcgg ctggtgatcc 540
gaaaggtgca gttcgccccg gagaaacccg gcccccagcc ttcagccgaa accacacgcc 600
acttcctcat gtctgaccgg tccctgcacc tcgaggcttc cctggacaag gagctgtact 660
accatgggga gcccctcaat gtaaatgtcc acgtcaccaa caactccacc aagaccgtca 720
agaagatcaa agtctctgtg agacagtacg ccgacatctg cctcttcagc accgcccagt 780
acaagtgtcc tgtggctcaa ctcgaacaag atgaccaggt atctcccagc tccacattct 840
gtaaggtgta caccataacc ccactgctca gcgacaaccg ggagaagcgg ggtctcgccc 900
tggatgggaa actcaagcac gaggacacca acctggcttc cagcaccatc gtgaaggagg 960
gtgccaacaa ggaggtgctg ggaatcctgg tgtcct 996

<210> SEQ ID NO 71
<211> LENGTH: 1066
<212> TYPE: DNA
<213> ORGANISM: Artificial Sequence
<220> FEATURE:
<223> OTHER INFORMATION: synthetic DNA used for plasmid constructs

<400> SEQUENCE: 71
gctgggaatc ctggtgtcct acagggtcaa ggtgaagctg gtggtgtctc gaggcgggga 60
tgtctctgtg gagctgcctt ttgttcttat gcaccccaag ccccacgacc acatccccct 120
ccccagaccc cagtcagccg ctccggagac agatgtccct gtggacacca acctcattga 180
atttgatacc aactatgcca cagatgatga cattgtgttt gaggactttg cccggcttcg 240
gctgaagggg atgaaggatg acgactatga tgatcaactc tgcggatcca gcttgtttaa 300
gggaccacgt gattacaacc cgatatcgag caccatttgt catttgacga atgaatctga 360
tgggcacaca acatcgttgt atggtattgg atttggtccc ttcatcatta caaacaagca 420
cttgtttaga agaaataatg gaacactgtt ggtccaatca ctacatggtg tattcaaggt 480
caagaacacc acgactttgc aacaacacct cattgatggg agggacatga taattattcg 540
catgcctaag gatttcccac catttcctca aaagctgaaa tttagagagc cacaaaggga 600
agagcgcata tgtcttgtga caaccaactt ccaaactaag agcatgtcta gcatggtgtc 660
agacactagt tgcacattcc cttcatctga tggcatattc tggaagcatt ggattcaaac 720
caaggatggg cagtgtggca gtccattagt atcaactaga gatgggttca ttgttggtat 780
acactcagca tcgaatttca ccaacacaaa caattatttc acaagcgtgc cgaaaaactt 840
catggaattg ttgacaaatc aggaggcgca gcagtgggtt agtggttggc gattaaatgc 900
tgactcagta ttgtgggggg gccataaagt tttcatgagc aaacctgaag agccttttca 960
gccagttaag gaagcgactc aactcatgaa tgaattggtg tactcgcaat acccatacga 1020
tgttccagat tacgcttgag cggccgcgac tctagatcat aatcag 1066

<210> SEQ ID NO 72
<211> LENGTH: 1201
<212> TYPE: DNA
<213> ORGANISM: Artificial Sequence
<220> FEATURE:
<223> OTHER INFORMATION: synthetic DNA used for plasmid constructs

<400> SEQUENCE: 72
gcgctaccgg actcagatct cgaggccacc atggactccc cgatccagat cttccgcggg 60
gagccgggcc ctacctgcgc cccgagcgcc tgcctgcccc ccaacagcag cgcctggttt 120
cccggctggg ccgagcccga cagcaacggc agcgccggct cggaggacgc gcagctggag 180
cccgcgcaca tctccccggc catcccggtc atcatcacgg cggtctactc cgtagtgttc 240
gtcgtgggct tggtgggcaa ctcgctggtc atgttcgtga tcatccgata cacaaagatg 300
aagacagcaa ccaacattta catatttaac ctggctttgg cagatgcttt agttactaca 360
accatgccct ttcagagtac ggtctacttg atgaattcct ggccttttgg ggatgtgctg 420
tgcaagatag taatttccat tgattactac aacatgttca ccagcatctt caccttgacc 480
atgatgagcg tggaccgcta cattgccgtg tgccaccccg tgaaggcttt ggacttccgc 540
acacccttga aggcaaagat catcaatatc tgcatctggc tgctgtcgtc atctgttggc 600
atctctgcaa tagtccttgg aggcaccaaa gtcagggaag acgtcgatgt cattgagtgc 660
tccttgcagt tcccagatga tgactactcc tggtgggacc tcttcatgaa gatctgcgtc 720
ttcatctttg ccttcgtgat ccctgtcctc atcatcatcg tctgctacac cctgatgatc 780
ctgcgtctca agagcgtccg gctcctttct ggctcccgag agaaagatcg caacctgcgt 840
aggatcacca gactggtcct ggtggtggtg gcagtcttcg tcgtctgctg gactcccatt 900
cacatattca tcctggtgga ggctctgggg agcacctccc acagcacagc tgctctctcc 960
agctattact tctgcatcgc cttaggctat accaacagta gcctgaatcc cattctctac 1020
gcctttcttg atgaaaactt caagcggtgt ttccgggact tctgttttcc actgaagatg 1080
aggatggagc ggcagagcac tagcagagtc cgaaatacag ttcaggaccc tgcttacctg 1140
agggacatcg atgggatgaa taaaccagta tgacaattgt tgttgttaac ttgtttattg 1200
c 1201

<210> SEQ ID NO 73
<211> LENGTH: 1167
<212> TYPE: DNA
<213> ORGANISM: Artificial Sequence
<220> FEATURE:
<223> OTHER INFORMATION: synthetic DNA used for plasmid constructs

<400> SEQUENCE: 73
agcggtgttt ccgggacttc tgtgcgcgcg gacgcacccc acccagcctg ggtccccaag 60
atgagtcctg caccaccgcc agctcctccc tggccaagga cacttcatcg ggatccgaga 120
atctgtactt tcagctgaga ttagataaaa gtaaagtgat taacagcgca ttagagctgc 180
ttaatgaggt cggaatcgaa ggtttaacaa cccgtaaact cgcccagaag ctaggtgtag 240
agcagcctac attgtattgg catgtaaaaa ataagcgggc tttgctcgac gccttagcca 300
ttgagatgtt agataggcac catactcact tttgcccttt agaaggggaa agctggcaag 360 atttttacg taataacgct aaaagtttta gatgtgcttt actaagtcat cgcgatggag 420
caaaagtaca tttaggtaca cggcctacag aaaaacagta tgaaactctc gaaaatcaat 480
tagccttttt atgccaacaa ggtttttcac tagagaatgc attatatgca ctcagcgctg 540
tggggcattt tactttaggt tgcgtattgg aagatcaaga gcatcaagtc gctaaagaag 600
aaagggaaac acctactact gatagtatgc cgccattatt acgacaagct atcgaattat 660
ttgatcacca aggtgcagag ccagccttct tattcggcct tgaattgatc atatgcggat 720
tagaaaaaca acttaaatgt gaaagtgggt ccgcgtacag ccgggcgcgt acgaaaaaca 780
attacgggtc taccatcgag ggcctgctcg atctcccgga cgacgacgcc cccgaagagg 840
cggggctggc ggctccgcgc ctgtcctttc tccccgcggg acacacgcgc agactgtcga 900 cggcccccc gaccgatgtc agcctggggg acgagctcca cttagacggc gaggacgtgg 960
cgatggcgca tgccgacgcg ctagacgatt tcgatctgga catgttgggg gacggggatt 1020
ccccgggtcc gggatttacc ccccacgact ccgcccccta cggcgctctg gatatggccg 1080
acttcgagtt tgagcagatg tttaccgatg cccttggaat tgacgagtac ggtgggtagc 1140
aattgttgtt gttaacttgt ttattgc 1167

<210> SEQ ID NO 74
<211> LENGTH: 1304
<212> TYPE: DNA
<213> ORGANISM: Artificial Sequence
<220> FEATURE:
<223> OTHER INFORMATION: synthetic DNA used for plasmid constructs

<400> SEQUENCE: 74
gctagcgcta ccggactcag atctcgaggc caccatgggg caacccggga acggcagcgc 60
cttcttgctg gcacccaata gaagccatgc gccggaccac gacgtcacgc agcaaaggga 120
cgaggtgtgg gtggtgggca tgggcatcgt catgtctctc atcgtcctgg ccatcgtgtt 180
tggcaatgtg ctggtcatca cagccattgc caagttcgag cgtctgcaga cggtcaccaa 240
ctacttcatc acttcactgg cctgtgctga tctggtcatg ggcctggcag tggtgccctt 300
tggggccgcc catattctta tgaaaatgtg gacttttggc aacttctggt gcgagttttg 360
gacttccatt gatgtgctgt gcgtcacggc cagcattgag accctgtgcg tgatcgcagt 420
ggatcgctac tttgccatta cttcaccttt caagtaccag agcctgctga ccaagaataa 480
ggcccgggtg atcattctga tggtgtggat tgtgtcaggc cttacctcct tcttgcccat 540
tcagatgcac tggtaccggg ccacccacca ggaagccatc aactgctatg ccaatgagac 600
ctgctgtgac ttcttcacga accaagccta tgccattgcc tcttccatcg tgtccttcta 660
cgttcccctg gtgatcatgg tcttcgtcta ctccagggtc tttcaggagg ccaaaaggca 720
gctccagaag attgacaaat ctgagggccg cttccatgtc cagaacctta gccaggtgga 780
gcaggatggg cggacggggc atggactccg cagatcttcc aagttctgct tgaaggagca 840
caaagccctc aagacgttag gcatcatcat gggcactttc accctctgct ggctgccctt 900
cttcatcgtt aacattgtgc atgtgatcca ggataacctc atccgtaagg aagtttacat 960
cctcctaaat tggataggct atgtcaattc tggtttcaat ccccttatct actgccggag 1020
cccagatttc aggattgcct tccaggagct tctgtgtctg cgcaggtctt ctttgaaggc 1080
ctatgggaat ggctactcca gcaacggcaa cacaggggag cagagtggat atcacgtgga 1140
acaggagaaa gaaaataaac tgctgtgtga agacctccca ggcacggaag actttgtggg 1200
ccatcaaggt actgtgccta gcgataacat tgattcacaa gggaggaatt gtagtacaaa 1260
tgactcactg ctgtaacaat tgttgttgtt aacttgttta ttgc 1304

<210> SEQ ID NO 75
<211> LENGTH: 832
<212> TYPE: DNA
<213> ORGANISM: Artificial Sequence
<220> FEATURE:
<223> OTHER INFORMATION: synthetic DNA used for plasmid constructs

<400> SEQUENCE: 75
atcttggctg aggaatcttc taacaattta gagcttaaaa acgcccacga ggcggagaac 60
gaaatatcca gagagacgtt agaaacgttc aaaaacgttc gctagcgcca ccatggtgag 120
caagggcgag gagctgttca ccggggtggt gcccatcctg gtcgagctgg acggcgacgt 180
aaacggccac aagttcagcg tgtccggcga gggcgagggc gatgccacct acggcaagct 240
gaccctgaag ttcatctgca ccaccggcaa gctgcccgtg ccctggccca ccctcgtgac 300
caccttcggc tacggcctga tgtgcttcgc ccgctacccc gaccacatga agcagcacga 360
cttcttcaag tccgccatgc ccgaaggcta cgtccaggag cgcaccatct tcttcaagga 420
cgacggcaac tacaagaccc gcgccgaggt gaagttcgag ggcgacaccc tggtgaaccg 480
catcgagctg aagggcatcg acttcaagga ggacggcaac atcctggggc acaagctgga 540
gtacaactac aacagccaca acgtctatat catggccgac aagcagaaga acggcatcaa 600
ggtgaacttc aagatccgcc acaacatcga ggacggcagc gtgcagctcg ccgaccacta 660
ccagcagaac acccccatcg gcgacggccc cgtgctgctg cccgacaacc actacctgag 720
ctaccagtcc aagctgagca aagaccccaa cgagaagcgc gatcacatgg tcctgctgga 780
gttcgtgacc gccgccggga tcactctcgg catggacgag ctgtacaagt ag 832

<210> SEQ ID NO 76
<211> LENGTH: 227
<212> TYPE: DNA
<213> ORGANISM: Artificial Sequence
<220> FEATURE:
<223> OTHER INFORMATION: synthetic DNA used for plasmid constructs

<400> SEQUENCE: 76
gaaattaata cgactcacta taggggaccg gtcgccacca tgggctcgag caacctggtt 60
gcgcagctcg aaaacgaagt tgcgtctctg gaaaatgaga acgaaaccct gaagaaaaag 120
aacctgcaca aaaaagacct gatcgcgtac ctggagaaag aaatcgcgaa tctgcgtaag 180
aaaatcgaag aaggcggtgg cgggtcgcaa gagcggcagc agcagct 227

<210> SEQ ID NO 77
<211> LENGTH: 210
<212> TYPE: DNA
<213> ORGANISM: Artificial Sequence
<220> FEATURE:
<223> OTHER INFORMATION: synthetic DNA used for plasmid constructs

<400> SEQUENCE: 77
tgcagggtga cactcacgaa ggcggtggcg ggtcgaacct ggttgcgcag ctcgaaaacg 60
aagttgcgtc tctggaaaat gagaacgaaa ccctgaagaa aaagaacctg cacaaaaaag 120
acctgatcgc gtacctggag aaagaaatcg cgaatctgcg taagaaaatc gaagaatgat 180
aatgactcga gaaaatcagc ctcgactgtg 210

<210> SEQ ID NO 78
<211> LENGTH: 236
<212> TYPE: DNA
<213> ORGANISM: Artificial Sequence
<220> FEATURE:
<223> OTHER INFORMATION: synthetic DNA used for plasmid constructs

<400> SEQUENCE: 78
gaaattaata cgactcacta taggggaccg gtcgccacca tgggctcgag cgcgcgtaac 60
gcgtatctgc gtaagaaaat cgcacgtctg aaaaaagaca acctgcagct ggaacgtgat 120
gaacagaacc tggaaaaaat catcgcgaac ctgcgtgacg aaatcgcgcg tctcgaaaac 180
gaagttgcgt ctcacgaaca gggcggtggc gggtcgcaag agcggcagca gcagct 236

<210> SEQ ID NO 79
<211> LENGTH: 219
<212> TYPE: DNA

-continued

```
<213> ORGANISM: Artificial Sequence
<220> FEATURE:
<223> OTHER INFORMATION: synthetic DNA used for plasmid constructs

<400> SEQUENCE: 79

tgcagggtga cactcacgaa ggcggtggcg ggtcggcgcg taacgcgtat ctgcgtaaga     60

aaatcgcacg tctgaaaaaa gacaacctgc agctggaacg tgatgaacag aacctggaaa    120

aaatcatcgc gaacctgcgt gacgaaatcg cgcgtctcga aaacgaagtt gcgtctcacg    180

aacagtgata atgactcgag aaaatcagcc tcgactgtg                           219
```